US007358268B2

(12) United States Patent
Nazare et al.

(10) Patent No.: US 7,358,268 B2
(45) Date of Patent: Apr. 15, 2008

(54) IMIDAZOLE DERIVATIVES AS FACTOR XA INHIBITORS

(75) Inventors: Marc Nazare, Idstein (DE); Armin Bauer, Sulzbach (DE); Volkmar Wehner, Sandberg (DE); David W. Will, Kriftel (DE); Hans Matter, Langenselbold (DE); Michael Wagner, Alsbach (DE); Herman Schreuder, Hofheim-Lorsbach (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 300 days.

(21) Appl. No.: 10/728,339

(22) Filed: Dec. 4, 2003

(65) Prior Publication Data

US 2004/0171604 A1  Sep. 2, 2004

Related U.S. Application Data

(60) Provisional application No. 60/463,449, filed on Apr. 16, 2003, provisional application No. 60/507,338, filed on Sep. 30, 2003.

(30) Foreign Application Priority Data

Dec. 4, 2002 (EP) .................................. 02027120
May 19, 2003 (EP) .................................. 03011307

(51) Int. Cl.
*A61K 31/42* (2006.01)
*C07D 261/04* (2006.01)
*C07D 413/04* (2006.01)

(52) U.S. Cl. ..................................... 514/378; 548/247
(58) Field of Classification Search ................ 548/247; 514/378
See application file for complete search history.

(56) References Cited

U.S. PATENT DOCUMENTS

| | | | |
|---|---|---|---|
| 4,395,547 | A | 7/1983 | Raghu et al. |
| 6,020,357 | A | 2/2000 | Pinto et al. |
| 6,906,084 | B2 | 6/2005 | Nazaré et al. |
| 6,953,857 | B2 | 10/2005 | Nazaré et al. |
| 7,067,665 | B2 | 6/2006 | Nazaré et al. |
| 7,196,103 | B2 | 3/2007 | Nazaré et al. |
| 2004/0204406 | A1 | 10/2004 | Nazaré et al. |
| 2004/0235824 | A1 | 11/2004 | Nazaré et al. |
| 2005/0009827 | A1 | 1/2005 | Nazaré et al. |
| 2005/0009828 | A1 | 1/2005 | Nazaré et al. |
| 2005/0009829 | A1 | 1/2005 | Nazaré et al. |
| 2005/0043302 | A1 | 2/2005 | Nazaré et al. |
| 2007/0049573 | A1 | 3/2007 | Bauer et al. |

FOREIGN PATENT DOCUMENTS

| | | |
|---|---|---|
| EP | 0987274 | 3/2000 |
| WO | WO 92/06711 | 4/1992 |
| WO | WO 95/29189 | 11/1995 |
| WO | WO 96/12800 | 5/1996 |
| WO | WO 97/47651 | 12/1997 |
| WO | WO 01/07436 | 2/2001 |
| WO | WO 01/32628 | 5/2001 |
| WO | WO 02/00651 | 1/2002 |

OTHER PUBLICATIONS

Abad, et al., N-Multilabeled Adenine and Guanine Nucleosides. Syntheses Of [1,3,NH2-15N3]- and [2-13C-1,3,NH2-15N3]-Labeled Adenosine, Guanosine, 2'-Deoxyadenosine, and 2'-Deoxyguanosine, J. Org. Chem. 1999, 64, 6575-6582.
Abarbri, et al., Preparation Of New Polyfunctional Magnesiated Heterocycles Using A Chlorine-, Bromine-, or Iodine -Magnesium Exchange, J. Org. Chem. 2000, 65, 4618-4634.
Allen, et al., Self-Assembled Helices From 2,2'-Biimidazoles, Chem. Eur. J. 2001, 7(3), 721-729.
Anthony, et al., Design And In Vivo Analysis Of Potent Non-Thiol Inhibitors Of Farnesyl Protein Transferase, J. Med. Chem. 1999, 42, 3356-3368.
Adang, et al., A New Generation Of Orally Active Antithrombotics: Comparing Strategies In The GPIIb/IIIa, thrombin and Factor Xa areas, Drugs of the Future 2000, 25,369-383.
Baldwin, et al., Beta1-Selective Adrenoceptor Antagonists: Examples Of The 2-[4-[3-(Substituted Amino)-2-Hydroxypropoxyl] phenyl] Imidazole Class. 2, J. Med. Chem. 1986, 29, 1065-1080.
Baldwin, et al., 4-Trifluoromethylimidazoles And 5-(4-Pyridyl)-1,2,4-triazoles, New Classes Of Xanthine Oxidase Inhibitors, J. Med. Chem., 1975, 18(9), 895-900.
Baldwin, et al., Beta-Adrenergic Blocking Agents With Acute Antihypertensive Activity, J. Med. Chem., 1979, 22(6), 687-694.
Brackeen, et al., An Efficient And Mild Synthesis Of Highly Substituted Imidazoles, Tetrahedron Lett. 1994, 1635-1638.
Breslow, et al., Synthesis Of Some Polyimidazole Ligands Related To Zinc Enzymes, J. Am. Chem. Soc. 1983, 105, 5337-5342.
Bundgaard, et al., Novel Chemical Approaches in Prodrug Design, Drugs Of The Future, 16 (1991) 443-458.
Chan, et al., New N- and O-Arylations With Phenylboronic Acids And Cupric Acetate, Tetrahedron Letters 39 (1998) 2933-2936.
Cheng Yung-Chi et al., Relationship Between the Inhibition Constant (K1) and the Concentration of Inhibitor which causes 50 per cent Inhibition (I 50) of an Enzymatic Reaction, Biochem. Pharmacol., 1973, vol. 22, pp. 3099-3108.
Collman, et al., Catalytic Activities of Cu(II) Complexes with Nitrogen-Chelating Bidentate Ligands in the Coupling of Imidazoles with Arylboronic Acids, J. Org. Chem.; 66; 2001; pp. 7892-7897.

(Continued)

*Primary Examiner*—Taofiq Solola
(74) *Attorney, Agent, or Firm*—Jiang Lin; Ronald G. Ort; Julie Anne Knight

(57) ABSTRACT

This invention is directed to the compound of formula (I) which is useful for inhibiting the activity of Factor Xa. The present invention is also directed to compositions containing said compounds, processes for their preparation, their use, such as in inhibiting the formation of thrombin or for therapeutically or prophylactically treating a patient suffering from, or subject to, or associated with a disease state associated with a cardiovascular disorder.

5 Claims, No Drawings

OTHER PUBLICATIONS

Cozzi, et al., Ethyl-2-{[5,6-Dihydro-7-(1H-Imidazol-1-YL)2-Naphthalenyl] Oxy}-2-Methylpropanoate As A New Potent Oxyisobutyrate Hypolipidaemic With Unusual Features, Farmaco (1987) 42, 205-218.

Fleisher, et al., Improved Oral Drug Delivery: Solubility Limitations Overcome By The Use Of Prodrugs, Advanced Drug Delivery Reviews 19 (1996) 115-130.

Hartwig John F et al., Room-Temperature Palladium-Catalyzed Amination of Aryl Bromides and Chlorides and Extended Scope of Aromatic C-N Bond Formation with a Commercial Ligand, J. Org. Chem., 1999, vol. 64, pp. 5575-5580.

Hartwig, John, Transition Metal Catalyzed Synthesis of Arylamines and Aryl Ethers from Aryl Halides and Triflates: Scope and Mechanism, Angew. Chem. 1998, 37, 2046-2067.

Heindel, et al., Imidazole Carboxylates By A Claisen-Type Rearrangement Of Amidoxime-Propiolate Adducts, Tetrahedron Letters No. 1971, No. 18, pp. 1439-1440.

Jimonet, et al., Bioisosteres Of 9-Carboxymethyl-4-Oxo-Imidazol[1,2-a]Indeno-[1,2-e]Pyrazin-2-Carboxylic Acid Derivatives. Progress Towards Selective, Potent In Vivo AMPA Antagonists With Longer Durations Of Action, Bioorganic & Medicinal Chemistry Letters 2001, 11, 127-132.

Judd, et al., Bromobenzofuran-Based Non-Peptide Antagonists Of Angiotensin II: GR138950, A Potent Antihypertensive Agent With High Oral Bioavailability, J. Med. Chem. 1994, 37, 3108-3120.

Kang, et al., Copper-Catalyzed N-Arylation Of Aryl Iodides With Benzamides Or Nitrogen Heterocycles In The Presence Of Ethylenediamine, Synlett 2002, 3, 427-430.

Kempter, et al., Darstellung Von Heterocyclisch Substituierten Imidazolen Und Imidazo [2.1-b] Thiazolen, J. Prakt. Chem., 1971, 977-985.

Kim, et al, Preparation Of N(pi)-Alkyl- Histamine And Histidine Derivatives Through Efficient Alkylation Followed by Deprotection Using Activated Silica Gel, Tetrahedron Lett., 2000, 41, 10031-10034.

Kimbonguila, et al., On The Allyl Protection Of The Imidazole Ring Of Histidine, Tetrahedron, 1997, 53(37), 12525-12538.

Klapars, et al., A General And Efficient Copper Catalyst For The Amidation Of Aryl Halides And the N-Arylation of Nitrogen Heterocycles, J. Am. Chem. Soc. 2001, 123, 7727-7729.

Kwong, et al., Copper-Catalyzed Coupling Of Alkylamines And Aryl Iodides: An Efficient System Even In An Air Atmosphere, Organic Lett. 2002, 4 (4), 581-584.

Lam, et al., New Aryl/Heteroaryl C-N Bond Cross-coupling Reactions Via Arylboronic Acid/Cupric Acetate Arylation, Tetrahedron Letters 39 (1998) 2941-2944.

Mann Grace et al., Palladium-Catalyzed C-N(sp 2) Bond Formation: N-Arylation of Aromatic and Unsaturated Nitrogen and the Reductive Elimination Chemistry of Palladium Azolyl and Methyleneamido Complexes, J. Am. Chem. Soc., 1998, vol. 120, pp. 827-828.

Matthews, et al., Synthesis And Cardiotonic Activity Of Novel Biimidazoles, J. Med. Chem., 1990, 317-327.

Mederski Werner W K R et al., N-Aryl Heterocycles via Coupling Reactions with Arylboronic Acids, Tetrahedron, 1999, vol. 55, pp. 12757-12770.

Nichols, et al., 1-(2,5-Dimethoxy-4-(Trifluoromethyl) Phenyl)-2-Aminopropane: A Potent Serotonin 5-HT2A/2C Agonist, J. Med. Chem. 1994,37, 4336-4351.

O'Connell, et al., Convenient Synthesis Of Methyl 1-Methyl-2,4-dibromo-5-imidazolecarboxylate, Synthesis 1988, 767-771.

Ohmori, et al., Novel AMPA Receptor Antagonists: Synthesis and Structure-Activity Relationships of 1-Hydroxy-7-(1H-imidazol-1-yl)-6-nitro-2,3(1H,4H)-quinoxalinedione and Related Compounds, J. Med. Chem.; 39; 1996; pp. 3971-3979.

Old David W et al., Efficient Palladium-Catalyzed N-Arylation of Indoles, Organic Letters, 2000, vol. 2, No. 10, pp. 1403-1406.

Ostrem James A et al., Discovery of a Novel, Potent, and Specific Family of Factor Xa Inhibitors via Combinatorial Chemistry, Biochemistry, 1998, vol. 37, pp. 1053-1059.

Paul, et al., Imidazo[1,5-d][1,2,4]Triazines as Potential Antiasthma Agents, J. Med. Chem. 1985, 28, 1704-1716.

Pierce, et al., Practical Synthesis And Regioselective Alkylation Of Methyl 4(5)-Pentafluoroethyl)-2-Propylimidazole-5(4)-Carboxylate To Give DuP 532, A Potent Angiotensin II Antagonist, J. Org. Chem. 1993, 58, 4642-4645.

Qing, et al., First Synthesis Of Ortho-Trifluoromethylated Aryl Triflates, J. Chem Soc. Perkin Trans. I, 1997, 20, 3053-3057.

Sakamoto, et al. Palladium-Catalyzed Cyanation Of Aryl and Heteroaryl Iodides With Copper (I) Cyanide, J. Chem. Soc. Perkin Trans I, 1999, 2323-2326.

Segel Irwin H, Behavior and Analysis of Rapid Equilibrium and Steady-State Enzyme Systems, Enzyme Kinetics, 1975, John Wiley & Sons, New York, pp. 100-125.

Shi, et al., A Practical Synthesis Of 2-Butyl-4-(5)-Chloro-5(4)-Hydroxymethyl-1H-Imidazole, Synthetic Communications, 1993, 23(18), 2623-2630.

Shilcrat, et al., A New Regioselective Synthesis Of 1,2,5-Trisubstituted 1H-Imidazoles And Its Application To The Development Of Eprosartan, J. Org. Chem. 1997, 62, 8449-8454.

Su, et al., Methyl Chlorodifluoro Acetate A Convenient Trifluoromethylating Agent, Tetrahedron Lett. 1991, 32 (52), 7689-7690.

Tokmakov Gennadii P et al., Rearrangement of 1-Arylindoles to 5H-Dibenz[b,f]azepines, Tetrahedron, 1995, vol. 51, No. 7, pp. 2091-2098.

Umemoto, et al., Power And Structure-Variable Fluorinating Agents. The N-Fluoropyridinium Salt System, J. Am. Chem. Soc. 1990, 112, 8563-8575.

Unangst Paul C et al., Synthesis of Novel 1-Phenyl-1H-indole-2-carboxylic Acids. I. Utilization of Ullmann and Dieckmann Reactions for the Preparation of 3-Hydroxy, 3 -Alkoxy, and 3-Alkyl Derivatives, J. Heterocyclic Chem., 1987, vol. 24, pp. 811-815.

Urata, et al., A Novel And Convenient Method For Trifluoromethylation Of Organic Halides Using CF3SiR'3/FK/Cu(I) System, Tetrahedron Lett. 1991, 32(1), 91-94.

Veronese, et al., One-Pot Synthesis of 2-Vinylimidazole Derivatives By Reaction Of Alpha-Hydroxyimino-Beta Dicarbonyl Compounds With Allylamine, Synthesis 1985, 300-302.

Wegner, et al., Imidazole Aus Aldehyden, 1,2-Diketonen Und Fluessigem Ammoniak, Arch. Pharm., 1974, 492-495 English Abstract on p. 492.

Wolfe, et al., Simple, Efficient Catalyst System For The Palladium-Catalyzed Amination Of Aryl Chlorides, Bromides, and Triflates, J. Org. Chem. 2000, 65, 1158-1174.

Yamada, et al., 2-[(2-Aminobenzyl)sulfinyl]-1-(2-pyridyl)-1,4,5,6-tetrahydrocyclopent[d]imidazoles As A Novel Class of Gastric H+/K+-ATPase Inhibitors, J. Med. Chem. 1996, 39, 596-604.

Yamanaka, et al., Syntheses Of Heteroaromatic Carboxylic Acids Closely Related To Fusaic Acid, Chem. Pharm. Bull. 1983 31(12) 4549-4553.

Yang, et al., Palladium-Catalyzed Amination Of Aryl Halides And Sulfonates, J. Organomet. Chem. 1999, 576, 125.

U.S. Appl. No. 11/469,513, filed Sep. 1, 2006, Urmann et al.

Kawasaki, et al., Total Synthesis of Nortopsentins A-D, Marine Alkaloids, Chem. Pharm. Bull. 44(10) 1831-1839 (1996).

Veronese, et al., Syntheses of 2-Arylimidazole Derivatives Through Annelations Employing Benzylamines, J. Heterocyclic Chem., 17, 1723-1725 (1980).

IMIDAZOLE DERIVATIVES AS FACTOR XA INHIBITORS

This application claims the benefit of U.S. Provisional Application No. 60/463,449, filed Apr. 16, 2003 and U.S. Provisional Application No. 60/507,338, filed Sep. 30, 2003, the content of both of which are incorporated herein by reference.

FIELD OF THE INVENTION

The present invention relates to compounds of the formula I,

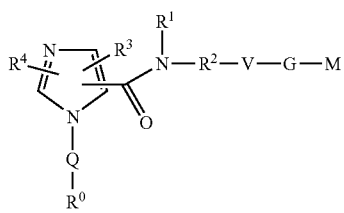

in which $R^0$; $R^1$; $R^2$; $R^3$; $R^4$; Q; V, G and M have the meanings indicated below. The compounds of the formula I are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formula I, their use, in particular as active ingredients in pharmaceuticals, and pharmaceutical preparations comprising them.

BACKGROUND OF THE INVENTION

Normal haemeostasis is the result of a complex balance between the processes of clot initiation, formation and clot dissolution. The complex interactions between blood cells, specific plasma proteins and the vascular surface, maintain the fluidity of blood unless injury and blood loss occurs (EP-A-987274). Many significant disease states are related to abnormal haemeostasis. For example, local thrombus formation due to rupture of atheroslerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation. It is most desirable to develop agents that inhibit coagulation without directly inhibiting thrombin but by inhibiting other steps in the coagulation cascade like factor Xa and/or factor VIIa activity. It is now believed that inhibitors of factor Xa carry a lower bleeding risk than thrombin inhibitors (A. E. P. Adang & J. B. M. Rewinkel, Drugs of the Future 2000, 25, 369-383). Low molecular weight, factor Xa-specific blood clotting inhibitors that are effective but do not cause unwanted side effects have been described, for example, in WO-A-95/29189.

However, besides being an effective factor Xa-specific blood clotting inhibitor, it is desirable that such inhibitors also have further advantageous properties, for instance stability in plasma and liver and selectivity versus other serine proteases whose inhibition is not intended, such as thrombin. There is an ongoing need for further low molecular weight factor Xa specific blood clotting inhibitors, which are effective and have the above advantages as well.

Specific inhibition of the factor VIIa/tissue factor catalytic complex using monoclonal antibodies (WO-A-92/06711) or a protein such as chloromethyl ketone inactivated factor VIIa (WO-A-96/12800, WO-A-97/47651) is an extremely effective means of controlling thrombus formation caused by acute arterial injury or the thrombotic complications related to bacterial septicemia. There is also experimental evidence suggesting that inhibition of factor VIIa/tissue factor activity inhibits restenosis following balloon angioplasty. Bleeding studies have been conducted in baboons and indicate that inhibition of the factor VIIa/tissue factor complex has the widest safety window with respect to therapeutic effectiveness and bleeding risk of any anticoagulant approach tested including thrombin, platelet and factor Xa inhibition. Certain inhibitors of factor VIIa have already been described. EP-A-987274, for example discloses compounds containing a tripeptide unit, which inhibit factor VIIa. However, the property profile of these compounds is still not ideal, and there is an ongoing need for further low molecular weight factor VIIa inhibitory blood clotting inhibitors The present invention satisfies the above needs by providing novel compounds of the formula I, which exhibit better factor Xa and/or factor VIIa inhibitory activity and are favorable agents with high bioavailability.

SUMMARY OF THE INVENTION

Thus, the present invention relates to compounds of the formula I,

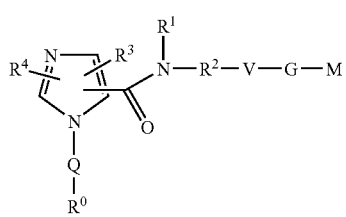

wherein
$R^0$ is 1) a monocyclic or bicyclic 6- to 14-membered aryl, wherein aryl is mono-, di- or trisubstituted independently of one another by R8,
2) a monocyclic or bicyclic 4- to 15-membered heterocyclyl out of the group pyridinyl, pyrimidinyl, indolyl, isoindolyl, indazolyl, phthalazinyl, quinolyl, isoquinolyl, benzothiophen, quinazolinyl and phenylpyridyl, wherein said heterocyclyl is unsubstituted or mono-, di- or trisubstituted independently of one another by R8, or
3) a monocyclic or bicyclic 4- to 15-membered heterocyclyl, containing one, two, three or four heteroatoms chosen from nitrogen, sulfur or oxygen, wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulfur or oxygen, wherein heterocyclyl is unsubstituted or mono-, di- or trisubstituted independently of one another by R8, R8 is 1) halogen,
2) —$NO_2$,
3) —CN,
4) —C(O)—$NH_2$,
5) —OH,
6) —$NH_2$,
7) —O—$CF_3$
8) a monocyclic or bicyclic 6- to 14-membered aryl, wherein aryl is mono-, di- or trisubstituted independently of one another by halogen or —O—($C_1$-$C_8$)-alkyl,
9) —($C_1$-$C_8$)-alkyl, wherein alkyl is unsubstituted or mono-, di- or trisubstituted independently of one another by halogen, $NH_2$, —OH or a methoxy residue,
10) —O—($C_1$-$C_8$)-alkyl, wherein alkyl is unsubstituted or mono-, di- or trisubstituted independently of one another by halogen, $NH_2$, —OH or a methoxy residue,
11) —$SO_2$—$CH_3$ or
12) —$SO_2$—$CF_3$, provided that R8 is at least one halogen, —C(O)—$NH_2$ or —O—($C_1$-$C_8$)-alkyl residue, if $R^0$ is a monocyclic or bicyclic 6- to 14-membered aryl, Q is a direct bond, —($C_0$-$C_2$)-alkylene-C(O)—$NR^{10}$—, —$NR^{10}$—C(O)—$NR^{10}$—, —$NR^{10}$—C(O)—, —$SO_2$—, —($C_1$-$C_6$)-alkylene, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—,
—$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —($C_2$-$C_3$)-alkylene-O—($C_0$-$C_3$)-alkylene-, —($C_2$-$C_3$)-alkylene-S(O)—, —($C_2$-$C_3$)-alkylene-S(O)$_2$—, —$(CH_2)_m$—$NR^{10}$—C(O)—O—$(CH_2)_n$—, —($C_2$-$C_3$)-alkylene-S(O)$_2$—NH—($R^{10}$)—, —($C_2$-$C_3$)-alkylene-N($R^{10}$)— or
—($C_0$-$C_3$)-alkylene-C(O)—O—, wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$ or —OH; or
—($C_3$-$C_6$)-cycloalkylen, wherein cycloalkylen is unsubstituted or mono-, di- or trisubstituted independently of one another by halogen, —$NH_2$ or —OH;

$R^1$ is a hydrogen atom, —($C_1$-$C_4$)-alkyl, wherein alkyl is unsubstituted or substituted one to three times by R13; —($C_1$-$C_3$)-alkylene-C(O)—NH—$R^0$, —($C_1$-$C_3$)-alkylene-C(O)—O—$R^{10}$, a monocyclic or bicyclic 6- to 14-membered aryl, wherein aryl is mono-, di- or trisubstituted independently of one another by R8, wherein R8 is as defined above; a monocyclic or bicyclic 4- to 15-membered heterocyclyl, containing one, two, three or four heteroatoms chosen from nitrogen, sulfur or oxygen; —($C_1$-$C_3$)-perfluoroalkylene,
—($C_1$-$C_3$)-alkylene-S(O)—($C_1$-$C_4$)-alkyl, —($C_1$-$C_3$)-alkylene-S(O)$_2$—($C_1$-$C_3$)-alkyl, —($C_1$-$C_3$)-alkylene-S(O)$_2$—N($R^{4'}$)—$R^{5'}$, —($C_1$-$C_3$)-alkylene-O—($C_1$-$C_4$)-alkyl, —($C_0$-$C_3$)-alkylene-($C_3$-$C_8$)-cycloalkyl, or —($C_0$-$C_3$)-alkylene-het, wherein het is a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, $R^{4'}$ and $R^{5'}$ are independent of one another are identical or different and are hydrogen atom or —($C_1$-$C_4$)-alkyl, $R^2$ is a direct bond or —($C_1$-$C_4$)-alkylene, or $R^1$ and $R^3$ together with the atoms to which they are bonded can form a 6- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, or $R^1$—N—$R^2$—V can form a 4- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, R14 is halogen, —OH, =O, —($C_1$-$C_8$)-alkyl, —($C_1$-$C_4$)-alkoxy, —$NO_2$, —($C_0$-$C_4$)-alkyl-C(O)—O—$R^{18}$, —CN, —($C_0$-$C_4$)-alkyl-N($R^{18}$)—$R^{21}$, —($C_0$-$C_4$)-alkyl-O—$R^{18}$, —($C_0$-$C_4$)-alkyl-het, —($C_0$-$C_8$)-alkyl-$SO_2$, —$SO_2$—($C_1$-$C_4$)-alkyl, —$SO_2$—N($R^{18}$)—$R^{21}$, —C(O)—NH—($C_1$-$C_8$)-alkyl, —C(O)—N—[($C_1$-$C_8$)-alkyl]$_2$,
—$NR^{18}$—C(O)—NH—($C_1$-$C_8$)-alkyl, —C(O)—$NH_2$, —S—$R^{18}$, or —$NR^{18}$—C(O)—NH—[($C_1$-$C_8$)-alkyl]$_2$, wherein $R^{18}$ and $R^{21}$ are independently from each other hydrogen atom, —($C_1$-$C_3$)-perfluoroalkyl or —($C_1$-$C_6$)-alkyl, V is 1) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14, 2) a 6- to 14-membered aryl, wherein aryl is unsubstituted or mono-, di- or trisubstituted independently of one another by R14, or 3) a monocyclic or bicyclic 4- to 15-membered heterocyclyl, wherein said heterocyclyl is unsubstituted or mono-, di- or trisubstituted independently of one another by R14, G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_n$— or —$(CH_2)_m$—$NR^{10}$—C(O)—O—$(CH_2)_n$—, n and m are independently of one another identical or different and are the integers zero, 1, 2, 3, 4, 5 or 6, M is 1) a hydrogen atom,
2) —($C_1$-$C_8$)-alkyl, wherein alkyl is unsubstituted or mono-, di- or trisubstituted independently of one another by R14, 3) —C(O)—N(R11)-R12,
4) —(CH$_2$)$_m$—NR$^{10}$,
5) a 6- to 14-membered aryl, wherein aryl is unsubstituted or mono-, di- or trisubstituted independently of one another by R14,
6) a monocyclic or bicyclic 4- to 15-membered heterocyclyl, wherein heterocyclyl is unsubstituted or mono-, di- or trisubstituted independently of one another by R14,
7) —(C$_3$-C$_8$)-cycloalkyl, wherein said cycloalkyl is unsubstituted or mono-, di- or trisubstituted independently of one another by R14, or
8) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14, wherein R14 is defined above, R$^3$ and R$^4$ are independent of one another are identical or different and are
1) hydrogen atom,
2) halogen,
3) —(C$_1$-C$_4$)-alkyl, wherein alkyl is unsubstituted or mono-, di- or trisubstituted independently of one another by R13,
4) —(C$_1$-C$_3$)-perfluoroalkyl,
5) phenyl, wherein phenyl is unsubstituted or mono-, di- or trisubstituted independently of one another by R13,
6) —(C$_0$-C$_4$)-alkylene-O—R19, wherein R19 is
   a) hydrogen atom,
   b) —(C$_1$-C$_4$)-alkyl, wherein alkyl is unsubstituted or mono-, di- or trisubstituted independently of one another by R13, or
   c) phenyl, wherein phenyl is unsubstituted or mono-, di- or trisubstituted independently of one another by R13,
   d) —CF$_3$, or
   e) —CHF$_2$,
7) —NO$_2$,
8) —CN,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —NR$^{10}$—SO$_2$—R$^{10}$,
16) —S—R$^{10}$,
17) —(C$_0$-C$_2$)alkylene-C(O)—O—(C$_2$-C$_4$)-alkylene-O—C(O)—(C$_1$-C$_4$)-alkyl,
18) —C(O)—O—C(R15, R16)-O—C(O)—R17,
19) —(C$_0$-C$_2$)alkylene-C(O)—O—(C$_2$-C$_4$)-alkylene-O—C(O)—O—(C$_1$-C$_6$)-alkyl,
20) —C(O)—O—C(R15, R16)-O—C(O)—O—R17,
21) —(C$_0$-C$_4$)-alkylene-(C$_6$-C$_{14}$)-aryl, wherein aryl is mono-, di- or trisubstituted independently of one another by R13,
22) —(C$_0$-C$_4$)-alkylene-(C$_4$-C$_{15}$)-heterocyclyl, wherein heterocyclyl is unsubstituted or mono-, di- or trisubstituted independently of one another by R13
23) —(C$_0$-C$_4$)-alkylene-(C$_3$-C$_8$)-cycloalkyl, wherein cycloalkyl is unsubstituted or mono-, di- or trisubstituted independently of one another by R13,
24) —(C$_0$-C$_4$)-alkylene-het, wherein het is unsubstituted or mono-, di- or trisubstituted independently of one another by R13, or
25) —(C$_0$-C$_4$)-alkylene-O—CH$_2$—(C$_1$-C$_3$)-perfluoroalkylene-CH$_2$—O—(C$_0$-C$_4$)-alkyl, 26) a residue from the following list

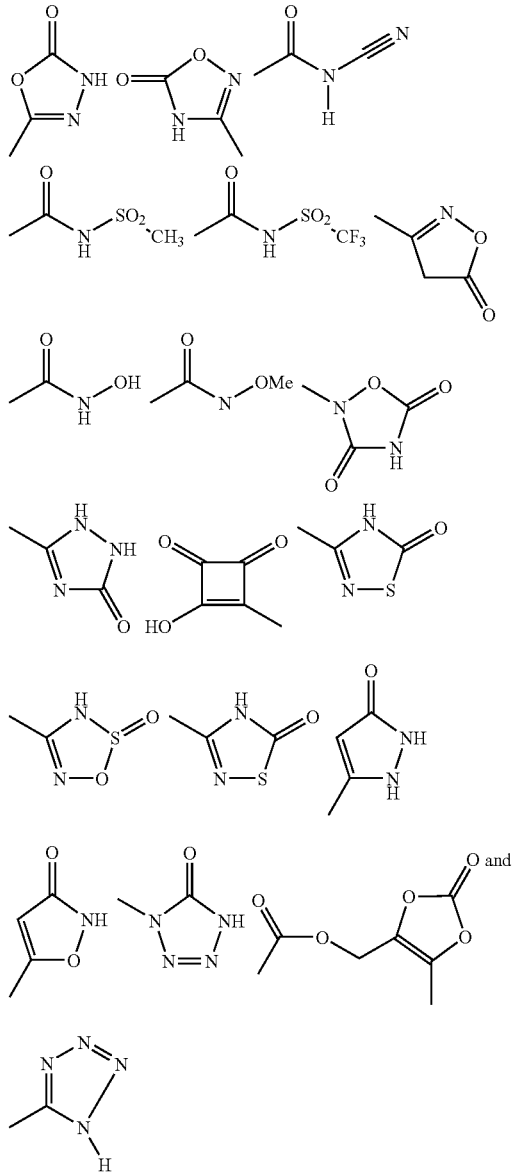

wherein Me is methyl, or
two —OR19 residues and adjacent atoms through which they are attached form together a 5- or 6-membered ring, that is unsubstituted or substituted one, two, three or four times by R13, R11 and R12 are independently of one another identical or different and are
1) hydrogen atom,
2) —(C$_1$-C$_6$)-alkyl, wherein alkyl is unsubstituted or mono-, di- or trisubstituted independently of one another by R13,
3) —(C$_0$-C$_6$)-alkyl-(C$_3$-C$_8$)-cycloalkyl,
4) —SO$_t$—R$^{10}$, wherein t is 1 or 2,
5) —(C$_0$-C$_6$)-alkyl-(C$_6$-C$_{14}$)-aryl, wherein alkyl and aryl independently from one another are unsubstituted or mono-, di- or trisubstituted by R13, 6) —(C$_1$-C$_3$)-perfluoroalkyl,
7) —O—R$^{17}$, or
8) —(C$_0$-C$_6$)-alkyl-(C$_4$-C$_{15}$)-heterocyclyl, wherein alkyl and heterocyclyl independently from one another are unsubstituted or mono-, di- or trisubstituted by R13, or R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13, R13 is halogen, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_8$)-cycloalkyl, —(C$_0$-C$_3$)-alkylene-O—R$^{10}$, —Si—(CH$_3$)$_3$, —N(R$^{10}$)—S(O)$_u$—R$^{10}$, wherein u is 1 or 2, —S—R$^{10}$, —SO$_r$—R$^{10}$, wherein r is 1 or 2, —S(O)$_v$—N(R$^{10}$)—R$^{20}$, wherein v is 1 or 2, —C(O)—R$^{10}$, —(C$_1$-C$_8$)-alkyl, —(C$_1$-C$_8$)-alkoxy, phenyl, phenyloxy-, —O—CF$_3$, —(C$_0$-C$_4$)-alkyl-C(O)—O—C(R15, R16)-O—C(O)—R$^{17}$, —(C$_1$-C$_4$)-alkoxy-phenyl, —(C$_0$-C$_4$)-alkyl-C(O)—O—C(R15, R16)-O—C(O)—O—R$^{17}$, —(C$_1$-C$_3$)-perfluoroalkyl, —O—R15, —NH—C(O)—NH—R$^{10}$, —NH—C(O)—O—R$^{10}$, or a residue from the following list

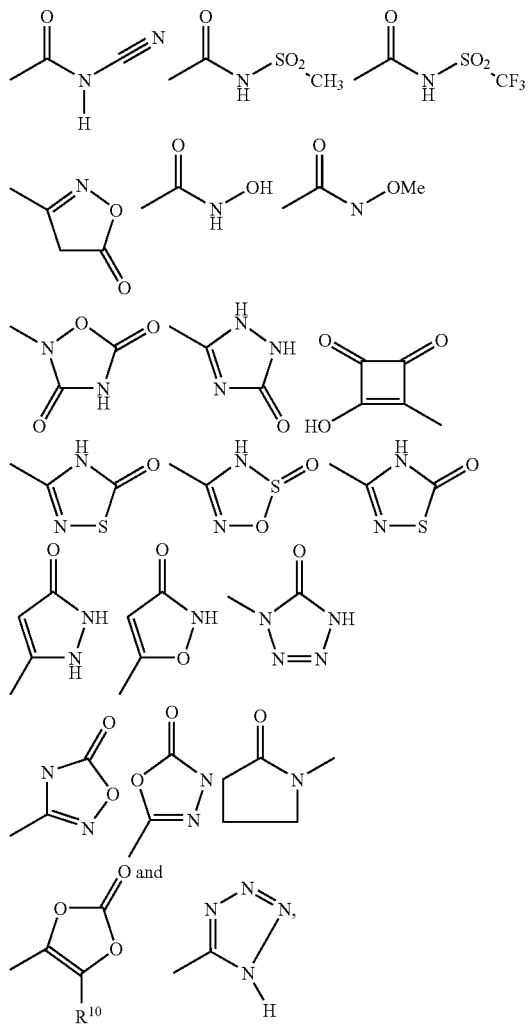

R$^{10}$ and R$^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-akyl or —(C$_1$-C$_3$)-perfluoroalkyl, R15 and R16 are independently of one another hydrogen, —(C$_1$-C$_6$)-alkyl, or together with the carbon atom to which they are bonded they can form a 3- to 6 membered carbocyclic ring which is unsubstituted or substituted one to three times by R$^{10}$, and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, or in all its stereoisomeric forms and mixtures thereof in any ratio, and its physiologically tolerable salts.

2) The present invention also relates to compounds of the formula I, wherein

R$^0$ is 1) a monocyclic or bicyclic 6- to 14-membered aryl, wherein aryl is mono-, di- or trisubstituted independently of one another by R8,
2) a monocyclic or bicyclic 4- to 15-membered heterocyclyl out of the group benzothiophen, indazolyl, indolyl, isoindolyl, isoquinolyl, phenylpyridyl, phthalazinyl, pyridyl, pyridinyl, pyrimidinyl, quinazolinyl and quinolyl, wherein said heterocyclyl is unsubstituted or mono-, di- or trisubstituted independently of one another by R8, or
3) a monocyclic or bicyclic 4- to 15-membered heterocyclyl, containing one, two, three or four heteroatoms chosen from nitrogen, sulfur or oxygen, wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulfur or oxygen, wherein heterocyclyl is unsubstituted or mono-, di- or trisubstituted independently of one another by R8, R8 is 1) halogen,
2) —NO$_2$,
3) —CN,
4) —C(O)—NH$_2$,
5) —OH,
6) —NH$_2$,
7) —O—CF$_3$
8) a monocyclic or bicyclic 6- to 14-membered aryl, wherein aryl is mono-, di- or trisubstituted independently of one another by halogen or —O—(C$_1$-C$_8$)-alkyl,
9) —(C$_1$-C$_8$)-alkyl, wherein alkyl is unsubstituted or mono-, di- or trisubstituted independently of one another by halogen, NH$_2$, —OH or a methoxy residue, or
10) —O—(C$_1$-C$_8$)-alkyl, wherein alkyl is unsubstituted or mono-, di- or trisubstituted independently of one another by halogen, NH$_2$, —OH or a methoxy residue,
11) —SO$_2$—CH$_3$ or
12) —SO$_2$—CF$_3$, provided that R8 is at least one halogen, —C(O)—NH$_2$ or —O—(C$_1$-C$_8$)-alkyl residue, if R$^0$ is a monocyclic or bicyclic 6- to 14-membered aryl, Q is a direct bond, —(C$_0$-C$_2$)-alkylene-C(O)—NR$^{10}$—, —NR$^{10}$—C(O)—NR$^{10}$—, —NR$^{10}$—C(O)—, —SO$_2$—, —(C$_1$-C$_6$)-alkylene, —(CH$_2$)$_m$—NR$^{10}$—C(O)—NR$^{10}$—(CH$_2$)$_n$—, —(CH$_2$)$_m$—NR$^{10}$—C(O)—(CH$_2$)$_n$—, —$(CH_2)_m$—S—$(CH_2)_n$—, —$(CH_2)_m$—C(O)—$(CH_2)_n$—, —$(CH_2)_m$—SO_2—NR^{10}—$(CH_2)_n$—, —$(CH_2)_m$—NR^{10}—SO_2—$(CH_2)_n$—, —$(CH_2)_m$—NR^{10}—SO_2—NR^{10}—$(CH_2)_n$—, —$(CH_2)_m$—CH(OH)—$(CH_2)_n$—, —$(CH_2)_m$—O—C(O)—NR^{10}—$(CH_2)_n$—, —$(C_2-C_3)$-alkylene-O—$(C_0-C_3)$-alkylene-, —$(C_2-C_3)$-alkylene-S(O)—, —$(C_2-C_3)$-alkylene-S(O)_2—, —$(CH_2)_m$—NR^{10}—C(O)—O—$(CH_2)_n$—, —$(C_2-C_3)$-alkylene-S(O)_2—NH—$(R^{10})$—, —$(C_2-C_3)$-alkylene-N$(R^{10})$— or
—$(C_0-C_3)$-alkylene-C(O)—O—, wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$ or —OH; or —$(C_3-C_6)$-cycloalkylen, wherein cycloalkylen is unsubstituted or mono-, di- or trisubstituted independently of one another by halogen, —$NH_2$ or —OH;

$R^1$ is a hydrogen atom, —$(C_1-C_4)$-alkyl, wherein alkyl is unsubstituted or substituted one to three times by R13; —$(C_1-C_3)$-alkylene-C(O)—NH—$R^0$, —$(C_1-C_3)$-alkylene-C(O)—O—R15, a monocyclic or bicyclic 6- to 14-membered aryl, wherein aryl is mono-, di- or trisubstituted independently of one another by R8, wherein R8 is as defined above; a monocyclic or bicyclic 4- to 15-membered heterocyclyl, containing one, two, three or four heteroatoms chosen from nitrogen, sulfur or oxygen; —$(C_1-C_3)$-perfluoroalkylene,
—$(C_1-C_3)$-alkylene-S(O)—$(C_1-C_4)$-alkyl, —$(C_1-C_3)$-alkylene-S(O)_2—$(C_1-C_3)$-alkyl,
—$(C_1-C_3)$-alkylene-S(O)_2—N$(R^{4'})$—$R^{5'}$, —$(C_1-C_3)$-alkylene-O—$(C_1-C_4)$-alkyl,
—$(C_0-C_3)$-alkylene-$(C_3-C_8)$-cycloalkyl, or —$(C_0-C_3)$-alkylene-het, wherein het is unsubstituted or mono-, di- or trisubstituted independently of one another by R14,
$R^{4'}$ and $R^{5'}$ are independent of one another are identical or different and are hydrogen atom or —$(C_1-C_4)$-alkyl,
$R^2$ is a direct bond or —$(C_1-C_4)$-alkylene, or
$R^1$ and R3 together with the atoms to which they are bonded can form a 6- to 8-membered cyclic group, containing up to 1, 2, 3 or 4 heteroatoms chosen from nitrogen, sulfur or oxygen, wherein said cyclic group is unsubstituted or mono-, di- or trisubstituted independently of one another by R14, or
$R^1$—N—$R^2$—V can form a 4- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14,
R14 is halogen, —OH, =O, —$(C_1-C_8)$-alkyl, —$(C_1-C_4)$-alkoxy, —$NO_2$, —$(C_0-C_4)$-alkyl-C(O)—O—$R^{18}$, —CN, —$(C_0-C_4)$-alkyl-N$(R^{18})$—$R^{21}$, —$(C_0-C_4)$-alkyl-O—$R^{18}$, —$(C_0-C_4)$-alkyl-het, —$(C_0-C_8)$-alkyl-SO_2, —SO_2—$(C_1-C_4)$-alkyl, —SO_2—N$(R^{18})$—$R^{21}$, —C(O)—NH—$(C_1-C_8)$-alkyl, —C(O)—N—[$(C_1-C_8)$-alkyl]_2, —NR^{18}—C(O)—NH—$(C_1-C_8)$-alkyl, —C(O)—$NH_2$, —S—$R^{18}$, or —NR^{18}—C(O)—NH—[$(C_1-C_8)$-alkyl]_2,
wherein $R^{18}$ and $R^{21}$ are independently from each other hydrogen atom,
—$(C_1-C_3)$-perfluoroalkyl or —$(C_1-C_6)$-alkyl,
V is 1) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14,
2) a 6- to 14-membered aryl, wherein aryl is unsubstituted or mono-, di- or trisubstituted independently of one another by R14, or
3) a monocyclic or bicyclic 4- to 15-membered heterocyclyl, wherein said heterocyclyl is unsubstituted or mono-, di- or trisubstituted independently of one another by R14,
G is a direct bond, —$(CH_2)_m$—NR^{10}—SO_2—NR^{10}—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—NR^{10}—$(CH_2)_n$—, —$(CH_2)$—SO_2—$(CH_2)_n$—, —$(CH_2)_m$—NR^{10}—C(O)—NR^{10}—$(CH_2)_n$—, —$(CH_2)_m$—NR^{10}—C(O)—$(CH_2)_n$—, —$(CH_2)_m$—C(O)—$(CH_2)_n$—, —$(CH_2)$—S—$(CH_2)_n$—, —$(CH_2)_m$—SO_2—NR^{10}—$(CH_2)_n$—, —$(CH_2)_m$—NR^{10}—SO_2—$(CH_2)_n$—, —$(CH_2)_m$—NR^{10}—, —$(CH_2)_m$—O—C(O)—NR^{10}—$(CH_2)_n$— or —$(CH_2)_m$—NR^{10}—C(O)—O—$(CH_2)_n$—,
n and m are independently of one another identical or different and are the integers zero, 1, 2, 3, 4, 5 or 6,
M is 1) a hydrogen atom,
2) —$(C_1-C_8)$-alkyl, wherein alkyl is unsubstituted or mono-, di- or trisubstituted independently of one another by R14,
3) —C(O)—N(R11)-R12,
4) —$(CH_2)_m$—NR^{10},
5) —$(C_6-C_{14})$-aryl, wherein aryl is unsubstituted or mono-, di- or trisubstituted independently of one another by R14,
6) —$(C_4-C_{15})$-heterocyclyl, wherein heterocyclyl is unsubstituted or mono-, di- or trisubstituted independently of one another by R14,
7) —$(C_3-C_8)$-cycloalkyl, wherein said cycloalkyl is unsubstituted or mono-, di- or trisubstituted independently of one another by R14, or
8) a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, wherein R14 is defined above,
$R^3$ and $R^4$ are independent of one another are identical or different and are
1) hydrogen atom,
2) halogen,
3) —$(C_1-C_4)$-alkyl, wherein alkyl is unsubstituted or mono-, di- or trisubstituted independently of one another by R13,
4) —$(C_1-C_3)$-perfluoroalkyl,
5) phenyl, wherein phenyl is unsubstituted or mono-, di- or trisubstituted independently of one another by R13,
6) —$(C_0-C_4)$-alkylene-O—R19, wherein R19 is
a) hydrogen atom,
b) —$(C_1-C_4)$-alkyl, wherein alkyl is unsubstituted or mono-, di- or trisubstituted independently of one another by R13, or
c) phenyl, wherein phenyl is unsubstituted or mono-, di- or trisubstituted independently of one another by R13,
d) —$CF_3$,
e) —$CHF_2$,
7) —$NO_2$,
8) —CN,
9) —$SO_s$—$R^{11}$, wherein s is 1 or 2,
10) —$SO_t$—N$(R^{11})$—$R^{12}$, wherein t is 1 or 2, 11) —(C₀-C₄)-alkylene-C(O)—R¹¹,
12) —(C₀-C₄)-alkylene-C(O)—O—R¹¹,
13) —(C₀-C₄)-alkylene-C(O)—N(R¹¹)—R¹²,
14) —(C₀-C₄)-alkylene-N(R¹¹)—R¹²,
15) —NR¹⁰—SO₂—R¹⁰,
16) —S—R¹⁰,
17) —(C₀-C₂)alkylene-C(O)—O—(C₂-C₄)-alkylene-O—C(O)—(C₁-C₄)-alkyl,
18) —C(O)—O—C(R15, R16)-O—C(O)—R17,
19) —(C₀-C₂)alkylene-C(O)—O—(C₂-C₄)-alkylene-O—C(O)—O—(C₁-C₆)-alkyl,
20) —C(O)—O—C(R15, R16)-O—C(O)—O—R17,
21) —(C₀-C₄)-alkylene-(C₆-C₁₄)-aryl, wherein aryl is mono-, di- or trisubstituted independently of one another by R13,
22) —(C₀-C₄)-alkylene-(C₄-C₁₅)-heterocyclyl, wherein heterocyclyl is unsubstituted or mono-, di- or trisubstituted independently of one another by R13
23) —(C₀-C₄)-alkylene-(C₃-C₈)-cycloalkyl, wherein cycloalkyl is unsubstituted or mono-, di- or trisubstituted independently of one another by R13,
24) —(C₀-C₄)-alkylene-het, wherein het is unsubstituted or mono-, di- or trisubstituted independently of one another by R13,
25) —(C₀-C₃)-alkylene-O—CH₂—(C₁-C₃)-perfluoro-alkylene-CH₂—O—(C₀-C₃)-alkyl, or
26) a residue from the following list

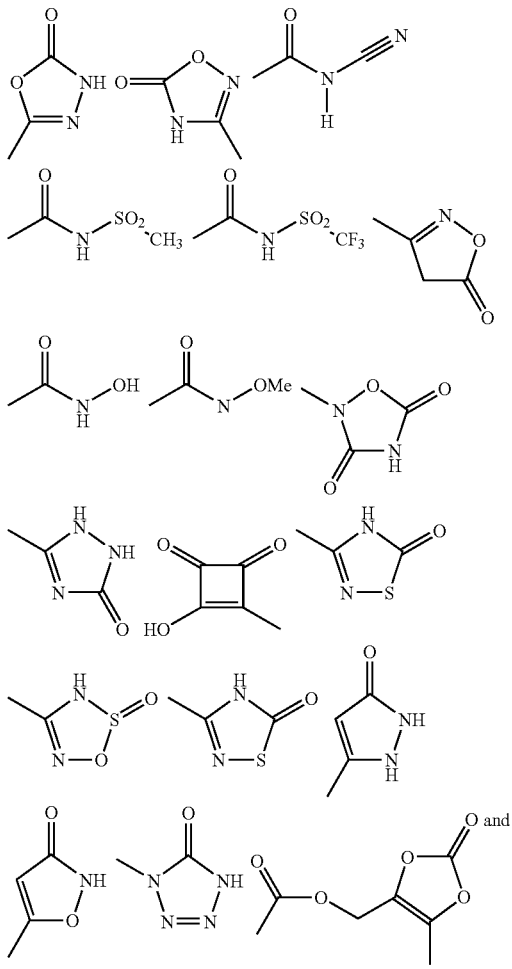

-continued

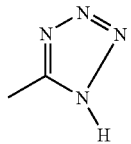

wherein Me is methyl, or
if two —OR19 residues are attached to adjacent atoms they can form together with the atoms which they are attached to a 5- or 6-membered ring, which is unsubstituted or substituted one, two, three or four times by R13,
R11 and R12 are independently of one another identical or different and are
1) hydrogen atom,
2) —(C₁-C₆)-alkyl, wherein alkyl is unsubstituted or mono-, di- or trisubstituted independently of one another by R13,
3) —(C₀-C₆)-alkyl-(C₃-C₈)-cycloalkyl,
4) —SO$_t$—R¹⁰, wherein t is 1 or 2,
5) —(C₀-C₆)-alkyl-(C₆-C₁₄)-aryl, wherein alkyl and aryl independently from one another are unsubstituted or mono-, di- or trisubstituted by R13,
6) —(C₁-C₃)-perfluoroalkyl,
7) —O—R¹⁷, or
8) —(C₀-C₆)-alkyl-(C₄-C₁₅)-heterocyclyl, wherein alkyl and heterocyclyl independently from one another are unsubstituted or mono-, di- or trisubstituted by R13, or
R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13,
R13 is halogen, —NO₂, —CN, =O, —OH, —CF₃, —C(O)—O—R¹⁰, —C(O)—N(R¹⁰)—R²⁰, —N(R¹⁰)—R²⁰,
—(C₃-C₈)-cycloalkyl, —(C₀-C₃)-alkylene-O—R¹⁰, —Si—(CH₃)₃, —N(R¹⁰)—S(O)$_u$—R¹⁰, wherein u is 1 or 2, —S—R¹⁰, —SO$_r$—R¹⁰, wherein r is 1 or 2, —S(O)$_v$—N(R¹⁰)—R²⁰, wherein v is 1 or 2, —C(O)—R¹⁰, —(C₁-C₈)-alkyl, —(C₁-C₈)-alkoxy, phenyl, phenyloxy-, —O—CF₃, —(C₀-C₄)-alkyl-C(O)—O—C(R15, R16)-O—C(O)—R17, —(C₁-C₄)-alkoxy-phenyl, —(C₀-C₄)-alkyl-C(O)—O—C(R15, R16)-O—C(O)—O—R17, —(C₁-C₃)-perfluoroalkyl, —O—R15, —NH—C(O)—NH—R¹⁰, —NH—C(O)—O—R¹⁰, or a residue selected from the group consisting of

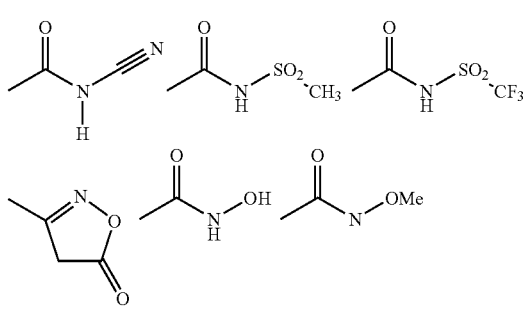

-continued

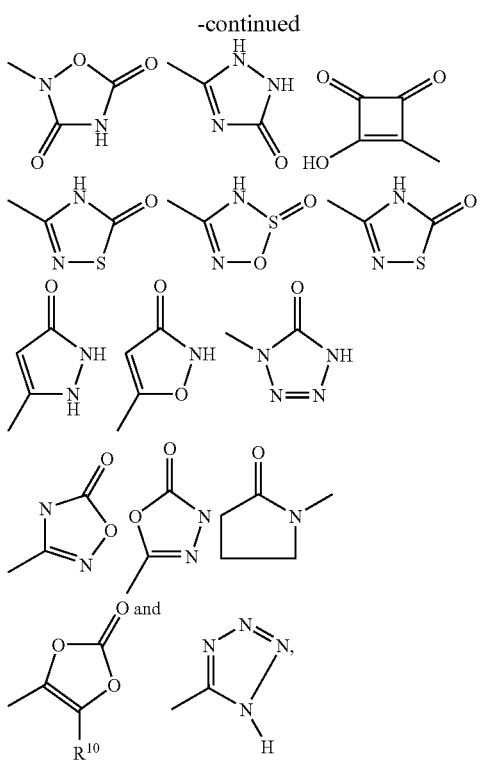

$R^{10}$ and $R^{20}$ are independently of one another hydrogen, —$(C_1-C_6)$-alkyl or —$(C_1-C_3)$-perfluoroalkyl, R15 and R16 are independently of one another hydrogen, —$(C_1-C_6)$-alkyl, or together with the carbon atom to which they are bonded they can form a 3- to 6 membered carbocyclic ring which is unsubstituted or substituted one to three times by $R^{10}$, and R17 is —$(C_1-C_6)$-alkyl, —$(C_1-C_6)$-alkyl-OH, —$(C_1-C_6)$-alkyl-O—$(C_1-C_6)$-alkyl, —$(C_3-C_8)$-cycloalkyl, —$(C_1-C_6)$-alkyl-O—$(C_1-C_8)$-alkyl-$(C_3-C_8)$-cycloalkyl, —$(C_1-C_6)$-alkyl-$(C_3-C_8)$-cycloalkyl, wherein said cycloalkyl ring is unsubstituted or substituted one, two or three times by —OH, —O—$(C_1-C_4)$-alkyl or $R^{10}$, in all its stereoisomeric forms and mixtures thereof in any ratio, and its physiologically tolerable salts 3) Thus, the present invention relates to compounds of the formula I, wherein $R^0$ is 1) a monocyclic or bicyclic 6- to 14-membered aryl out of the group phenyl, naphthyl, biphenylyl, anthryl or fluorenyl, wherein aryl is mono-, di- or trisubstituted independently of one another by R8, 2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridinyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or 3) a heterocyclyl, wherein heterocyclyl is selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R8, and which is additionally substituted by a heterocyclyl selected out of the group acridinyl, azabenzirnidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimnidazolyl, pyridothiazolyl, pyridinyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, wherein heterocyclyl is unsubstituted or mono-, di- or trisubstituted independently of one another by R8, R8 is 1) halogen,
2) $-NO_2$,
3) $-CN$,
4) $-C(O)-NH_2$,
5) $-OH$,
6) $-NH_2$,
7) $-O-CF_3$
8) a monocyclic or bicyclic 6- to 14-membered aryl, wherein aryl is as defined above and wherein aryl is mono-, di- or trisubstituted independently of one another by halogen or $-O-(C_1-C_8)$-alkyl,
9) $-(C_1-C_8)$-alkyl, wherein alkyl is unsubstituted or mono-, di- or trisubstituted independently of one another by halogen, $NH_2$, $-OH$ or a methoxy residue, or
10) $-O-(C_1-C_8)$-alkyl, wherein alkyl is unsubstituted or mono-, di- or trisubstituted independently of one another by halogen, $NH_2$, $-OH$ or a methoxy residue,
11) $-SO_2-CH_3$ or
12) $-SO_2-CF_3$, provided that R8 is at least one halogen, $-C(O)-NH_2$ or $-O-(C_1-C_8)$-alkyl residue, if $R^0$ is a monocyclic or bicyclic 6- to 14-membered aryl, wherein aryl is as defined above, Q is a direct bond, $-(C_0-C_2)$-alkylene-C(O)-$NR^{10}-$, $-NR^{10}-C(O)-NR^{10}-$, $-NR^{10}-C(O)-$, $-SO_2-$, $-(C_1-C_6)$-alkylene, $-(CH_2)_m-NR^{10}-C(O)-NR^{10}-(CH_2)_n-$, $-(CH_2)_m-NR^{10}-C(O)-(CH_2)_n-$, $-(CH_2)_m-S-(CH_2)_n-$, $-(CH_2)_m-C(O)-(CH_2)_n-$, $-(CH_2)_m-SO_2-NR^{10}-(CH_2)_n-$, $-(CH_2)_m-NR^{10}-SO_2-(CH_2)_n-$, $-(CH_2)_m-NR^{10}-SO_2-NR^{10}-(CH_2)_n-$, $-(CH_2)_m-CH(OH)-(CH_2)_n-$, $-(CH_2)_m-O-C(O)-NR^{10}-(CH_2)_n-$, $-(C_2-C_3)$-alkylene-O-$(C_0-C_3)$-alkylene-, $-(C_2-C_3)$-alkylene-S(O)-, $-(C_2-C_3)$-alkylene-S(O)_2-$, $-(CH_2)_m-NR^{10}-C(O)-O-(CH_2)_n-$, $-(C_2-C_3)$-alkylene-S(O)_2-NH-(R^{10})-$, $-(C_2-C_3)$-alkylene-N(R^{10})-$ or
$-(C_0-C_3)$-alkylene-C(O)-O-, wherein $R^{10}$ is as defined below, and wherein n and m are independently of one another identical or different and are the integers zero, 1, 2, 3, 4, 5 or 6, wherein the alkylene residues which are formed by $-(CH_2)_m-$ or $-(CH_2)_n-$ are unsubstituted or mono-, di- or trisubstituted independently of one another by halogen, $-NH_2$ or $-OH$; or $-(C_3-C_6)$-cycloalkylen, wherein cycloalkylen is unsubstituted or mono-, di- or trisubstituted independently of one another by halogen, $-NH_2$ or $-OH$;

$R^1$ is a hydrogen atom, $-(C_1-C_4)$-alkyl, wherein alkyl is unsubstituted or substituted one to three times by R13; $-(C_1-C_3)$-alkylene-C(O)-NH-$R^0$, $-(C_1-C_3)$-alkylene-C(O)-O-R15, an aryl out of the group phenyl, naphthyl, biphenylyl, anthryl or fluorenyl, wherein aryl is mono-, di- or trisubstituted independently of one another by R8, wherein R8 is as defined above;

a monocyclic or bicyclic 4- to 15-membered heterocyclyl, which is as defined above;

$-(C_1-C_3)$-perfluoroalkylene, $-(C_1-C_3)$-alkylene-S(O)-$(C_1-C_4)$-alkyl, $-(C_1-C_3)$-alkylene-S(O)_2-$(C_1-C_3)$-alkyl, $-(C_1-C_3)$-alkylene-S(O)_2-N(R^{4'})-R^{5'}$, $-(C_1-C_3)$-alkylene-O-$(C_1-C_4)$-alkyl, $-(C_0-C_3)$-alkylene-$(C_3-C_8)$-cycloalkyl, or $-(C_0-C_3)$-alkylene-het, wherein het is a residue selected out of the group azepine, azetidine, aziridine, azirine, 1,4-diazapane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, 1,2-oxa-thiepane, 1,2-oxathiolane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14, $R^{4'}$ and $R^{5'}$ are independent of one another are identical or different and are hydrogen atom or $-(C_1-C_4)$-alkyl, $R^2$ is a direct bond or $-(C_1-C_4)$-alkylene, or $R^1$ and R3 together with the atoms to which they are bonded can form a 6- to 8-membered cyclic residue selected out of the group azocane, azocane-2-one, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxazine, 1,3-oxazine, 1,4-oxazine, [oxocane, oxocan-2-one, piperazine, piperidine, pyran, pyrazine, pyridazine, pyrimidine or 5,6,7,8-tetrahydro-1H-azocin-2-one, wherein said cyclic group is unsubstituted or mono-, di- or trisubstituted independently of one another by R14, or $R^1-N-R^2-V$ can form a 4- to 8-membered cyclic group selected out of the group azepine, azetidine, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, wherein said cyclic group is unsubstituted or mono-, di- or trisubstituted independently of one another by R14, R14 is halogen, $-OH$, $=O$, $-(C_1-C_8)$-alkyl, $-(C_1-C_4)$-alkoxy, $-NO_2$, $-(C_0-C_4)$-alkyl-C(O)-O-$R^{18}$, —CN, —($C_0$-$C_4$)-alkyl-N($R^{18}$)—$R^{21}$, —($C_0$-$C_4$)-alkyl-O—$R^{18}$, —($C_0$-$C_4$)-alkyl-het, wherein het is a residue selected from azetidine, azetidinone, piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,4-diazepane, 1,2-diazepine, 1,3-diazepine, 1,4-diazepine, azepine, ketopiperazine, 1,4-oxazepane, oxazole, isoxazole, isoxazolidine, 2-isoxazoline, morpholine, thiazole, isothiazole, thiadiazole or thiomorpholine,
—($C_0$-$C_8$)-alkyl-$SO_2$, —$SO_2$—($C_1$-$C_4$)-alkyl, —$SO_2$—N($R^{18}$)—$R^{21}$, —C(O)—NH—($C_1$-$C_8$)-alkyl, —C(O)—N—[($C_1$-$C_8$)-alkyl]$_2$, —$NR^{18}$—C(O)—NH—($C_1$-$C_8$)-alkyl, —C(O)—$NH_2$, —S—$R^{18}$, or —$NR^{18}$—C(O)—NH—[($C_1$-$C_8$)-alkyl]$_2$, wherein $R^{18}$ and $R^{21}$ are independently from each other hydrogen atom, —($C_1$-$C_3$)-perfluoroalkyl or —($C_1$-$C_6$)-alkyl, V is 1) a monocyclic or bicyclic 6- to 14-membered aryl out of the group phenyl, naphthyl, biphenylyl, anthryl or fluorenyl, wherein aryl is mono-, di- or trisubstituted independently of one another by R14, 2) a heterocyclyl out of the group acridinyl, azaindole (1H-pyrrolopyridine), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 1,4-diazepane, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R14, G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_n$— or —$(CH_2)_m$—$NR^{10}$—C(O)—O—$(CH_2)_n$—, n and m are independently of one another identical or different and are the integers zero, 1,2, 3,4, 5 or 6, M is 1) a hydrogen atom,
2) —($C_1$-$C_8$)-alkyl, wherein alkyl is unsubstituted or mono-, di- or trisubstituted independently of one another by R14,
3) —C(O)—N(R11)-R12,
4) —$(CH_2)_m$—$NR^{10}$,
5) —($C_6$-$C_{14}$)-aryl, wherein aryl is as defined above and wherein aryl is unsubstituted or mono-, di- or trisubstituted independently of one another by R14,
6) —($C_4$-$C_{15}$)-heterocyclyl, wherein heterocyclyl is as defined above and is unsubstituted or mono-, di- or trisubstituted independently of one another by R14, or
7) —($C_3$-$C_8$)-cycloalkyl, wherein said cycloalkyl is unsubstituted or mono-, di- or trisubstituted independently of one another by R14, $R^3$ and $R^4$ are independent of one another are identical or different and are
1) hydrogen atom,
2) halogen,
3) —($C_1$-$C_4$)-alkyl, wherein alkyl is unsubstituted or mono-, di- or trisubstituted independently of one another by R13,
4) —($C_1$-$C_3$)-perfluoroalkyl,
5) phenyl, wherein phenyl is unsubstituted or mono-, di- or trisubstituted independently of one another by R13,
6) —($C_0$-$C_4$)-alkylene-O—R19, wherein R19 is
  a) hydrogen atom,
  b) —($C_1$-$C_4$)-alkyl, wherein alkyl is unsubstituted or mono-, di- or trisubstituted independently of one another by R13, or
  c) phenyl, wherein phenyl is unsubstituted or mono-, di- or trisubstituted independently of one another by R13,
  d) —$CF_3$,
  e) —$CHF_2$,
7) —$NO_2$,
8) —CN,
9) —$SO_s$—$R^{11}$, wherein s is 1 or 2,
10) —$SO_t$—N($R^{11}$)—$R^{12}$, wherein t is 1 or 2,
11) —($C_0$-$C_4$)-alkylene-C(O)—$R^{11}$,
12) —($C_0$-$C_4$)-alkylene-C(O)—O—$R^{11}$,
13) —($C_0$-$C_4$)-alkylene-C(O)—N($R^{11}$)—$R^{12}$,
14) —($C_0$-$C_4$)-alkylene-N($R^{11}$)—$R^{12}$,
15) —$NR^{10}$—$SO_2$—$R^{10}$,
16) —S—$R^{10}$,
17) —($C_0$-$C_2$)alkylene-C(O)—O—($C_2$-$C_4$)-alkylene-O—C(O)—($C_1$-$C_4$)-alkyl,
18) —C(O)—O—C(R15, R16)-O—C(O)—R17,
19) —($C_0$-$C_2$)alkylene-C(O)—O—($C_2$-$C_4$)-alkylene-O—C(O)—O—($C_1$-$C_6$)-alkyl,
20) —C(O)—O—C(R15, R16)-O—C(O)—O—R17,
21) —($C_0$-$C_4$)-alkylene-($C_6$-$C_{14}$)-aryl, wherein aryl is mono-, di- or trisubstituted independently of one another by R13, 22) —(C₀-C₄)-alkylene-(C₄-C₁₅)-heterocyclyl, wherein heterocyclyl is unsubstituted or mono-, di- or trisubstituted independently of one another by R13

23) —(C₀-C₄)-alkylene-(C₃-C₈)-cycloalkyl, wherein cycloalkyl is unsubstituted or mono-, di- or trisubstituted independently of one another by R13, 24) —(C₀-C₄)-alkylene-het, wherein het is unsubstituted or mono-, di- or trisubstituted independently of one another by R13, 25) —(C₀-C₃)-alkylene-O—CH₂—(C₁-C₃)-perfluoro-alkylene-CH₂—O—(C₀-C₃)-alkyl, or 26) a residue from the following list

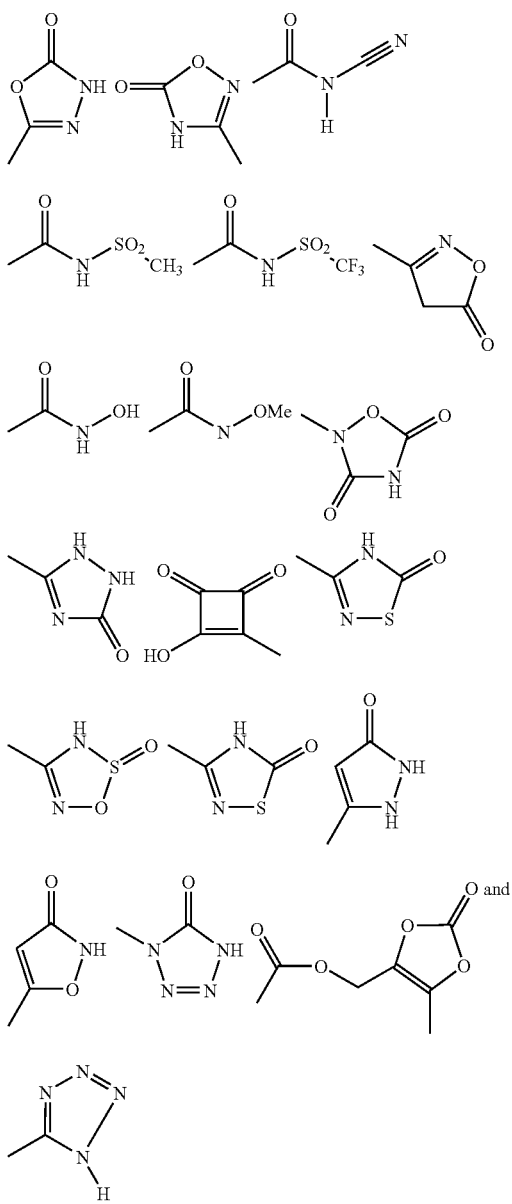

wherein Me is methyl, or if two —OR19 residues are attached to adjacent atoms they can form together with the atoms which they are attached to a 1,3-dioxole ring or a 2,3-dihydro-[1,4] dioxine ring, which is substituted one, two, three or four times by R13, R11 and R12 are independently of one another identical or different and are
1) hydrogen atom,
2) —(C₁-C₆)-alkyl, wherein alkyl is unsubstituted or mono-, di- or trisubstituted independently of one another by R13,
3) —(C₀-C₆)-alkyl-(C₃-C₈)-cycloalkyl,
4) —SO$_t$—R¹⁰, wherein t is 1 or 2,
5) —(C₀-C₆)-alkyl-(C₆-C₁₄)-aryl, wherein alkyl and aryl independently from one another are unsubstituted or mono-, di- or trisubstituted by R13,
6) —(C₁-C₃)-perfluoroalkyl,
7) —O—R¹⁷, or
8) —(C₀-C₆)-alkyl-(C₄-C₁₅)-heterocyclyl, wherein alkyl and heterocyclyl are as defined above and are independently from one another unsubstituted or mono-, di- or trisubstituted by R13, or R11 and R12 together with the nitrogen atom to which they are bonded form a heterocyclic ring out of the group azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, 1,4-oxazepinyl, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R13, R13 is halogen, —NO₂, —CN, =O, —OH, —CF₃, —C(O)—O—R¹⁰, —C(O)—N(R¹⁰)—R²⁰, —N(R¹⁰)—R²⁰,
—(C₃-C₈)-cycloalkyl, —(C₀-C₃)-alkylene-O—R¹⁰, —Si—(CH₃)₃, —N(R¹⁰)—S(O)$_u$—R¹⁰, wherein u is 1 or 2, —S—R¹⁰, —SO$_r$—R¹⁰, wherein r is 1 or 2, —S(O)$_v$—N(R¹⁰)—R²⁰, wherein v is 1 or 2, —C(O)—R¹⁰, —(C₁-C₈)-alkyl, —(C₁-C₈)-alkoxy, phenyl, phenyloxy-, —O—CF₃, —(C₀-C₄)-alkyl-C(O)—O—C(R15, R16)-O—C(O)—R17, —(C₁-C₄)-alkoxy-phenyl, —(C₀-C₄)-alkyl-C(O)—O—C(R15, R16)-O—C(O)—O—R17, —(C₁-C₃)-perfluoroalkyl, —O—R15, —NH—C(O)—NH—R¹⁰, —NH—C(O)—O—R¹⁰, or a residue from the following list

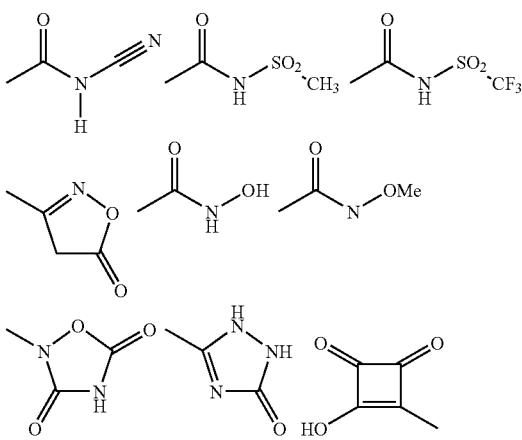

-continued

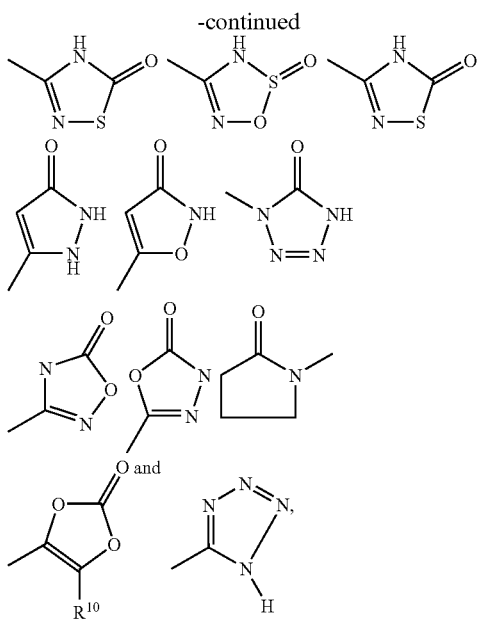

$R^{10}$ and $R^{20}$ are independently of one another hydrogen, —($C_1$-$C_6$)-alkyl, —($C_0$-$C_4$)-alkyl-OH, —($C_0$-$C_4$)-alkyl-O—($C_1$-$C_4$)-akyl or —($C_1$-$C_3$)-perfluoroalkyl, R15 and R16 are independently of one another hydrogen, —($C_1$-$C_6$)-alkyl, cyclopropyl, cyclobutyl, cyclopentyl or cyclohexyl, wherein each ring is unsubstituted or substituted one to three times by $R^{10}$, and R17 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or $R^{10}$, in all its stereoisomeric forms and mixtures thereof in any ratio, and its physiologically tolerable salts 4) The present invention also relates to the compounds of the formula I, wherein $R^0$ is 1) a monocyclic or bicyclic 6- to 14-membered aryl out of the group phenyl, naphthyl, biphenyl, anthryl or fluorenyl, wherein aryl is mono-, di- or trisubstituted independently of one another by R8,
  2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridinyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or
  3) a heterocyclyl out of the group azabenzimidazolyl, benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl or 3-thienyl, which is additionally substituted by a heterocyclyl selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, wherein heterocyclyl is unsubstituted or mono-, di- or trisubstituted independently of one another by R8, R8 is 1. fluorine, chlorine or bromine,
  2. —$NO_2$,
  3. —CN,
  4. —C(O)—$NH_2$,
  5. —OH,
  6. —$NH_2$,
  7. —$OCF_3$
  8. a monocyclic or bicyclic 6- to 14-membered aryl, wherein aryl is as defined above and is mono-, di- or trisubstituted independently of one another by halogen or —O—($C_1$-$C_8$)-alkyl,
  9. —($C_1$-$C_8$)-alkyl, wherein alkyl is unsubstituted or mono-, di- or trisubstituted independently of one another by halogen, $NH_2$, —OH or a methoxy residue, or
  10. —O—($C_1$-$C_8$)-alkyl, wherein alkyl is unsubstituted or mono-, di- or trisubstituted independently of one another by halogen, $NH_2$, —OH or a methoxy residue,
  11. —$SO_2CH_3$ or
  12. —$SO_2CF_3$, provided that R8 is at least one halogen, —C(O)—NH$_2$ or —O—(C$_1$-C$_8$)-alkyl residue, if R0 is a aryl or a heterocyclyl, which are as defined above, Q is a direct bond, —(C$_0$-C$_2$)-alkylene-C(O)—NR$^{10}$—, —NR$^{10}$—C(O)—NR$^{10}$—, —NR$^{10}$—C(O)—, —SO$_2$—, —(C$_1$-C$_6$)-alkylene, R$^1$ is a hydrogen atom, —(C$_1$-C$_4$)-alkyl, wherein alkyl is unsubstituted or substituted one to three times by R13; —(C$_1$-C$_3$)-alkylene-C(O)—NH—R$^0$, —(C$_1$-C$_3$)-alkylene-C(O)—O—R15, —(C$_1$-C$_3$)-perfluoroalkylene, —(C$_1$-C$_3$)-alkylene-S(O)—(C$_1$-C$_4$)-alkyl, —(C$_1$-C$_3$)-alkylene-S(O)$_2$—(C$_1$-C$_3$)-alkyl, —(C$_1$-C$_3$)-alkylene-S(O)$_2$—N(R$^{4'}$)—R$^{5'}$, —(C$_1$-C$_3$)-alkylene-O—(C$_1$-C$_4$)-alkyl, —(C$_0$-C$_3$)-alkylene-(C$_3$-C$_8$)-cycloalkyl, or —(C$_0$-C$_3$)-alkylene-het, wherein het is a residue selected out of the group azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14, R$^{4'}$ and R$^{5'}$ are independent of one another are identical or different and are hydrogen atom or —(C$_1$-C$_4$)-alkyl, R$^2$ is a direct bond or —(C$_1$-C$_4$)-alkylene, or R$^1$—N—R$^2$—V form a 4- to 8-membered cyclic group selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, wherein said cyclic group is unsubstituted or mono-, di- or trisubstituted independently of one another by R14, R14 is fluorine, chlorine, bromine, iodine, —OH, =O, —(C$_1$-C$_8$)-alkyl, —(C$_1$-C$_4$)-alkoxy, —NO$_2$, —C(O)—OH, —CN, —NH$_2$, —C(O)—O—(C$_1$-C$_4$)-alkyl, —(C$_1$-C$_8$)-alkylsulfonyl, —SO$_2$—(R$^{18}$)—R$^{21}$, —C(O)—NH—(C$_1$-C$_8$)-alkyl, —C(O)—N—[(C$_1$-C$_8$)-alkyl]$_2$, —NR$^{18}$—C(O)—NH—(C$_1$-C$_8$)-alkyl, —C(O)—NH$_2$, —S—R$^{18}$, or —NR$^{18}$—C(O)—NH—[(C$_1$-C$_8$)-alkyl]$_2$, wherein R$^{18}$ and R$^{21}$ are independently from each other hydrogen atom, —(C$_1$-C$_3$)-perfluoroalkyl or —(C$_1$-C$_6$)-alkyl, V is 1) a het residue out of the group azaindole (1H-pyrrolopyridine), azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine, thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, which is as defined above and wherein het is unsubstituted or mono-, di- or trisubstituted independently of one another by R14, or 2) phenyl, wherein phenyl is unsubstituted or mono-, di- or trisubstituted independently of one another by R14, G is a direct bond, —(CH$_2$)$_m$—NR$^{10}$—SO$_2$—NR$^{10}$—(CH$_2$)$_n$—, —(CH$_2$)$_m$—CH(OH)—(CH$_2$)$_n$—, —(CH$_2$)$_m$—, —(CH$_2$)$_m$—O—(CH$_2$)$_n$—, —(CH$_2$)$_m$—C(O)—NR$^{10}$—(CH$_2$)$_n$—, —(CH$_2$)—SO$_2$—(CH$_2$)$_n$—, —(CH$_2$)$_m$—NR$^{10}$—C(O)—NR$^{10}$—(CH$_2$)$_n$—, —(CH$_2$)$_m$—NR$^{10}$—C(O)—(CH$_2$)$_n$—, —(CH$_2$)$_m$—C(O)—(CH$_2$)$_n$—, —(CH$_2$)—S—(CH$_2$)$_n$—, —(CH$_2$)$_m$—SO$_2$—NR$^{10}$—(CH$_2$)$_n$—, —(CH$_2$)—NR$^{10}$—, —(CH$_2$)$_m$—NR$^{10}$—SO$_2$—(CH$_2$)$_n$—, —(CH$_2$)$_m$—NR$^{10}$—, —(CH$_2$)$_m$—O—C(O)—NR$^{10}$—(CH$_2$)$_n$— or —(CH$_2$)$_m$—NR$^{10}$—C(O)—O—(CH$_2$)$_n$—, n and m are independently of one another identical or different and are the integers zero, 1, 2, 3, 4, 5 or 6, M is 1) a hydrogen atom, 2) —(C$_1$-C$_8$)-alkyl, wherein alkyl is unsubstituted or mono-, di- or trisubstituted independently of one another by R14,

3) —C(O)—N(R11)-R12,

4) —(CH$_2$)$_m$—NR$^{10}$, 5) phenyl or naphthyl, wherein phenyl or naphthyl are unsubstituted or mono-, di- or trisubstituted independently of one another by R14, 6) heterocyclyl, wherein heterocyclyl is a residue out of the group which can be derived from azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiophene, thiomorpholine, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by R14, or 7) —(C$_3$-C$_8$)-cycloalkyl, wherein said cycloalkyl is unsubstituted or mono-, di- or trisubstituted independently of one another by R14, R$^3$ and R$^4$ are independent of one another are identical or different and are 1) hydrogen atom, 2) halogen, 3) —(C$_1$-C$_4$)-alkyl, wherein alkyl is unsubstituted or mono-, di- or trisubstituted independently of one another by R13, 4) —(C$_1$-C$_3$)-perfluoroalkyl, 5) phenyl, wherein phenyl is unsubstituted or mono-, di- or trisubstituted independently of one another by R13, 6) —(C₀-C₄)-alkylene-O—R19, wherein R19 is
   a) hydrogen atom,
   b) —(C₁-C₄)-alkyl, wherein alkyl is unsubstituted or mono-, di- or trisubstituted independently of one another by R13, or
   c) phenyl, wherein phenyl is unsubstituted or mono-, di- or trisubstituted independently of one another by R13,
   d) —CF₃, or
   e) CHF₂,
7) —CN,
8) —(C₀-C4)-alkylene-(C₄-C₁₅)-heterocyclyl, wherein heterocyclyl is as defined above and is unsubstituted or mono-, di- or trisubstituted independently of one another by R13,
9) —SO$_s$—R¹¹, wherein s is 1 or 2,
10) —SO$_t$—N(R¹¹)—R¹², wherein t is 1 or 2,
11) —(C₀-C₄)-alkylene-C(O)—R¹¹,
12) —(C₀-C₄)-alkylene-C(O)—O—R¹¹,
13) —(C₀-C₄)-alkylene-C(O)—N(R¹¹)—R¹²,
14) —(C₀-C₄)-alkylene-N(R¹¹)—R¹²,
15) —NR¹⁰—SO₂—R¹⁰,
16) —(C₀-C₄)-alkylene-het, wherein het is as defined above and is unsubstituted or mono-, di- or trisubstituted independently of one another by R13,
17) —(C₀-C2)alkylene-C(O)—O—(C₂-C₄)-alkylene-O—C(O)—(C₁-C₄)-alkyl,
18) —C(O)—O—C(R15, R16)-O—C(O)—R17,
19) —(C₀-C₂)alkylene-C(O)—O—(C₂-C₄)-alkylene-O—C(O)—O—(C₁-C₆)-alkyl,
20) —C(O)—O—C(R15, R16)-O—C(O)—O—R17,
21) —(C₀-C₄)-alkylene-(C₆-C₁₄)-aryl, wherein aryl is as defined above and is mono-, di- or trisubstituted independently of one another by R13,
22) —(C₀-C₄)-alkylene-(C₃-C₈)-cycloalkyl, wherein cycloalkyl is unsubstituted or mono-, di- or trisubstituted independently of one another by R13,
23) —(C₀-C₃)-alkylene-O—CH₂—CF₂—CH₂—O—(C₀-C₃)-alkyl,
24) —(C₀-C3)-alkylene-O—CH₂—CF₂—CF₂—CH₂—O—(C₀-C₃)-alkyl,
25) —(C₀-C₃)-alkylene-O—CH₂—(C₁-C₃)-perfluoroalkylene-CH₂—OH, or
26) a residue from the following list

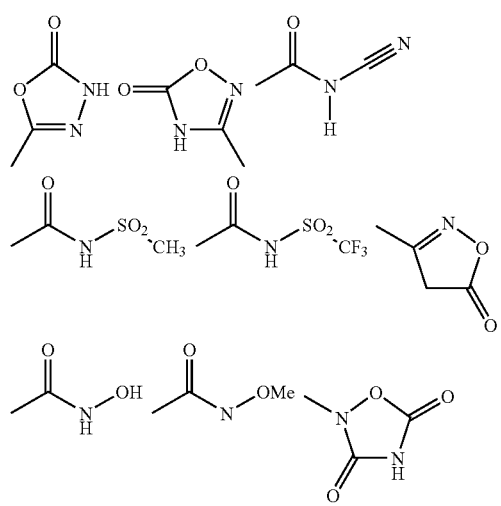

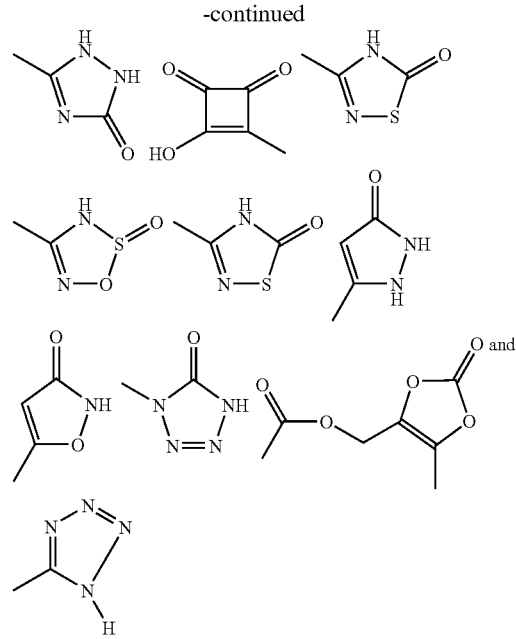

wherein Me is methyl,
if two —OR19 residues are attached to adjacent atoms they can form together with the atoms which they are attached to a 1,3-dioxole ring or a 2,3-dihydro-[1,4]dioxine ring, which is substituted one, two, three or four times by R13, R11 and R12 are independently of one another identical or different and are
1) hydrogen atom,
2) —(C₁-C₆)-alkyl, wherein alkyl is unsubstituted or mono-, di- or trisubstituted independently of one another by R13,
3) —(C₀-C₆)-alkyl-(C₆-C₁₄)-aryl, wherein aryl is as defined above and wherein alkyl and aryl are independently from one another unsubstituted or mono-, di- or trisubstituted by R13,
4) —O—R¹⁷, or
5) —(C₀-C₆)-alkyl-(C₄-C₁₅)-heterocyclyl, wherein alkyl and heterocyclyl is as defined above and independently from one another are unsubstituted or mono-, di- or trisubstituted by R13, or R11 and R12 together with the nitrogen atom to which they are bonded can form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, 1,4-oxazepine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, which is unsubstituted or mono-, di- or trisubstituted independently of one another by R13, R13 is fluorine, chlorine, bromine, iodine, —NO₂, —CN, =O, —OH, —CF₃, —C(O)—O—R¹⁰, —C(O)—N(R¹⁰)—R²⁰, —N(R¹⁰)—R²⁰, —(C₀-C₃)-alkylene-O—R¹⁰, —Si—(CH₃)₃, —N(R¹⁰)—S(O)₂—R¹⁰, —S—R¹⁰, —SO$_2$—R$^{10}$, —S(O)$_2$—N(R$^{10}$)—R$^{20}$, —C(O)—R$^{10}$, —(C$_1$-C$_8$)-alkyl, —(C$_1$-C$_8$)-alkoxy, phenyl, phenyloxy-, —O—CF$_3$, —(C$_1$-C$_3$)-perfluoroalkyl, —(C$_0$-C$_4$)-alkyl-C(O)—O—C(R15, R16)-O—C(O)—R17, —(C$_1$-C$_4$)-alkoxy-phenyl, —(C$_0$-C$_4$)-alkyl-C(O)—O—C(R15, R16)-O—C(O)—O—R17, —O—R15, —NH—C(O)—NH—R$^{10}$, —NH—C(O)—O—R$^{10}$, or a residue from the following list

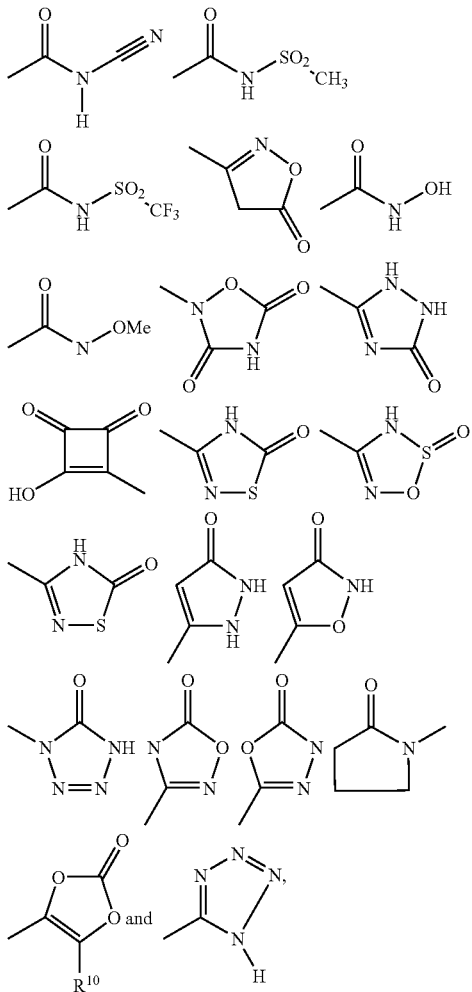

R$^{10}$ and R$^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-akyl or —(C$_1$-C$_3$)-perfluoroalkyl, R15 and R16 are independently of one another hydrogen, —(C$_1$-C$_6$)-alkyl, or together form a ring out of the group cyclopropyl, cyclobutyl, cyclopentyl or cyclohexyl, wherein each ring is unsubstituted or substituted one to three times by R$^{10}$, and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

5) The present invention also relates to the compounds of the formula I, wherein R0 is 1) phenyl, wherein phenyl is unsubstituted or mono-, di- or trisubstituted independently of one another by R8, 2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridinyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or 3) a heterocyclyl out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R8, and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said residue is unsubstituted or mono-, di- or trisubstituted independently of one another by R8

R8 is 1. F, Cl, Br or J,
2. —C(O)—NH$_2$,
3. —(C$_1$-C$_4$)-alkyl, wherein alkyl is unsubstituted or mono-, di- or trisubstituted independently of one another by halogen, —OH or a methoxy residue, or
4. —O—(C$_1$-C$_4$)-alkyl, wherein alkyl is unsubstituted or mono-, di- or trisubstituted independently of one another by halogen or a methoxy residue, provided that R8 is at least one halogen, —C(O)—NH$_2$ or —O—(C$_1$-C$_8$)-alkyl residue, if R0 is a aryl or a heterocyclyl, which are as defined above, Q is a direct bond, —C(O)—; —SO$_2$— or —(C$_1$-C$_6$)-alkylene, —(C$_0$-C$_2$)-alkylene-C(O)—NR$^{10}$—, R$^1$ is hydrogen atom, —(C$_1$-C$_2$)-alkyl, —(C$_1$-C$_3$)-alkylene-C(O)—NH—R0, —(C$_1$-C$_3$)-perfluoroalkylene, —(C$_1$-C$_3$)-alkylene-C(O)—O—R$^{15}$, —(C$_1$-C$_3$)-alkylene-S(O)$_2$—(C$_1$-C$_3$)-alkyl or —(C$_1$-C$_3$)-alkylene-S(O)$_2$—N(R$^{4'}$)—R$^{5'}$, wherein R$^{4'}$ and R$^{5'}$ are independent of one another are identical or different and are hydrogen atom or —(C$_1$-C$_4$)-alkyl, R$^2$ is a direct bond or —(C$_1$-C$_2$)-alkylene, R$^1$—N—R$^2$—V can form a 4- to 7-membered cyclic group out of the group azetidine, azetidinone, piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,4-diazepane, 1,2-diazepine, 1,3-diazepine, 1,4-diazepine, azepine, ketopiperazine, 1,4-oxazepane, oxazole, isoxazole, isoxazolidine, 2-isoxazoline, morpholine, thiazole, isothiazole, thiadiazole or thiomorpholine, wherein said cyclic group is unsubstituted or mono-, di- or trisubstituted independently of one another by R14, R14 is fluorine, chlorine, —OH, =O, —(C$_1$-C$_8$)-alkyl, —C(O)—OH, —CN, —NH$_2$, —C(O)—(C$_1$-C$_4$)-alkyl, —C(O)—NH—(C$_1$-C$_8$)-alkyl, —C(O)—N—[(C$_1$-C$_8$)-alkyl]$_2$, —C(O)—NH$_2$ or —N(R$^{18}$)—R$^{21}$, wherein $R^{18}$ and $R^{21}$ are independently from each other hydrogen atom, —$(C_1$-$C_3)$-perfluoroalkyl or —$(C_1$-$C_4)$-alkyl, V is 1. a cyclic residue out of the group containing compounds which are derived from azaindole (1H-pyrrolopyridine), aziridine, azirine, azetidine, azetidinone, 1,4-diazepane, pyrrole, pyrrolidine, pyridonyl, imidazole, pyrazole, 1,2,3-triazole, 1,2,4-triazole, tetrazole, pyridine, pyrimidine, pyrazine, 1,2,3-triazine, 1,2,4-triazine, 1,3,5-triazine, tetrazine, tetrazole, azepine, diazirine, 1,2-diazepine, 1,3-diazepine, 1,4-diazepine, pyridazine, piperidine, piperazine, pyrrolidinone, ketopiperazine, furan, pyran, dioxole, 1,4-oxazepane, oxazole, isoxazole, 2-isoxazoline, isoxazolidine, morpholine; oxirane, oxaziridine, 1,3-dioxolene, 1,3-dioxolane, 1,2-oxazine, 1,3-oxazine, 1,4-oxazine, oxaziridine, thiophene, thiopyran, thietan, thiazole, isothiazole, isothiazoline, isothiazolidine, 1,2-oxathiolan, thiodiazole, thiopyran, 1,2-thiazine, 1,3-thiazole, 1,3-thiazine, 1,4-thiazine, thiadiazine or thiomorpholine, wherein said cyclic residue is unsubstituted or mono-, di- or trisubstituted independently of one another by R14, or 2. phenyl, wherein phenyl is unsubstituted or mono-, di- or trisubstituted independently of one another by R14, or G is a direct bond, —$(CH_2)_m$—, or —$(CH_2)_m$—$NR^{10}$—, m is the integers zero, 1, 2, 3 or 4, M is 1. a hydrogen atom, 2. heterocyclyl, wherein heterocyclyl is a residue out of the group which can be derived from azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiomorpholine, thiophene, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by R14, 3. —$(C_1$-$C_6)$-alkyl, wherein alkyl is unsubstituted or mono-, di- or trisubstituted independently of one another by R14, or 4. $(C_3$-$C_6)$-cycloalkyl,

5. —C(O)—$N(R^{11})$—$R^{12}$, $R^3$ and $R^4$ are independent of one another are identical or different and are 1) hydrogen atom,
2) halogen,
3) —$(C_1$-$C_4)$-alkyl, wherein alkyl is unsubstituted or mono-, di- or trisubstituted independently of one another by R13,
4) —$(C_1$-$C_3)$-perfluoroalkyl,
5) phenyl, wherein phenyl is unsubstituted or mono-, di- or trisubstituted independently of one another by R13,
6) —$(C_0$-$C_4)$-alkylene-O—R19, wherein R19 is
  a) hydrogen atom,
  b) —$(C_1$-$C_4)$-alkyl, wherein alkyl is unsubstituted or mono-, di- or trisubstituted independently of one another by R13, or
  c) phenyl, wherein phenyl is unsubstituted or mono-, di- or trisubstituted independently of one another by R13,
  d) —$CF_3$, or
  e) $CHF_2$, 7) —CN,
8) —$NR^{10}$—$SO_2$—$R^{10}$,
9) —$SO_s$—$R^{11}$, wherein s is 1 or 2,
10) —$SO_t$—$N(R^{11})$—$R^{12}$, wherein t is 1 or 2,
11) —$(C_0$-$C_4)$-alkylene-C(O)—$R^{11}$,
12) —$(C_0$-$C_4)$-alkylene-C(O)—O—$R^{11}$,
13) —$(C_0$-$C_4)$-alkylene-C(O)—$N(R^{11})$—$R^{12}$,
14) —$(C_0$-$C_4)$-alkylene-$N(R^{11})$—$R^{12}$,
15) —$(C_0$-$C_2)$alkylene-C(O)—O—$(C_2$-$C_4)$-alkylene-O—C(O)—$(C_1$-$C_4)$-alkyl,
16) —C(O)—O—C(R15, R16)-O—C(O)—R17,
17) —$(C_0$-$C_2)$alkylene-C(O)—O—$(C_2$-$C_4)$-alkylene-O—C(O)—O—$(C_1$-$C_6)$-alkyl,
18) —C(O)—O—C(R15, R16)-O—C(O)—O—R17,
19) —$(C_0$-$C_4)$-alkylene-$(C_3$-$C_6)$-cycloalkyl, wherein cycloalkyl is unsubstituted or mono-, di- or trisubstituted independently of one another by R13, or
20) —$(C_0$-$C_3)$-alkylene-O—$CH_2$—$CF_2$—$CH_2$—O—$(C_0$-$C_3)$-alkyl,
21) —$(C_0$-$C_3)$-alkylene-O—$CH_2$—$CF_2$—$CF_2$—$CH_2$—O—$(C_0$-$C_3)$-alkyl,
22) —$(C_0$-$C_3)$-alkylene-O—$CH_2$—$(C_1$-$C_3)$-perfluoroalkylene-$CH_2$—OH, or
23) a residue from the following list

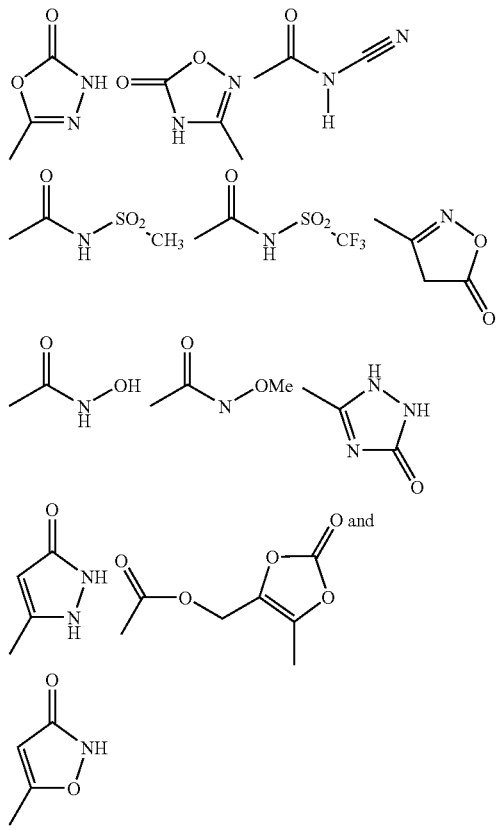

wherein Me is methyl, if two —OR19 residues are attached to adjacent atoms they can form together with the atoms which they are attached to a 1,3-dioxole ring or a 2,3-dihydro-[1,4] dioxine ring, which is substituted one, two, three or four times by R13, $R^{11}$ and $R^{12}$ together with the nitrogen atom to which they are bonded can form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]-oxazepane, 1,4-oxazepine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said ring is unsubstituted or mono-, di- or trisubstituted independently of one another by R13, R13 is fluorine, chlorine, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_0$-C$_3$)-alkylene-O—R$^{10}$, —Si—(CH$_3$)$_3$, —N(R$^{10}$)—S(O)$_2$—R$^{10}$, —SO$_2$—R$^{10}$, —S(O)$_2$—N(R$^{10}$)—R$^{20}$, —C(O)—R$^{10}$, —(C$_1$-C$_8$)-alkyl, —(C$_1$-C$_8$)-alkoxy, phenyl, phenyloxy-, —O—CF$_3$, —(C$_1$-C$_3$)-perfluoroalkyl, —NH—C(O)—NH—R$^{10}$, —(C$_0$-C$_4$)-alkyl-C(O)—O—C(R15, R16)-O—C(O)—R17, —(C$_1$-C$_4$)-alkoxy-phenyl, —(C$_0$-C$_4$)-alkyl-C(O)—O—C(R15, R16)-O—C(O)—O—R17, —O—R15, —NH—C(O)—O—R$^{10}$, or a residue from the following list

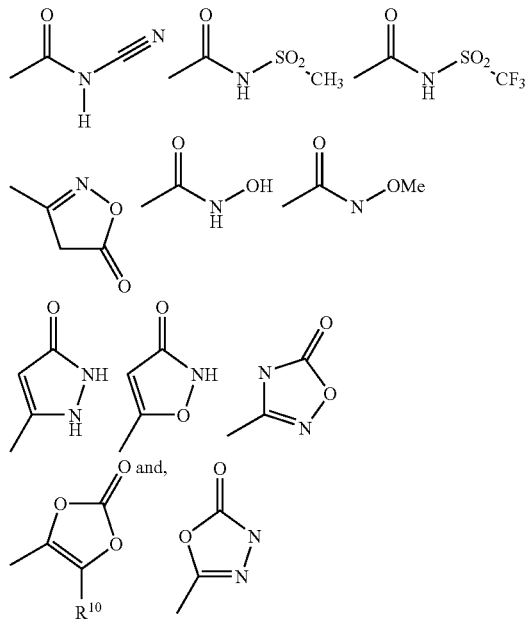

wherein Me is methyl,
R$^{10}$ and R$^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-akyl or —(C$_1$-C$_3$)-perfluoroalkyl,
R15 and R16 are independently of one another hydrogen, —(C$_1$-C$_6$)-alkyl, or together form a ring out of the group cyclopropyl, cyclobutyl, cyclopentyl or cyclohexyl, wherein each ring is unsubstituted or substituted one to three times by R$^{10}$, and
R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

6) The present invention also relates to the compounds of the formula I, wherein
R0 is 1) phenyl, wherein phenyl is unsubstituted or mono-, di- or trisubstituted independently of one another by R8,
2) a heterocyclyl selected out of the group indolyl, isoindolyl, benzofuranyl, benzothiophenyl, 1,3-benzodioxolyl, indazolyl, benzimidazolyl, benzoxazolyl, benzothiazolyl, quinolinyl, isoquinolinyl, chromanyl, isochromanyl, cinnolinyl, quinazolinyl, quinoxalinyl, phthalazinyl, pyridoimidazolyl, pyridopyridinyl, pyridopyrimidinyl, pyridinyl, purinyl and pteridinyl, wherein said heterocyclyl is unsubstituted or mono-, di- or trisubstituted independently of one another by R8,
3) a heterocyclyl out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R8,
and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said residue is unsubstituted or mono-, di- or trisubstituted independently of one another by R8
R8 is 1. is F, Cl, Br, J,
2. —C(O)—NH$_2$,
3. —(C$_1$-C$_4$)-alkyl, wherein alkyl is unsubstituted or mono-, di- or trisubstituted independently of one another by halogen, —OH or a methoxy residue, or
4. —O—(C$_1$-C$_4$)-alkyl, wherein alkyl is unsubstituted or mono-, di- or trisubstituted independently of one another by halogen or a methoxy residue, provided that R8 is at least one halogen, —C(O)—NH$_2$ or —O—(C$_1$-C$_8$)-alkyl residue, if R0 is a aryl or a heterocyclyl, which are as defined above,
Q is a direct bond, —C(O)—; —SO$_2$— or —(C$_1$-C$_6$)-alkylen, —(C$_0$-C$_2$)-alkylen-C(O)—NR$^{10}$—,
R$^1$ is hydrogen atom or —(C$_1$-C$_2$)-alkyl,
R$^2$ is a direct bond or —(C$_1$-C$_2$)-alkylen, or
R$^1$—N—R$^2$—V can form a 4- to 7-membered cyclic group out of the group piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole or thiomorpholine, wherein said cyclic group is unsubstituted or mono-, di- or trisubstituted independently of one another by R14,
R14 is fluoro, chlorine, —(C$_1$-C$_4$)-alkyl or —NH$_2$,
V is 1. a cyclic residue out of the group containing compounds, which are derived from azaindolyl (1H-pyrrolopyridyl), azetidine, azepine, aziridine, azirine, 1,4-diazepane, 1,2-diazepine, 1,3-diazepine, 1,4-diazepine, diazirine, 1,3-dioxolane, dioxazole, furan, imidazole, isoquinoline, isothiazole, isothiazolidine, isothiazoline, isoxazole, 2-isoxazoline, isoxazolidine, ketopiperazine, morpholine, 1,2-oxazine, 1,3-oxazine, 1,4-oxazine, oxazole, 1,2-oxathiolan, piperidine, pyran, pyrazine, pyrazole, pyridazine, piperazine, pyridine, pyridone, pyrimidine, pyrrole, pyrrolidine, pyrrolidinone, quinazoline, quinoline, tetrazine, tetrazole, thiadiazine, 1,2-thiazine, 1,3-thiazine, 1,4-thiazine, 1,3-thiazole, thietan, thiomorpholine, thiophene, thiopyran, 1,2,3-triazine, 1,2,4-triazine, 1,3,5-triazine, 1,2,3-triazole or 1,2,4-triazole,
wherein said cyclic residue is unsubstituted or mono-, di- or trisubstituted independently of one another by R14, or
2. phenyl, wherein phenyl is unsubstituted or mono-, di- or trisubstituted independently of one another by R14, G is a direct bond, $-(CH_2)_m-$, or $-(CH_2)_m-NR^{10}-$,
m is the integers zero, 1, 2, 3 or 4,
M is 1. a hydrogen atom,
2. heterocyclyl, wherein heterocyclyl is a residue out of the group which can be derived from 1,4-diazepane, ketomorpholine, thiophene, pyridazone, piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, 1,4,5,6-tetrahydro-pyridazinyl, thiadiazole or thiomorpholine, wherein said heterocyclyl is unsubstituted or mono-, di- or trisubstituted independently of one another by R14,
3. $-(C_1-C_6)$-alkyl, wherein alkyl is unsubstituted or mono-, di- or trisubstituted independently of one another by R14, or
4. $(C_3-C_6)$-cycloalkyl, $R^3$ and $R^4$ are independent of one another are identical or different and are
1) hydrogen atom,
2) halogen,
3) $-(C_1-C_4)$-alkyl, wherein alkyl is unsubstituted or mono-, di- or trisubstituted independently of one another by R13,
4) $-(C_1-C3)$-perfluoroalkyl,
5) phenyl, wherein phenyl is unsubstituted or mono-, di- or trisubstituted independently of one another by R13,
6) $-(C_0-C_4)$-alkylene-O—R19, wherein R19 is
  a) hydrogen atom,
  b) $-(C_1-C_4)$-alkyl, wherein alkyl is unsubstituted or mono-, di- or trisubstituted independently of one another by R13, or
  c) phenyl, wherein phenyl is unsubstituted or mono-, di- or trisubstituted independently of one another by R13,
  d) $-CF_3$, or
  e) $-CHF_2$,
7) $-CN$,
8) $-NR^{10}-SO_2-R^{10}$,
9) $-SO_s-R^{11}$, wherein s is 1 or 2,
10) $-SO_t-N(R^{11})-R^{12}$, wherein t is 1 or 2,
11) $-(C_0-C_4)$-alkylene-C(O)—R11,
12) $-(C_0-C_4)$-alkylene-C(O)—O—R11,
13) $-(C_0-C_4)$-alkylene-C(O)—N(R11)—R12,
14) $-(C_0-C_4)$-alkylene-N(R11)—R12,
15) $-(C_0-C_2)$alkylene-C(O)—O—(C_2-C_4)$-alkylene-O—C(O)—(C_1-C_4)$-alkyl,
16) $-C(O)-O-C(R15, R16)-O-C(O)-R17$,
17) $-(C_0-C_2)$alkylene-C(O)—O—(C_2-C_4)$-alkylene-O—C(O)—O—(C_1-C_6)$-alkyl,
18) $-C(O)-O-C(R15, R16)-O-C(O)-O-R17$,
19) $-(C_0-C_3)$-alkylene-$(C_3-C_6)$-cycloalkyl, wherein cycloalkyl is unsubstituted or mono-, di- or trisubstituted independently of one another by R13,
20) $-(C_0-C_4)$-alkylene-$(C_3-C_6)$-cycloalkyl, wherein cycloalkyl is unsubstituted or mono-, di- or trisubstituted independently of one another by R13, or
21) $-(C_0-C_3)$-alkylene-O—CH_2—CF_2—CH_2—O—(C_0-C_3)$-alkyl,
22) $-(C_0-C_3)$-alkylene-O—CH_2—CF_2—CF_2—CH_2—O—(C_0-C_3)$-alkyl,
23) $-(C_0-C_3)$-alkylene-O—CH_2—(C_1-C_3)$-perfluoroalkylene-CH_2—OH, or
24) a residue from the following list wherein Me is methyl,
R11 and R12 are independently of one another identical or different and are
1) hydrogen atom,
2) $-(C_1-C_4)$-alkyl, wherein alkyl is unsubstituted or mono-, di- or trisubstituted independently of one another by R13,
3) $-(C_0-C_6)$-alkyl-$(C_3-C_6)$-cycloalkyl,
4) $-O-R^{17}$, or
5) $-(C_0-C_6)$-alkyl-$(C_4-C_{15})$-heterocyclyl, wherein alkyl and heterocyclyl independently from one another are unsubstituted or mono-, di- or trisubstituted by R13 and wherein heterocyclyl is selected out of the group azetidine, cyclopropyl, cyclobutyl, 4,5-dihydro-oxazole, imidazolidine, morpholine, (1,4)-oxazepane, oxazolidine, piperidine, piperazine, pyrrolidine, tetrahydrothiophene, thiazolidine or thiomorpholine, or
R11 and R12 together with the nitrogen atom to which they are bonded form a heterocyclic ring, which is selected out of the group azetidine, cyclopropyl, cyclobutyl, 4,5-dihydro-oxazole, imidazolidine, morpholine, (1,4)-oxazepane, 1,4-oxazepine, oxazolidine, piperidine, piperazine, pyrrolidine, tetrahydrothiophene, thiazolidine or thiomorpholine, R13 is fluorine, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_6$)-cycloalkyl, —(C$_0$-C$_3$)-alkylene-O—R$^{10}$, —Si—(CH$_3$)$_3$, —S—R$^{10}$, —SO$_2$—R$^{10}$, —(C$_1$-C$_3$)-perfluoroalkyl, or a residue from the following list wherein Me is methyl, R$^{10}$ and R$^{20}$ are independently of one another hydrogen, —(C$_1$-C$_4$)-alkyl or —(C$_1$-C$_3$)-perfluoroalkyl, R$^{15}$ and R$^{16}$ are independently of one another hydrogen, —(C$_1$-C$_4$)-alkyl, or together form a ring out of the group cyclopropyl, cyclobutyl, cyclopentyl or cyclohexyl, wherein each ring is unsubstituted or substituted one to three times by R$^{10}$, and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

7) The present invention also relates to the compounds of the formula I, wherein R0 is 1. phenyl, wherein phenyl is unsubstituted or mono- or disubstituted independently of one another by R8,
2. pyridyl, wherein pyridyl is unsubstituted or mono- or disubstituted independently of one another by R8, or
3. a heterocyclyl out of the group thienyl, thiadiazolyl, isoxazolyl and thiazolyl, wherein said heterocyclyl is substituted by a residue selected out of the group thienyl, 2-thienyl and 3-thienyl, wherein said residue is unsubstituted or mono- or disubstituted independently of one another by R8, R8 is F, Cl, Br, —OCH$_3$, —C(O)—NH$_2$ or —O—CF$_3$, Q is a direct bond, —C(O)—; —SO$_2$—, —CH$_2$—C(O)—NH—, methylene or ethylene, R$^1$ is hydrogen atom, R$^2$ is a direct bond or methylene, R$^1$—N—R$^2$—V can form a 4- to 8-membered cyclic group out of the group azetidine, pyrrolidine, piperidine and piperazine, R14 is fluorine, chlorine, methyl, ethyl or —NH$_2$, V is 1. a residue out of the group containing compounds which is derived from azaindolyl (1H-pyrrolopyridyl), azetidine, 1,4-diazepane, isoxazole, isoquinoline, piperazine, piperidine, pyrazine, pyridazine, pyrimidine, pyrrolidine, quinazoline, quinoline or tetrahydropyrane, wherein said cyclic residue is unsubstituted or mono- or disubstituted independently of one another by R14, or
2. phenyl, wherein phenyl is unsubstituted or mono- or disubstituted independently of one another by R14, G is a direct bond, —(CH$_2$)$_m$—, or —(CH$_2$)$_m$—NR$^{10}$—, m is the integers zero, 1 or 2, M is a hydrogen atom, (C$_2$-C$_4$)-alkyl, azepanyl, cyclopropyl, cyclobutyl, cyclopentyl, cyclohexyl, imidazolyl, ketomorpholinyl, morpholinyl, [1,4]Oxazepanyl, piperidinyl, piperidonyl, pyrazinyl, pyrazolyl, pyridazinyl, pyridinyl, pyrimidyl, pyrrolidinyl, 1,4,5,6-tetrahydro-pyridazinyl, or tetrahydropyranyl, wherein the residues are unsubstituted or mono- or disubstituted independently of one another by R14

R$^3$ and R$^4$ are independent of one another are identical or different and are
1) hydrogen atom,
2) fluorine, chlorine, bromine, iodine,
3) —(C$_1$-C$_4$)-alkyl, wherein alkyl is unsubstituted or mono-, di- or trisubstituted independently of one another by R13,
4) —(C$_1$-C$_3$)-perfluoroalkyl,
5) phenyl, wherein phenyl is unsubstituted or mono-, di- or trisubstituted independently of one another by R13,
6) —(C$_0$-C$_2$)-alkylene-O—R19, wherein R19 is
 a) hydrogen atom,
 b) —(C$_1$-C$_4$)-alkyl, wherein alkyl is unsubstituted or mono-, di- or trisubstituted independently of one another by R13, or
 c) phenyl, wherein phenyl is unsubstituted or mono-, di- or trisubstituted independently of one another by R13,
 d) —CF$_3$, or
 e) —CHF$_2$
7) —CN,
8) —NR$^{10}$—SO$_2$—R$^{10}$,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —(C$_0$-C$_2$)alkylene-C(O)—O—(C$_2$-C$_4$)-alkylene-O—C(O)—(C$_1$-C$_4$)-alkyl,
16) —C(O)—O—C(R15, R16)-O—C(O)—R17,
17) —(C$_0$-C$_2$)alkylene-C(O)—O—(C$_2$-C$_4$)-alkylene-O—C(O)—O—(C$_1$-C$_6$)-alkyl,
18) —C(O)—O—C(R15, R16)-O—C(O)—O—R17,
19) —(C$_0$-C$_3$)-alkylene-(C$_3$-C$_6$)-cycloalkyl, wherein cycloalkyl is unsubstituted or mono-, di- or trisubstituted independently of one another by R13,
20) pyridinyl, wherein pyridinyl is unsubstituted or mono-, di- or trisubstituted independently of one another by R13, 21) thiazolyl, wherein thiazolyl is unsubstituted or mono-, di- or trisubstituted independently of one another by R13,
22) —(C$_0$-C$_4$)-alkylene-(C$_3$-C$_6$)-cycloalkyl, wherein cycloalkyl is unsubstituted or mono-, di- or trisubstituted independently of one another by R13,
23) —(C$_0$-C$_3$)-alkylene-O—CH$_2$—CF$_2$—CH$_2$—O—(C$_0$-C$_3$)-alkyl,
24) —(C$_0$-C$_3$)-alkylene-O—CH$_2$—CF$_2$—CF$_2$—CH$_2$—O—(C$_0$-C$_3$)-alkyl,
25) —(C$_0$-C$_3$)-alkylene-O—CH$_2$—(C$_1$-C$_3$)-perfluoroalkylene-CH$_2$—OH, or
26) a residue from the following list

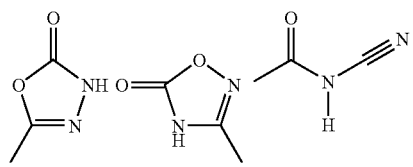

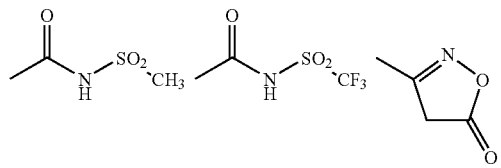

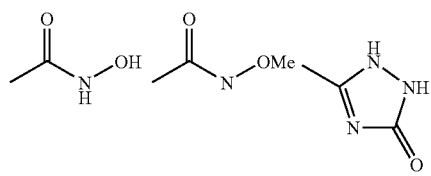

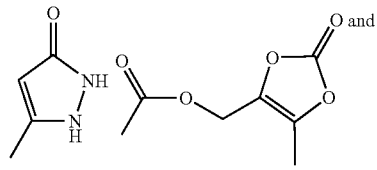

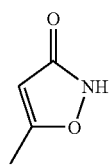

wherein Me is methyl,

R11 and R12 are independently of one another identical or different and are
1) hydrogen atom,
2) —(C$_1$-C$_4$)-alkyl, wherein alkyl is unsubstituted or mono-, di- or trisubstituted independently of one another by R13,
3) —(C$_0$-C$_6$)-alkyl-(C$_3$-C$_6$)-cycloalkyl,
4) —O—R$^{17}$, or
5) —(C$_0$-C$_6$)-alkyl-heterocyclyl, wherein alkyl and heterocyclyl independently from one another are unsubstituted or mono-, di- or trisubstituted by R13 and wherein heterocyclyl is selected out of the group azetidine, imidazolidine, morpholine, (1,4)-oxazepane or pyrrolidine or R11 and R12 together with the nitrogen atom to which they are bonded can form a ring, which is selected out of the group azetidine, imidazolidine, morpholine, (1,4)-oxazepane, 1,4-oxazepine, piperazine, piperidine, pyrrolidine or thiomorpholine, R13 is fluorine, chlorine, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_6$)-cycloalkyl, —(C$_0$-C$_3$)-alkylene-O—R$^{10}$, —Si—(CH$_3$)$_3$, —S—R$^{10}$, —SO$_2$—R$^{10}$, alkyl, —(C$_1$-C$_3$)-perfluoroalkyl, or a residue from the following list

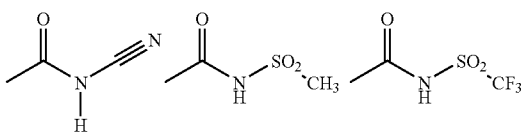

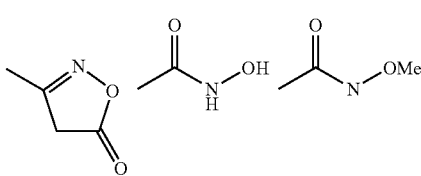

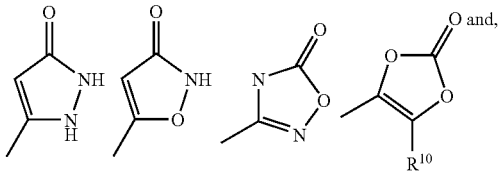

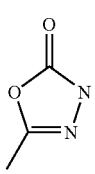

wherein Me is methyl,

R$^{10}$ and R$^{20}$ are independently of one another hydrogen, —(C$_1$-C$_4$)-alkyl or
—(C$_1$-C$_3$)-perfluoroalkyl, R$^{15}$ and R$^{16}$ are independently of one another hydrogen, —(C$_1$-C$_4$)-alkyl, or together form a ring out of the droup cyclopropyl, cyclobutyl, cyclopentyl or cyclohexyl, wherein each ring is unsubstituted or substituted one to three times by R$^{10}$, and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

The present invention also relates to the compounds of the formula Ia,

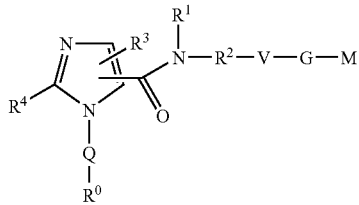

wherein $R^0$; $R^1$; $R^2$; $R^3$; $R^4$; Q; V, G and M have the meanings indicated in formula I.

The present invention also relates to the compounds of the formula Ib,

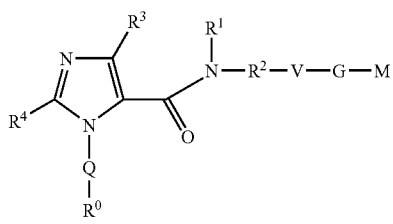

wherein $R^0$; $R^1$; $R^2$; $R^3$; $R^4$; Q; V, G and M have the meanings indicated in formula I.

The present invention also relates to the compounds of the formula Ic,

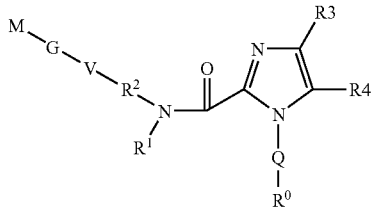

wherein $R^0$; $R^1$; $R^2$; $R^3$; $R^4$; Q; V, G and M have the meanings indicated in formula I.

The present invention also relates to the compounds of the formula Id,

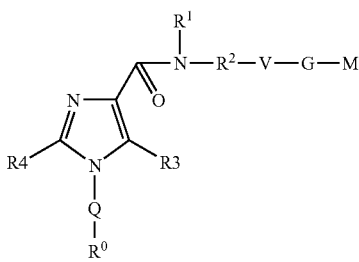

wherein $R^0$; $R^1$; $R^2$; $R^3$; $R^4$; Q; V, G and M have the meanings indicated in formula I.

DETAILED DESCRIPTION OF THE INVENTION

The present invention also relates to the compounds of the formula I, which are

3-[5-(5-Chloro-thiophen-2-yl)-isoxazol-3-ylmethyl]-3H-imidazole-4-carboxylic acid (1-isopropyl-piperidin-4-yl)-amide;

1-[5-(5-Chloro-thiophen-2-yl)-isoxazol-3-ylmethyl]-1H-imidazole-4-carboxylic acid (1-isopropyl-piperidin-4-yl)-amide;

5-Chloro-3-[5-(5-chloro-thiophen-2-yl)-isoxazol-3-ylmethyl]-2-phenyl-3H-imidazole-4-carboxylic acid (1-isopropyl-piperidin-4-yl)-amide;

3-[5-(5-Chloro-thiophen-2-yl)-isoxazol-3-ylmethyl]-5-methyl-3H-imidazole-4-carboxylic acid (1-isopropyl-piperidin-4-yl)-amide;

3-[5-(5-Chloro-thiophen-2-yl)-isoxazol-3-ylmethyl]-2-ethyl-5-methyl-3H-imidazole-4-carboxylic acid (1-isopropyl-piperidin-4-yl)-amide;

1-[5-(5-Chloro-thiophen-2-yl)-isoxazol-3-ylmethyl]-2-ethyl-5-methyl-1H-imidazole-4-carboxylic acid (1-isopropyl-piperidin-4-yl)-amide;

3-[5-(5-Chloro-thiophen-2-yl)-isoxazol-3-ylmethyl]-2-iodo-5-methyl-3H-imidazole-4-carboxylic acid (1-isopropyl-piperidin-4-yl)-amide;

1-[5-(5-Chloro-thiophen-2-yl)-isoxazol-3-ylmethyl]-2-iodo-5-methyl-1H-imidazole-4-carboxylic acid (1-isopropyl-piperidin-4-yl)-amide;

3-[5-(5-Chloro-thiophen-2-yl)-isoxazol-3-ylmethyl]-2-methoxymethyl-3H-imidazole-4-carboxylic acid (1-isopropyl-piperidin-4-yl)-amide;

1-[5-(5-Chloro-thiophen-2-yl)-isoxazol-3-ylmethyl]-2-methoxymethyl-1H-imidazole-4-carboxylic acid (1-isopropyl-piperidin-4-yl)-amide;

3-[5-(5-Chloro-thiophen-2-yl)-isoxazol-3-ylmethyl]-2-cyclopropyl-3H-imidazole-4-carboxylic acid (1-isopropyl-piperidin-4-yl)-amide;

3-[5-(5-Chloro-thiophen-2-yl)-isoxazol-3-ylmethyl]-2-(2,6-difluoro-phenyl)-3H-imidazole-4-carboxylic acid (1-isopropyl-piperidin-4-yl)-amide;

3-[5-(5-Chloro-thiophen-2-yl)-isoxazol-3-ylmethyl]-2-cyclopentyl-3H-imidazole-4-carboxylic acid (1-isopropyl-piperidin-4-yl)-amide;

3-[5-(5-Chloro-thiophen-2-yl)-isoxazol-3-ylmethyl]-2-(2-methoxy-ethyl)-3H-imidazole-4-carboxylic acid (1-isopropyl-piperidin-4-yl)-amide;

3-[5-(5-Chloro-thiophen-2-yl)-isoxazol-3-ylmethyl]-2-(2,6-dichloro-phenyl)-3H-imidazole-4-carboxylic acid (1-isopropyl-piperidin-4-yl)-amide;

3-[5-(5-Chloro-thiophen-2-yl)-isoxazol-3-ylmethyl]-2-isopropyl-3H-imidazole-4-carboxylic acid (1-isopropyl-piperidin-4-yl)-amide;

3-[5-(5-Chloro-thiophen-2-yl)-isoxazol-3-ylmethyl]-2-pyridin-2-yl-3H-imidazole-4-carboxylic acid (1-isopropyl-piperidin-4-yl)-amide;

3-[5-(5-Chloro-thiophen-2-yl)-isoxazol-3-ylmethyl]-5-methyl-2-phenyl-3H-imidazole-4-carboxylic acid (1-isopropyl-piperidin-4-yl)-amide;

1-[5-(5-Chloro-thiophen-2-yl)-isoxazol-3-ylmethyl]-5-methyl-2-phenyl-1H-imidazole-4-carboxylic acid (1-isopropyl-piperidin-4-yl)-amide;

3-[5-(5-Chloro-thiophen-2-yl)-isoxazol-3-ylmethyl]-2-pyridin-3-yl-3H-imidazole-4-carboxylic acid (1-isopropyl-piperidin-4-yl)-amide;

3-[5-(5-Chloro-thiophen-2-yl)-isoxazol-3-ylmethyl]-2-(2-methyl-thiazol-4-y)-3H-imidazole-4-carboxylic acid (1-isopropyl-piperidin-4-yl)-amide;
1-[5-(5-Chloro-thiophen-2-yl)-isoxazol-3-ylmethyl]-2-(2-methyl-thiazol-4-yl)-1H-imidazole-4-carboxylic acid (1-isopropyl-piperidin-4-yl)-amide;
3-[5-(5-Chloro-thiophen-2-yl)-isoxazol-3-ylmethyl]-2-ethanesulfonyl-3H-imidazole-4-carboxylic acid (1-isopropyl-piperidin-4-yl)-amide;
3-[5-(5-Chloro-thiophen-2-yl)-isoxazol-3-ylmethyl]-5-methyl-3H-imidazole-2,4-dicarboxylic acid 2-amide 4-[(1-isopropyl-piperidin-4-yl)-amide];
1-[5-(5-Chloro-thiophen-2-yl)-isoxazol-3-ylmethyl]-5-methyl-1H-imidazole-2,4-dicarboxylic acid 2-amide 4-[(1-isopropyl-piperidin-4-yl)-amide];
2-Bromo-3-[5-(5-chloro-thiophen-2-yl)-isoxazol-3-ylmethyl]-5-methyl-3H-imidazole-4-carboxylic acid (1-isopropyl-piperidin-4-yl)-amide;
2-Bromo-1-[5-(5-chloro-thiophen-2-yl)-isoxazol-3-ylmethyl]-5-methyl-1H-imidazole-4-carboxylic acid (1-isopropyl-piperidin-4-yl)-amide;
2-(4-Chloro-phenyl)-1-[5-(5-chloro-thiophen-2-yl)-isoxazol-3-ylmethyl]-1H-imidazole-4-carboxylic acid (1-isopropyl-piperidin-4-yl)-amide;
3-[(5-Chloro-pyridin-2-ylcarbamoyl)-methyl]-3H-imidazole-4-carboxylic acid (1-isopropyl-piperidin-4-yl)-amide;
3-[(4-Chloro-phenylcarbamoyl)-methyl]-2-methoxymethy1-3H-imidazole-4-carboxylic acid (1-isopropyl-piperidin-4-yl)-amide;
1-[(4-Chloro-phenylcarbamoyl)-methyl]-2-methoxymethyl-1H-imidazole-4-carboxylic acid (1-isopropyl-piperidin-4-yl)-amide;
1-[(5-Chloro-pyridin-2-ylcarbamoyl)-methyl]-2-ethanesulfonyl-1H-imidazole-4-carboxylic acid (1-isopropyl-piperidin-4-yl)-amide;
5-Chloro-3-[(5-chloro-pyridin-2-ylcarbamoyl)-methyl]-2-phenyl-3H-imidazole-4-carboxylic acid (1-isopropyl-piperidin-4-yl)-amide;
1-[5-(5-Chloro-thiophen-2-yl)-isoxazol-3-ylmethyl]-2-cyclopropyl-1H-imidazole-4-carboxylic acid (1-isopropyl-piperidin-4-yl)-amide;
3-[5-(5-Chloro-thiophen-2-yl)-isoxazol-3-ylmethyl]-2-(2-methoxy-phenyl)-5-methyl-3H-imidazole-4-carboxylic acid (1-isopropyl-piperidin-4-yl)-amide;
3-[5-(5-Chloro-thiophen-2-yl)-isoxazol-3-ylmethyl]-2-(3-trifluoromethyl-phenyl)-3H-imidazole-4-carboxylic acid (1-isopropyl-piperidin-4-yl)-amide;
1-[5-(5-Chloro-thiophen-2-yl)-isoxazol-3-ylmethyl]-5-(1-isopropyl-piperidin-4-ylcarbamoyl)-1H-imidazole-2-carboxylic acid ethyl ester;
1-[5-(5-Chloro-thiophen-2-yl)-isoxazol-3-ylmethyl]-2-(1-isopropyl-piperidin-4-ylcarbamoyl)-1H-imidazole-4-carboxylic acid tert-butyl ester;
1-[5-(5-Chloro-thiophen-2-yl)-isoxazol-3-ylmethyl]-2-(1-isopropyl-piperidin-4-ylcarbamoyl)-1H-imidazole-4-carboxylic acid;
1-[5-(5-Chloro-thiophen-2-yl)-isoxazol-3-ylmethyl]-2-(1-isopropyl-piperidin-4-ylcarbamoyl)-1H-imidazole-4-carboxylic acid methyl ester;
1-[5-(5-Chloro-thiophen-2-yl)-isoxazol-3-ylmethyl]-1H-imidazole-2,4-dicarboxylic acid 4-amide 2-[(1-isopropyl-piperidin-4-yl)-amide];
1-[5-(5-Chloro-thiophen-2-yl)-isoxazol-3-ylmethyl]-1H-imidazole-2,4-dicarboxylic acid 4-[(2-hydroxy-ethyl)-methyl-amide] 2-[(1-isopropyl-piperidin-4-yl)-amide];
1-[5-(5-Chloro-thiophen-2-yl)-isoxazol-3-ylmethyl]-4-(3-hydroxy-azetidine-1-carbonyl)-1H-imidazole-2-carboxylic acid (1-isopropyl-piperidin-4-yl)-amide;
1-[5-(5-Chloro-thiophen-2-yl)-isoxazol-3-ylmethyl]-1H-imidazole-2,4-dicarboxylic acid 4-dimethylamide 2-[(1-isopropyl-piperidin-4-yl)-amide];
1-[5-(5-Chloro-thiophen-2-yl)-isoxazol-3-ylmethyl]-2-(1-isopropyl-piperidin-4-ylcarbamoyl)-1H-imidazole-4-carboxylic acid cyclopropylmethyl ester;
1-[5-(5-Chloro-thiophen-2-yl)-isoxazol-3-ylmethyl]-2-(1-isopropyl-piperidin-4-ylcarbamoyl)-1H-imidazole-4-carboxylic acid tert-butoxycarbonylmethyl ester;
1-[5-(5-Chloro-thiophen-2-yl)-isoxazol-3-ylmethyl]-1H-imidazole-2,4-dicarboxylic acid 4-[(2-hydroxy-ethyl)-amide] 2-[(1-isopropyl-piperidin-4-yl)-amide];
1-[5-(5-Chloro-thiophen-2-yl)-isoxazol-3-ylmethyl]-4-(3-methoxy-azetidine-1-carbonyl)-1H-imidazole-2-carboxylic acid (1-isopropyl-piperidin-4-yl)-amide;
3-[1-[5-(5-Chloro-thiophen-2-yl)-isoxazol-3-ylmethyl]-2-(1-isopropyl-piperidin-4-ylcarbamoyl)-1H-imidazol-4-yl]-propionic acid methyl ester;
1-(3-Methoxy-benzyl)-1H-imidazole-2-carboxylic acid (1-isopropyl-piperidin-4-yl)-amide;
1-(3-Methoxy-benzyl)-1H-imidazole-2-carboxylic acid (1-isopropyl-piperidin-4-ylmethyl)-amide;
1-(3-chloro-benzyl)-1H-imidazole-2-carboxylic acid (1-isopropyl-piperidin-4-ylmethyl)-amide;
1-(3,4-Difluoro-benzyl)-1H-imidazole-2-carboxylic acid (1-isopropyl-piperidin-4-yl)-amide;
1-(3-Fluoro-benzyl)-1H-imidazole-2-carboxylic acid (1-isopropyl-piperidin-4-yl)-amide;
[1-(3-Methoxy-benzyl)-1H-imidazol-2-yl]-[4-(1-methyl-piperidin-4-yl)-piperazin-1-yl]-methanone;
1-(3-Methoxy-benzyl)-1H-imidazole-2-carboxylic acid (3,4,5,6-tetrahydro-2H-[1,4']bipyridinyl-4-ylmethyl)-amide;
1-(3-Methoxy-benzyl)-1H-imidazole-2-carboxylic acid (1-pyridin-4-yl-azetidin-3-ylmethyl)-amide;
1-(3-Methoxy-benzyl)-1H-imidazole-2-carboxylic acid (3,4,5,6-tetrahydro-2H-[1,4']bipyridinyl-4-yl)-amide;
1-(3-methoxy-benzyl)-1H-imidazole-2-carboxylic acid (1-pyridin-4-yl-azetidin-3-yl)-amide;
1-[5-(5-Chloro-thiophen-2-yl)-isoxazol-3-ylmethyl]-1H-imidazole-2-carboxylic acid (1-isopropyl-piperidin-4-yl)-amide;
1-[2-(4-Chloro-phenyl)-ethyl]-1H-imidazole-2-carboxylic acid (1-isopropyl-piperidin-4-yl)-amide;
1-[5-(5-Chloro-thiophen-2-yl)-isoxazol-3-yl methyl]-1H-imidazole-2-carboxylic acid (1-isopropyl-azetidin-3-ylmethyl)-amide;
1-[5-(5-Chloro-thiophen-2-yl)-isoxazol-3-ylmethyl]-1H-imidazole-2-carboxylic acid (3,4,5,6-tetrahydro-2H-[1,4']bipyridinyl-4-ylmethyl)-amide;
1-[5-(5-Chloro-thiophen-2-yl)-isoxazol-3-ylmethyl]-1H-imidazole-2-carboxylic acid (1-isopropyl-piperidin-4-ylmethyl)-amide;
1-[5-(5-Chloro-thiophen-2-yl)-isoxazol-3-ylmethyl]-1H-imidazole-2-carboxylic acid (3,4,5,6-tetrahydro-2H-[1,4']bipyridinyl-4-yl)-amide;
3-[5-(5-Chloro-thiophen-2-yl)-isoxazol-3-ylmethyl]-2-[2-(2-methoxy-ethoxy)-ethoxymethyl]-3H-imidazole-4-carboxylic acid (1-isopropyl-piperidin-4-yl)-amide;
1-[5-(5-Chloro-thiophen-2-yl)-isoxazol-3-ylmethyl]-2-methoxymethyl-1H-imidazole-4-carboxylic acid (2'-methanesulfonyl-biphenyl-4-yl)-amide;

3-[2-(4-Chloro-phenyl)-ethyl]-2-[2-(2-methoxy-ethoxy)-ethoxymethyl]-3H-imidazole-4-carboxylic acid (1-isopropyl-piperidin-4-yl)-amide;

3-[5-(5-Chloro-thiophen-2-yl)-isoxazol-3-ylmethyl]-2-(2-methoxy-ethoxymethyl)-3H-imidazole-4-carboxylic acid (1-isopropyl-piperidin-4-yl)-amide;

3-[(5-Chloro-pyridin-2-ylcarbamoyl)-methyl]-2-(2-methoxy-ethoxymethyl)-3H-imidazole-4-carboxylic acid (1-isopropyl-piperidin-4-yl)-amide; or 3-[5-(5-Chloro-thiophen-2-yl)-isoxazol-3-ylmethyl]-2-(perhydro-1,4-oxazepine-4-carbonyl)-3H-imidazole-4-carboxylic acid (1-isopropyl-piperidin-4-yl)-amide.

Definition of Terms

As used above, and throughout the description of the invention, the following terms, unless otherwise indicated, shall be understood to have the following meanings.

In general, the meaning of any group, residue, heteroatom, number etc., which can occur more than once in the compounds of the formula I, is independent of the meaning of this group, residue, heteroatom, number etc. in any other occurrence. All groups, residues, heteroatoms, numbers etc., which can occur more than once in the compounds of the formula I can be identical or different.

As used herein, the term "alkyl" is to be understood in the broadest sense to mean hydrocarbon residues which can be linear, i. e. straight-chain, or branched and which can be acyclic or cyclic residues or comprise any combination of acyclic and cyclic subunits. Further, the term alkyl as used herein expressly includes saturated groups as well as unsaturated groups which latter groups contain one or more, for example one, two or three, double bonds and/or triple bonds, provided that the double bonds are not located within a cyclic alkyl group in such a manner that an aromatic system results. All these statements also apply if an alkyl group occurs as a substituent on another residue, for example in an alkyloxy residue, an alkyloxycarbonyl residue or an arylalkyl residue. Examples of "—$(C_1-C_8)$-alkyl" or "—$(C_1-C_8)$-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl. The term "—$(C_0-C_6)$-alkyl" or "—$(C_0-C_8)$-alkylene" is a hydrocarbon residues containing 1, 2, 3, 4, 5, 6, 7 or 8 carbon atoms. The term "—$C_0$-alkyl" or "—$C_0$-alkylene" is a covalent bond.

"Unsaturated alkyl residues" are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl (=propargyl) or 2-butynyl. Alkyl residues can also be unsaturated when they are substituted.

Examples of —$(C_3-C_8)$-cycloalkyl cyclic alkyl residues are cycloalkyl residues containing 3, 4, 5, 6, 7 or 8 ring carbon atoms like cyclopropyl, cyclobutyl, cyclopentyl, cyclohexyl, cyloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom.

Of course, a cyclic alkyl group has to contain at least three carbon atoms, and an unsaturated alkyl group has to contain at least two carbon atoms. Thus, a group like $(C_1-C_8)$-alkyl is to be understood as comprising, among others, saturated acyclic $(C_1-C_8)$-alkyl, $(C_3-C_6)$-cycloalkyl, and unsaturated $(C_2-C_8)$-alkyl like $(C_2-C_8)$-alkenyl or $(C_2-C_8)$-alkynyl. Similarly, a group like $(C_1-C_4)$-alkyl is to be understood as comprising, among others, saturated acyclic $(C_1-C_4)$-alkyl, and unsaturated $(C_2-C_4)$-alkyl like $(C_2-C_4)$-alkenyl or $(C_2-C_4)$-alkynyl.

Unless stated otherwise, the term "alkyl" preferably comprises acyclic saturated hydro-carbon residues which have from one to six carbon atoms and which can be linear or branched. A particular group of saturated acyclic alkyl residues is formed by $(C_1-C_4)$-alkyl residues like methyl, ethyl, n-propyl, isopropyl, n-butyl, isobutyl, sec-butyl and tBu.

Unless stated otherwise, and irrespective of any specific substituents bonded to alkyl groups which are indicated in the definition of the compounds of the formula I, alkyl groups can in general be unsubstituted or substituted by one or more, for example one, two or three, identical or different substituents. Any kind of substituents present in substituted alkyl residues can be present in any desired position provided that the substitution does not lead to an unstable molecule. Examples of substituted alkyl residues are alkyl residues in which one or more, for example 1, 2 or 3, hydrogen atoms are replaced with halogen atoms, in particular fluorine atoms.

The terms "a monocyclic or bicyclic 6- to 14-membered aryl" or "—$(C_6-C_{14})$-aryl" are understood as meaning aromatic hydrocarbon radicals containing from 6 to 14 carbon atoms in the ring. Examples of —$(C_6-C_{14})$-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The terms "mono- or bicyclic 4- to 15-membered heterocyclyl" or "—$(C_4-C_{15})$-heterocyclyl" refer to heterocycles in which one or more of the 4 to 15 ring carbon atoms are replaced by heteroatoms such as nitrogen, oxygen or sulfur.

Examples are acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-ozazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

Preferred are heterocyclyls, such as benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimnidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl and 3-thienyl.

Also preferred are:

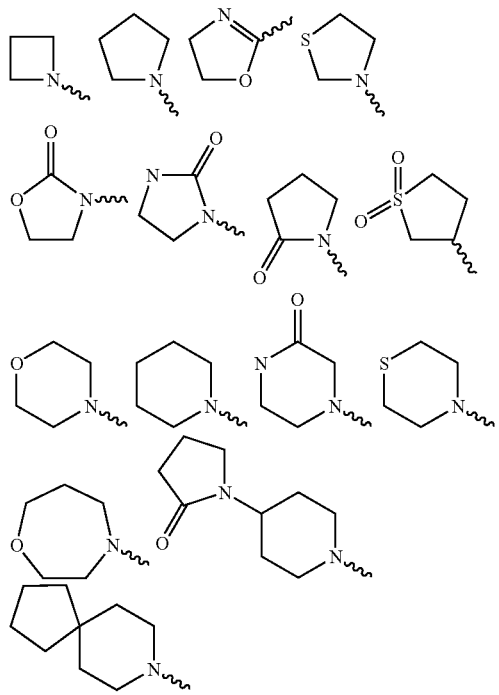

The terms "het" or "a 3- to 7-membered cyclic residue, containing up to 1, 2, 3 or 4 heteroatoms" refer to structures of heterocycles which can be derived from compounds such as azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "R$^1$—N—R$^2$—V can form a 4- to 8-membered cyclic group" or "R$^{11}$ and R$^{12}$ together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen" refer to structures of heterocycles which can be derived from compounds such as azepane, azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole.

The term "R$^{15}$ and R$^{16}$ together with the carbon atom to which they are bonded can form a 3- to 6 membered carbocyclic ring" refer to structures, which can be derived from compounds such as cyclopropyl, cyclobutyl, cyclopentyl or cyclohexyl.

The term "R$^1$ and R$^3$ together with the atoms to which they are bonded can form a 6- to 8-membered cyclic group, containing up to 1, 2, 3 or 4 heteroatoms chosen from nitrogen, sulfur or oxygen" refers to structures of heterocycles which can be derived from compounds such as azocane, azocane-2-one, cyloheptyl cyclohexyl, cyclooctane, cyclooctene, 1,4-diazepane, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,4-oxazepane, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxa-thiepane, 1,2-oxazine, 1,3-oxazine, 1,4-oxazine, [1,4]oxazocane, [1,3]oxazocan-2-one, oxocane, oxocan-2-one, phenyl, piperazine, piperidine, pyran, pyrazine, pyridazine, pyrimidine, 5,6,7,8-tetrahydro-1H-azocin-2-one or thiomorpholine.

The fact that many of the before-listed names of heterocycles are the chemical names of unsaturated or aromatic ring systems does not imply that the, the 4-15 membered mono- or polycyclic group could only be derived from the respective unsaturated ring system. The names here only serve to describe the ring system with respect to ring size and the number of the heteroatoms and their relative positions. As explained above, the 4-15 membered mono- or polycyclic group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which this group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3- oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline, 1,2,3,4-tetrahydroisoquinoline, etc.

The 4-15 membered mono- or polycyclic group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl =piperazino) or piperazin-2-yl. Indolyl can be indol-1-yl, indol-2-yl, indol-3-yl, indol-4-yl, indol-5-yl, indol-6-yl or indol-7-yl. Similarly benzimidazolyl, benzoxazolyl and benzothiazol residues can be bonded via the 2-position and via any of the positions 4, 5, 6, and 7. Quinolinyl can be quinolin-2-yl, quinolin-3-yl, quinolin-4-yl, quinolin-5-yl, quinolin-6-yl, quinolin-7-yl or quinolin-8-yl, isoqinolinyl can be isoquinol-1-yl, isoquinolin-3-yl, isoquinolin-4-yl, isoquinolin-5-yl, isoquinolin-6-yl, isoquinolin-7-yl or isoquinolin-8-yl. In addition to being bonded via any of the positions indicated for quinolinyl and isoquinolinyl, 1,2,3,4-tetrahydroquinolinyl and 1,2,3,4-tetrahydroisoquinolinyl can also be bonded via the nitrogen atoms in 1-position and 2-position, respectively.

Unless stated otherwise, and irrespective of any specific substituents bonded to the 4-15 membered mono- or polycyclic group or any other heterocyclic groups which are indicated in the definition of the compounds of the formula I, the 4-15 membered mono- or polycyclic group can be unsubstituted or substituted on ring carbon atoms with one or more, for example one, two, three, four or five, identical or different substituents like $(C_1-C_8)$-alkyl, in particular $(C_1-C_4)$-alkyl, $(C_1-C_8)$-alkyloxy, in particular $(C_1-C_4)$-alkyloxy, $(C_1-C_4)$-alkylthio, halogen, nitro, amino, $((C_1-C_4)$-alkyl)carbonylamino like acetylamino, trifluoromethyl, trifluoromethoxy, hydroxy, oxo, hydroxy-$(C_1-C_4)$-alkyl such as, for example, hydroxymethyl or 1-hydroxyethyl or 2-hydroxyethyl, methylenedioxy, ethylenedioxy, formyl, acetyl, cyano, aminosulfonyl, methylsulfonyl, hydroxycarbonyl, aminocarbonyl, $(C_1-C_4)$-alkyloxycarbonyl, optionally substituted phenyl, optionally substituted phenoxy, benzyl optionally substituted in the phenyl group, benzyloxy optionally substituted in the phenyl group, etc. The substituents can be present in any desired position provided that a stable molecule results. Of course an oxo group cannot be present in an aromatic ring. Each suitable ring nitrogen atom in the 4-15 membered mono- or polycyclic group can independently of each other be unsubstituted, i. e. carry a hydrogen atom, or can be substituted, i. e. carry a substituent like $(C_1-C_8)$-alkyl, for example $(C_1-C_4)$-alkyl such as methyl or ethyl, optionally substituted phenyl, phenyl-$(C_1-C_4)$-alkyl, for example benzyl, optionally substituted in the phenyl group, hydroxy-$(C_2-C_4)$-alkyl such as, for example 2-hydroxyethyl, acetyl or another acyl group, methylsulfonyl or another sulfonyl group, aminocarbonyl, $(C_1-C_4)$-alkyloxycarbonyl, etc. In general, in the compounds of the formula I nitrogen heterocycles can also be present as N-oxides or as quaternary salts. Ring sulfur atoms can be oxidized to the sulfoxide or to the sulfone. Thus, for example a tetrahydrothienyl residue may be present as S,S-dioxotetrahydro-thienyl residue or a thiomorpholinyl residue like thiomorpholin-4-yl may be present as 1-oxo-thiomorpholin-4-yl or 1,1-dioxo-thiomorpholin-4-yl. A substituted 4 to 15 membered mono- or polycyclic group that can be present in a specific position of the compounds of formula I can independently of other groups be substituted by substituents selected from any desired subgroup of the substituents listed before and/or in the definition of that group.

The 3-7 membered monocyclic group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl=piperazino) or piperazin-2-yl. Unless stated otherwise, and irrespective of any specific substituents bonded to the 3-7 membered monocyclic group or any other heterocyclic groups which are indicated in the definition of the compounds of the formula I, can be unsubstituted or substituted on ring carbon atoms with one or more, for example one, two, three, four or five, identical or different substituents like $(C_1-C_8)$-alkyl, in particular $(C_1-C_4)$-alkyl, $(C_1-C_8)$-alkyloxy, in particular $(C_1-C_4)$-alkyloxy, $(C_1-C_4)$-alkylthio, halogen, nitro, amino, $((C_1-C_4)$-alkyl)carbonylamino like acetylamino, trifluoromethyl, trifluoromethoxy, hydroxy, oxo, hydroxy-$(C_1-C_4)$-alkyl such as, for example, hydroxymethyl or 1-hydroxyethyl or 2-hydroxyethyl, methylenedioxy, ethylenedioxy, formyl, acetyl, cyano, aminosulfonyl, methylsulfonyl, hydroxycarbonyl, aminocarbonyl, $(C_1-C_4)$-alkyloxycarbonyl, optionally substituted phenyl, optionally substituted phenoxy, benzyl optionally substituted in the phenyl group, benzyloxy optionally substituted in the phenyl group, etc. The substituents can be present in any desired position provided that a stable molecule results. Of course an oxo group cannot be present in an aromatic ring. Each suitable ring nitrogen atom in the 3-7 membered monocyclic group can independently of each other be unsubstituted, i. e. carry a hydrogen atom, or can be substituted, i. e. carry a substituent like $(C_1-C_8)$-alkyl, for example $(C_1-C_4)$-alkyl such as methyl or ethyl, optionally substituted phenyl, phenyl-$(C_1-C_4)$-alkyl, for example benzyl, optionally substituted in the phenyl group, hydroxy-$(C_2-C_4)$-alkyl such as, for example 2-hydroxyethyl, acetyl or another acyl group, methylsulfonyl or another sulfonyl group, aminocarbonyl, $(C_1-C_4)$-alkyloxycarbonyl, etc. In general, in the compounds of the formulae I nitrogen heterocycles can also be present as N-oxides or as quaternary salts. Ring sulfur atoms can be oxidized to the sulfoxide or to the sulfone. Thus, for example a tetrahydrothienyl residue may be present as S,S-dioxotetrahydrothienyl residue or a thiomorpholinyl residue like thiomorpholin-4-yl may be present as 1-oxo-thiomorpholin-4-yl or 1,1-dioxo-thiomorpholin-4-yl. A substituted 3-7 membered monocyclic group that can be present in a specific position of the compounds of formulae I can independently of other groups be substituted by substituents selected from any desired subgroup of the substituents listed before and/or in the definition of that group.

The term "—$(C_1$-$C_3)$-perfluoroalkyl" is a partial or totally fluorinated alkyl-residue, which can be derived from residues such as —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$,
—$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$,
—$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$,
—$CF_2$—$CF_2$—$CHF_2$ or —$CF_2$—$CF_2$—$CH_2F$.

The term "—$(C_1$-$C_3)$-perfluoroalkylene" is a partial or totally fluorinated alkylene-residue, which can be derived from residues such as —$CF_2$—, —$CHF$—, —$CHF$—$CHF_2$—, —$CHF$—$CHF$—, —$CH_2$—$CF_2$—, —$CH_2$—$CHF$—, —$CF_2$—$CF_2$—, —$CF_2$—$CHF$—, —$CH_2$—$CHF$—$CF_2$—, —$CH_2$—$CHF$—$CHF$—, —$CH_2$—$CH_2$—$CF_2$—, —$CH_2$—$CH_2$—$CHF$, —$CH_2$—$CF_2$—$CF_2$—, —$CH_2$—$CF_2$—$CHF$—, —$CHF$—$CHF$—$CF_2$—, —$CHF$—$CHF$—$CHF$—, —$CHF$—$CH_2$—$CF_2$—,
—$CHF$—$CH_2$—$CHF$—, —$CHF$—$CF_2$—$CF_2$—, —$CHF$—$CF_2$—$CHF$—, —$CF_2$—$CHF$—$CF_2$—, —$CF_2$—$CHF$—$CHF$—, —$CF_2$—$CH_2$—$CF_2$—,
—$CF_2$—$CH_2$—$CHF$—, —$CF_2$—$CF_2$—$CF_2$—, or —$CF_2$—$CF_2$—$CHF$.

"Halogen" is fluorine, chlorine, bromine or iodine, preferably fluorine, chlorine or iodune, particularly preferably chlorine or iodine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

"Physiologically tolerable salts" of the compounds of formula I are nontoxic salts that are physiologically acceptable, in particular pharmaceutically utilizable salts. Such salts of compounds of the formula I containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formula I, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I, which simultaneously contain a basic group and an acidic group, for example a guanidino group and a carboxyl group, can also be present as zwitterions (betaines) which are likewise included in the present invention.

"Salts" of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts. The present invention furthermore includes all solvates of compounds of the formula I, for example hydrates or adducts with alcohols.

The invention also includes derivatives and modifications of the compounds of the formula I, for example prodrugs, protected forms and other physiologically tolerable derivatives, as well as active metabolites of the compounds of the formula I. The invention relates in particular to prodrugs and protected forms of the compounds of the formula I, which can be converted into compounds of the formula I under physiological conditions. Suitable prodrugs for the compounds of the formula I, i. e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443 which are all incorporated herein by reference. Suitable prodrugs for the compounds of the formula I are especially acyl prodrugs and carbamate prodrugs of acylatable nitrogen-containing groups such as amino groups and the guanidino group and also ester prodrugs and amide prodrugs of carboxylic acid groups which may be present in compounds of the formula I. In the acyl prodrugs and carbamate prodrugs one or more, for example one or two, hydrogen atoms on nitrogen atoms in such groups are replaced with an acyl group or a carbamate, preferably a —$(C_1$-$C_6)$-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, $(C_1$-$C_{18})$-alkyl, $(C_3$-$C_8)$-cycloalkyl, $(C_3$-$C_8)$-cycloalkyl-$(C_1$-$C_4)$-alkyl-, $(C_6$-$C_{14})$-aryl, Het-, $(C_6$-$C_{14})$-aryl-$(C_1$-$C_4)$-alkyl- or Het-$(C_1$-$C_4)$-alkyl- and in which $R^{p2}$ has the meanings indicated for $R^{p1}$ with the exception of hydrogen.

Especially preferred compounds of the formula I are those wherein two or more residues are defined as indicated before for preferred compounds of the formula I, or residues can have one or some of the specific denotations of the residues given in their general definitions or in the definitions of preferred compounds before. All possible combinations of definitions given for preferred definitions and of specific denotations of residues explicitly are a subject of the present invention.

Also with respect to all preferred compounds of the formula I all their stereoisomeric forms and mixtures thereof in any ratio and their physiologically acceptable salts explicitly are a subject of the present invention, as well as are their prodrugs. Similarly, also in all preferred compounds of the formula I, all residues that are present more than one time in the molecule are independent of each other and can be identical or different.

The compounds of the formulae I, Ia, Ib, Ic and Id can be prepared by utilising procedures and techniques, which per se are well known and appreciated by one of ordinary skill in the art. Starting materials or building blocks for use in the general synthetic procedures that can be applied in the preparation of the compounds of formulae I and Ia are readily available to one of ordinary skill in the art. In many cases they are commercially available or have been described in the literature. Otherwise they can be prepared from readily available precursor compounds analogously to procedures described in the literature, or by procedures or analogously to procedures described in this application.

In general, compounds of the formulae I, Ia, Ib, Ic and Id can be prepared, for example in the course of a convergent synthesis, by linking two or more fragments which can be derived retrosynthetically from the formulae I and Ia. More specifically, suitably substituted starting Imidazole derivatives are employed as building blocks in the preparation of the compounds of formulae I, Ia and Ib. If not commercially available, such Imidazole derivatives can be prepared according to the well-known standard procedures for the formation of the Imidazole ring system. By choosing suitable precursor molecules, these imidazole syntheses allow the introduction of a variety of substituents into the various positions of the imidazole system, which can be chemically modified in order to finally arrive at the molecule of the formulae I, Ia, Ib, Ic and Id having the desired substituent pattern. As one of the comprehensive reviews in which numerous details and literature references on the chemistry of imidazole and on synthetic procedures for their preparation can be found, M. R. Grimmett in Comprehensive Heterocyclic chemistry; Eds. A. Katritzky, Ch. Rees, E. Scriven; Elsevier 1996, Vol. 3; and K. Ebel in Houben-Weyl, "Methoden der Organischen Chemie" (Methods of Organic Chemistry), Georg Thieme Verlag, Stuttgart, Germany 1994, Vol. E8c Hetarene.

If starting imidazole derivatives are not commercially available and have to be synthesized this can be done, for example, according to the well known imidazole syntheses mentioned above. In the following procedures of particular interest for the embodiment of this invention are explained briefly, however, they are standard procedures comprehensively discussed in the literature, and are well known to one skilled in the art.

One cyclisation reaction to the imidazole core 4 starts from a 1,2-diketo fragment 2 and an aldehyde 3 in the presence of an ammonia source (K. Wenger et al., Arch. Pharm. 1974, 492; M. Brackeen et al., Tetrahedron Lett. 1994, 1635). Many variations of this reaction are well documented by K. Ebel in Houben-Weyl, "Methoden der Organischen Chemie" (Methods of Organic Chemistry), Georg Thieme Verlag, Stuttgart, Germany 1994, Vol. E8c Hetarene.

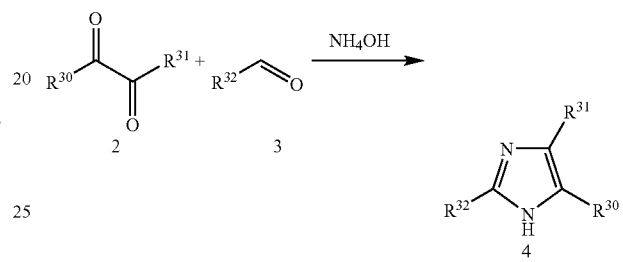

A closely related procedure is the condensation of trifluorodibromoacetone 5 with a wide variety of aldehydes 6 in the presence of ammonia to the corresponding imidazoles 7 (Matthews et al., J. Med. Chem. 1990, 317; J. J. Baldwin et al., J. Med. Chem. 1979, 687; J. J. Baldwin et al., J. Med. Chem. 1975, 895).

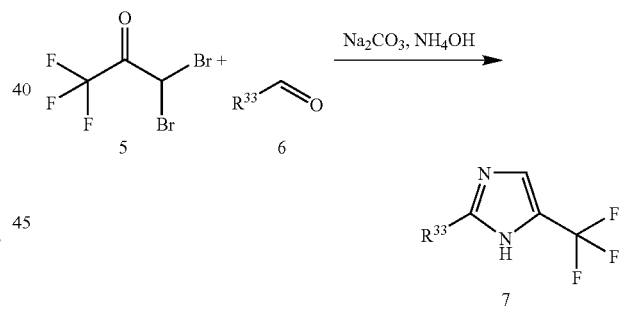

This reaction leads to 4-trifluoroimidazole derivatives 7, which then, after being optionally derivatised, can be easily converted into a carboxylic acid or carboxylic ester.

Another method involves the reaction of a α-haloketone (X=Cl, Br) 8 or α-hydroxyketone 8 (X=OH) and an amidine 9 to the corresponding imidazole 10 (J. J. Baldwin et al., J. Med. Chem. 1986, 1065; G. Kempter et al., J. Prakt. Chem. 1971, 977).

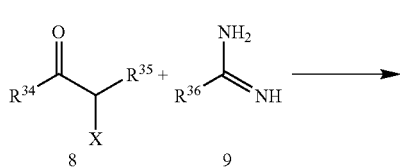

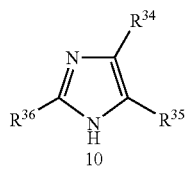

Furthermore 4-carboxyimidazoles 13 can also built up starting from the imidate 12 and and amino-β-ketoester 11. (D. Judd et al., J. Med. Chem. 1994, 3108).

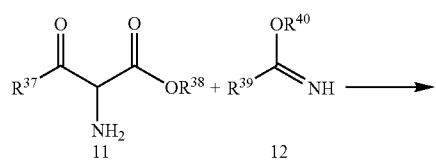

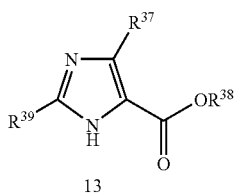

Following a procedure from A. Veronese et al., Synthesis 1985, 300; A. Veronese et al.; J. Heterocyclic. Chem. 1980, 1723, and Raghu et al., U.S. Pat. No. 4,395,547 utilising hydroxyimino-β-ketoesters 14 and activated primary amines 15 (R$^{43}$=H) or α-aminoacids 15 (R$^{43}$=COOH) a wide variety of 4-carboxyimidazoles 16 can be synthesised.

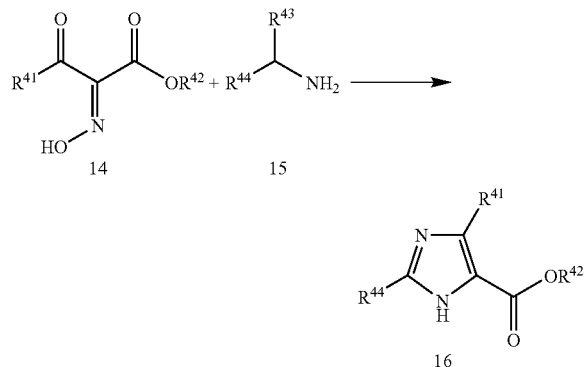

Synthetic access to 4-carboxyimidazoles 19 can also advantageously archieved for example by following a procedure described by N. Heindel et al., Tetrahedron Lett. 1971, 1439 and R. Paul et al., J. Med. Chem. 1985, 1704.

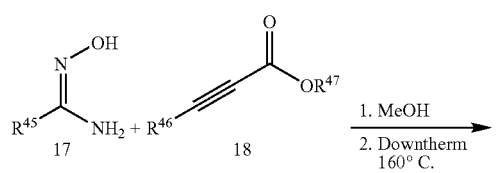

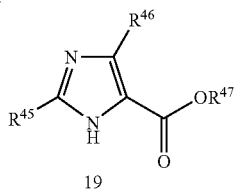

Condensation of the hydroxyamidine 17 with a propynic ester 18 derivative leads after rearrangement and pyrolytic elimination to the desired carboxy imidazoles 19.

Starting form the imidate 21, readily available from the corresponding nitrile, a wide range of imidazoles 22 is accessible after reaction with 1,3- dihydroxyacetone 20 (S. Shilcrat et al., J. Org. Chem. 1997, 8449).

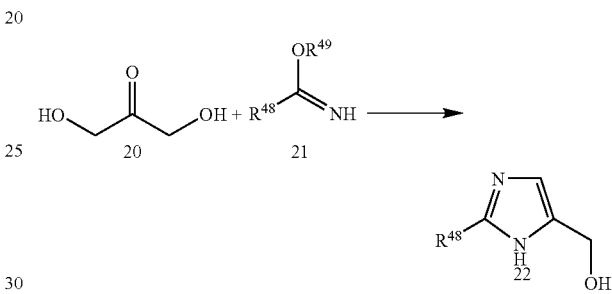

Analogously reaction of amidine 24 with bromoenolether 23 leads to formylimidazoles 25 of type (S. Shilcrat et al., J. Org. Chem. 1997, 8449)

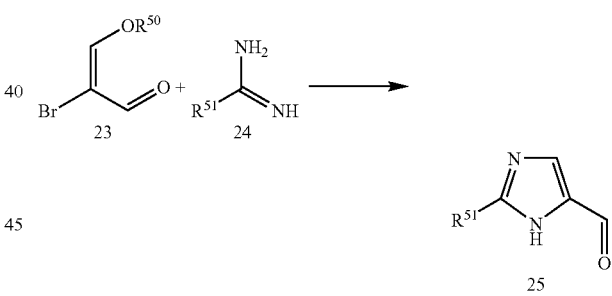

The hydroxymethyl group of 22 as well as the formyl group of 25 can optionally be transformed to a variety of functional groups, for example, by oxidation to the corresponding carboxylic acid or carboxylic ester.

Condensation of ethylthioiminoacetate 26 with α-aminoketones 27 is also a valuable pathway to built up the carboxyimidazoles 28 core (H. Yamanaka et al., Chem. Pharm. Bull. 1983, 31, 4549 and S. Mignani et al., Bioorg. Med. Chem. Lett. 2001, 11, 127).

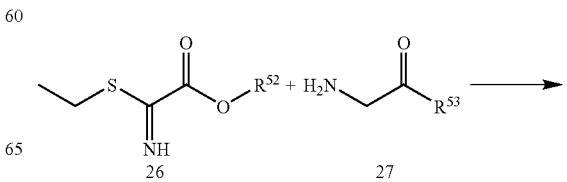

28

Depending on the substituents in the starting materials, in certain imidazole syntheses mixtures of positional isomers may be obtained, which, however, can be separated by modern separation techniques like, for example, preparative HPLC.

Further, in order to obtain the desired substituents at the imidazole ring system in the formulae I, Ia and Ib, the functional groups introduced into the ring system during the imidazole synthesis can be chemically modified. Especially the groups present in the imidazole ring system can be modified by a variety of reactions and thus the desired residues $R^{1a}$, $R^{1b}$ be obtained. For example, an imidazole carrying a hydrogen atom in the 2-position can also be obtained by saponification and subsequent decarboxylation of imidazole carrying an ester group in the respective position. Carboxylic acid groups and acetic acid groups in the 2-position, the 4-position and the 5-position can be converted into their homologues by usual reactions for chain elongation of carboxylic acids. Halogen atoms can be introduced into the 2-position, the 4-position and the 5-position, for example according to procedures described in the literature like the following. For the fluorination of imidazoles N-fluoro-2,4,6-trimethylpyridinium triflate is the reagent of choice (T. Umemoto, S. Fukami, G. Tomizawa, K. Harasawa, K. Kawada, K. Tomita, J. Am. Chem. Soc. 1990, 112, 8563) but is not limited to this reagent. The chlorination, bromination, or iodination of imidazoles can be accomplished by the reaction of the elemental halogens or by the use of NCS, NBS or NIS and many other reagents well known to those skilled in the art. This procedures are for example referred in Y. Shi et al., Synth. Commun. 1993, 23, 2623;H. Rapoport et al., Synthesis 1988, 767; R. Jones et al., J. Org. Chem. 1999, 64, 6575; J. Sessler et al., Chem. Eur. J. 2001, 7, 721. Depending on the reaction conditions, reagent, stochiometry and substitution pattern the halogen is introduced in the 2-position and/or 4-position and/or 5-position. By selective halogen/metal exchange or metalation by selective hydrogen/metal exchange and subsequent reaction with a wide range of electrophiles various substituents can be introduced at the heterocyclic nucleus. (R. Breslow et al., J. Am. Chem. Soc. 1983, 105, 5337; P. Knochel et al., J. Org. Chem. 2000, 65, 4618; S. Ohta et al., Chem. Pharm. Bull. 1996, 44, 1831).

Halogens or hydroxy groups—via the triflate or nonaflate—or primary amines—via its diazonium salt—or after interconversion to the corresponding stannane, or boronic acid—present in the imidazole structure can be converted into a variety of other functional groups like for example —CN, —$CF_3$, —$C_2F_5$, ethers, acids, amides, amines, alkyl- or aryl-groups mediated by means of transition metals, namely palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Orga-nomet. Chem. 1999, 576, 125; T. Sakamoto, K. Ohsawa, J. Chem. Soc. Perkin Trans I, 1999, 2323; D. Nichols, S. Frescas, D. Marona-Lewicka, X. Huang, B. Roth, G. Gudelsky, J. Nash, J. Med. Chem, 1994, 37, 4347; P. Lam, C. Clark, S. Saubern, J. Adams, M. Winters, D. Chan, A. Combs, Tetrahedron Lett., 1998, 39, 2941; D. Chan, K. Monaco, R. Wang, M. Winters, Tetrahedron Lett. 1998, 39, 2933; V. Farina, V. Krishnamurthy, W. Scott, The Stille Reaction, Wiley, 1994; F. Qing et al. J. Chem. Soc. Perkin Trans. I 1997, 3053; S. Buchwald et al. J. Am. Chem Soc. 2001, 123, 7727; S. Kang et al. Synlett 2002, 3, 427; S. Buchwald et al. Organic Lett. 2002, 4, 581; T. Fuchikami et al. Tetrahedron Lett. 1991, 32, 91; Q. Chen et al. Tetrahedron Lett. 1991, 32, 7689).

For example, nitro groups can be reduced to amino group with various reducing agents, such as sulfides, dithionites, complex hydrides or by catalytic hydrogenation. A reduction of a nitro group may also be carried out at a later stage of the synthesis of a compound of the formulae I and Ia, and a reduction of a nitro group to an amino group may also occur simultaneously with a reaction performed on another functional group, for example when reacting a group like a cyano group with hydrogen sulfide or when hydrogenating a group. In order to introduce the residues $R^{1a}$, $R^{1b}$, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups present in the imidazole nucleus can be hydrolyzed to the corresponding carboxylic acids, which after activation can then be reacted with amines or alcohols under standard conditions. Ether groups present at the imidazole nucleus, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

During the course of the synthesis in order to modify the groups $R^{55}$ or $R^{8'}$ attached to the imidazole ring system by application of parallel synthesis methodology, beside a variety of reactions, palladium, nickel or copper catalysis can be extremely useful. Such reactions are described for example in F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999,576, 125; P. Lam, C. Clark, S. Saubern, J. Adams, M. Winters, D. Chan, A. Combs, Tetrahedron Lett. 1998, 39, 2941; D. Chan, K. Monaco, R. Wang, M. Winters, Tetrahedron Lett. 1998, 39, 2933; J. Wolfe, H. Tomori, J. Sadight, J. Yin, S. Buchwald, J. Org. Chem. 2000, 65, 1158; V. Farina, V. Krishnamurthy, W. Scott, The Stille Reaction, Wiley, 1994; S. Buchwald et al., J. Am. Chem Soc. 2001, 123, 7727; S. Kang et al., Synlett 2002, 3, 427; S. Buchwald et al., Org. Lett. 2002, 4,581.

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991; A. Katritzky, C. Rees, E. Scriven Comprehensive Heterocyclic Chemistry II, Elsevier Science, 1996) in which details on the reactions and primary source literature can be found. Due to the fact that in the present case the functional groups are attached to an imidazole ring it may in certain cases become necessary to specifically adapt reaction conditions or to choose specific reagents from a variety of reagents that can in principle be employed in a conversion reaction, or otherwise to take specific measures for achieving a desired conversion, for example to use protection group techniques. However, finding out suitable reaction variants and reaction conditions in such cases does not cause any problems for one skilled in the art.

The structural elements present in the residues in the 1-position of the imidazole ring in the compounds of the formulae I and Ia and in the $COR^8$ group present in the 4-position and/or in the 5-position of the imidazole ring can be introduced into the starting imidazole derivative obtainable as outlined above by consecutive reaction steps using parallel synthesis methodologies like those outlined below using procedures which per se are well known to one skilled in the art.

The residues $R^{8'}$ that can be introduced in formula 29, for example, by condensing a corresponding carboxylic acid of the formula 29 with a compound of the formula $HR^{8'}$, i. e. with an amine of the formula $HN(R^{1'})R^{2't}$—V-G-M to give a compound of the formula 30. The compound of the formula 30 thus obtained can already contain the desired final groups, i. e. the groups $R^{8'}$ and $R^{55}$ can be the groups $-N(R^1)-R^2$-V-G-M and $R^0$-Q- as defined in the formulae I and Ia, or optionally in the compound of the formula 30 thus obtained subsequently the residue or the residues $R^{8'}$ and the residue $R^{55}$ are converted into the residues $-N(R^1)R^2$—V-G-M and $R^0$-Q-, respectively, to give the desired compound of the formulae I and Ia.

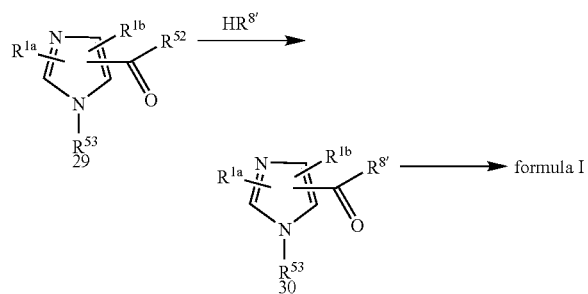

Thus, the residues $R^{8'}$ and the residues $R^{1'}$ and $R^{2't}$—V-G-M contained therein can have the denotations of $R^1$ and $R^2$—V-G-M, respectively, given above or in addition in the residues $R^{1'}$ and $R^{2't}$—V-G-M functional groups can also be present in the form of groups that can subsequently be transformed into the final groups $R^1$ and $R^2$—V-G-M, i.e. functional groups can be present in the form of precursor groups or of derivatives, for example in protected form. In the course of the preparation of the compounds of the formulae I and Ia it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). As examples of precursor groups cyano groups and nitro groups may be mentioned. The cyano groups can in a later step be transformed into carboxylic acid derivatives or by reduction into aminomethyl groups, or the nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000). For example, a phenolic hydroxy group can be attached to a trityl-polystyrene resin, which serves as a protecting group, and the molecule is cleaved from this resin by treatment with TFA at a later stage of the synthesis.

The residue $R^{55}$ in the compounds of the formulae 29 and 30 can denote the group -Q-$R^0$ as defined above which finally is to be present in the desired target molecule of the formulae I and Ia, or it can denote a group which can subsequently be transformed into the group -Q-$R^0$, for example a precursor group or a derivative of the group -Q-$R^0$ in which functional groups are present in protected form, or $R^{55}$ can denote a hydrogen atom or a protective group for the nitrogen atom of the imidazole ring. Similarly, the residues $R^{1e}$, $R^{1a}$ and $R^{1b}$ in the formulae 29 and 30 have the corresponding definitions of $R^4$, and $R^3$ in formulae I and Ia as defined above, however, for the synthesis of the compounds of the formulae I and Ia these residues, too, can in principle be present at the stage of the condensation of a compound of the formula 29 with a compound of the formula $HR^{8'}$ giving a compound of the formula 30 in the form of precursor groups or in protected form.

The residues $R^{54}$ in the compounds of the formula 29 which can be identical or different, can be, for example, hydroxy or ($C_1$-$C_4$)-alkoxy, i. e., the groups $COR^{54}$ present in the compounds of the formula 29 can be, for example, the free carboxylic acids or esters thereof like alkyl esters as can be the groups $COR^{8'}$ in the compounds of the formulae I and Ia. The groups $COR^{54}$ can also be any other activated derivative of a carboxylic acid which allows amide formation, ester formation or thioester formation with a compound of the formula $HR^{8'}$. The group $COR^{54}$ can be, for example, an acid chloride, an activated ester like a substituted phenyl ester, an azolide like an imidazolide, an azide or a mixed anhydride, for example a mixed anhydride with a carbonic acid ester or with a sulfonic acid, which derivatives can all be prepared from the carboxylic acid by standard procedures and can be reacted with an amine, an alcohol or a mercaptan of the formula $HR^{8'}$ under standard conditions. A carboxylic acid group COOH representing COR54 in a compound of the formula 29 can be obtained, for example, from an ester group introduced into the imidazole system during an imidazole synthesis by standard hydrolysis procedures.

Compounds of the formulae I and Ia in which a group $COR^{8'}$ is an ester group can also be prepared from compounds of the formula 29 in which $COR^{54}$ is a carboxylic acid group by common esterification reactions like, for example, reacting the acid with an alcohol under acid catalysis, or alkylation of a salt of the carboxylic acid with an electrophile like an alkyl halogenide, or by transesterification from another ester. Compounds of the formulae I and Ia in which a group $COR^{8'}$ is an amide group can be prepared from amines and compounds of the formula 29 in which COR54 is a carboxylic acid group or an ester thereof by common amination reactions. Especially for the preparation of amides the compounds of the formula 29 in which COR54 is a carboxylic acid group can be condensed under standard conditions with compounds of the formula $HR^{8'}$ which are amines by means of common coupling reagents used in peptide synthesis. Such coupling reagents are, for example, carbodiimides like dicyclohexylcarbodiimide (DCC) or diisopropylcarbodiimide, carbonyldiazoles like carbonyldiimidazole (CDI) and similar reagents, propylphosphonic anhydride, O-((cyano-(ethoxycarbonyl)-methylene)amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP—Cl) and many others.

If the residue $-Q-R^0$ present in an imidazole of the formulae I and Ia or the residue $R^{55}$ present in an imidazole of the formula 29, or a residue in which functional groups within the residue $-Q-R^0$ or $R^{55}$ are present in protected form or in the form of a precursor group, have not already been introduced during a preceding step, for example during a synthesis of the imidazole nucleus, these residues can, for example, be introduced into the 1-position of the imidazole system by conventional literature procedures well known to one skilled in the art for N-alkylation, reductive amination, N-arylation, N-acylation or N-sulfonylation of ring nitrogen atoms of heterocycles. The starting imidazole derivative that is to be employed in such a reaction carries a hydrogen atom in the 1-position. N-Alkylation of a ring nitrogen atom can, for example, be performed under standard conditions, preferably in the presence of a base like $K_2CO_3$, $Cs_2CO_3$, NaH or $KO^tBu$, using an alkylating compound of the formula $LG-Q-R^0$ or of the formula $R^{55}$-LG, wherein the atom in the group Q or in the group $R^{55}$ bonded to the group LG in this case is an aliphatic carbon atom of an alkyl moiety and LG is a leaving group, for example halogen like chlorine, bromine or iodine, or a sulfonyloxy group like tosyloxy, mesyloxy or trifluormethylsulfonyloxy. LG may, for example, also be a hydroxy group which, in order to achieve the alkylation reaction, is activated by a conventional activating agent. The regioselectivity of the N-alkylation can be controlled by the choice of the base, solvent and reaction conditions as for example described by M. Pierce et al., J. Org. Chem. 1993, 58, 4642. Alternatively, a protective group strategy, like for example described by F. Guibe et al., Tetrahedron Lett. 1997, 35, 12525; B. Kim et al., Tetrahedron Lett. 2000, 41, 10031; N. Anthony et al., J. Med. Chem. 1999, 42, 3356 may be useful in order to obtain one regioisomer selectively. Nevertheless mixtures of positional isomers, can be separated by modern separation techniques like, for example, preparative HPLC.

For the preparation of compounds in which A is a direct linkage and an aromatic group is directly bonded to the 1-position of the imidazole system, conventional arylation procedures can be used. For example aryl fluorides like alkyl fluorobenzoates or 4-fluorophenyl methyl sulfones can be employed as arylating agents. Such processes are described, for example, by M. Yamada et al. J. Med. Chem. 1996, 39, 596; J. Ohmori et al. J. Med. Chem. 1996, 39, 3971. Alternatively a wide variety of substituted aryl iodides, aryl bromides or aryl triflates can serve as arylating agents at the 1-position of the heterocyclic nitrogen in a copper salt or palladium mediated reaction according for example to P. Cozzi et al. Farmaco 1987, 42, 205; P. Unangst, D. Connor, R. Stabler, R. Weikert, J. Heterocycl. Chem. 1987, 24, 811; G. Tokmakov, I. Grandberg, Tetrahedron 1995, 51, 2091; D. Old, M. Harris, S. Buchwald, Org. Lett. 2000, 2, 1403, G. Mann, J. Hartwig, M. Driver, C. Fernandez-Rivas, J. Am. Chem. Soc. 1998, 120, 827; J. Hartwig, M. Kawatsura, S. Hauk, K. Shaughnessy, L. J. Org. Chem. 1999, 64, 5575; S. Buchwald et al., J. Am. Chem. Soc. 2001, 123, 7727. Moreover such arylations can also be accomplished by reaction of a wide range of substituted aryl boronic acids as demonstrated for example by W. Mederski, M. Lefort, M. Germann, D. Kux, Tetrahedron 1999, 55, 12757; J. Collman et al., J. Org. Chem. 2001, 66, 7892.

Preferred methods include, but are not limited to those described in the examples.

The compounds of the present invention are serine protease inhibitors, which inhibit the activity of the blood coagulation enzyme factors Xa and/or factor VIIa. In particular, they are highly active inhibitors of factor Xa. They are specific serine protease inhibitors inasmuch as they do not substantially inhibit the activity of other proteases whose inhibition is not desired. The activity of the compounds of the formulae I, Ia, Ib, Ic and Id can be determined, for example, in the assays described below or in other assays known to those skilled in the art. With respect to factor Xa inhibition, a preferred embodiment of the invention comprises compounds which have a Ki<1 mM for factor Xa inhibition as determined in the assay described below, with or without concomitant factor VIIa inhibition, and which preferably do not substantially inhibit the activity of other proteases involved in coagulation and fibrinolysis whose inhibition is not desired (using the same concentration of the inhibitor). The compounds of the invention inhibit factor Xa catalytic activity either directly, within the prothrombinase complex or as a soluble subunit, or indirectly, by inhibiting the assembly of factor Xa into the prothrombinase complex.

As inhibitors of factor Xa and/or factor VIIa the compounds of the formulae I, Ia, Ib, Ic and Id and their physiologically tolerable salts and their prodrugs are generally suitable for the therapy and prophylaxis of conditions in which the activity of factor Xa and/or factor VIIa plays a role or has an undesired extent, or which can favorably be influenced by inhibiting factor Xa and/or factor VIIa or decreasing their activities, or for the prevention, alleviation or cure of which an inhibition of factor Xa and/or factor VIIa or a decrease in their activity is desired by the physician. As inhibition of factor Xa and/or factor VIIa influences blood coagulation and fibrinolysis, the compounds of the formulae I, Ia, Ib, Ic and Id and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus are the reduction or inhibition of unwanted blood clotting, in particular in an individual, by administering an effective amount of a compound I or a physiologically tolerable salt or a prodrug thereof, as well as pharmaceutical preparations therefor.

The present invention also relates to the compounds of the formulae I, Ia, Ib, Ic and Id and/or their physiologically tolerable salts and/or their prodrugs for use as pharmaceuticals (or medicaments), to the use of the compounds of the formulae I, Ia, Ib, Ic and Id and/or their physiologically tolerable salts and/or their prodrugs for the production of pharmaceuticals for inhibition of factor Xa and/or factor VIIa or for influencing blood coagulation, inflammatory response or fibrinolysis or for the therapy or prophylaxis of the diseases mentioned above or below, for example for the production of pharmaceuticals for the therapy and prophylaxis of cardiovascular disorders, thromboembolic diseases or restenoses. The invention also relates to the use of the compounds of the formulae I, Ia, Ib, Ic and Id and/or their physiologically tolerable salts and/or their prodrugs for the inhibition of factor Xa and/or factor VIIa or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formulae I, Ia, Ib, Ic and Id and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer. The compounds of the present invention can also be used to reduce an inflammatory response. Examples of specific disorders for the treatment or prophylaxis of which the compounds of the formulae I, Ia, Ib, Ic and Id can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

The compounds of the formulae I, Ia, Ib, Ic and Id and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formulae I, Ia, Ib, Ic and Id and/or its (their) physiologically tolerable salts and/or its (their) prodrugs. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formulae I, Ia, Ib, Ic and Id and/or their physiologically tolerable salts and/or their prodrugs. The amount of the active ingredient of the formulae I, Ia, Ib, Ic and Id and/or its physiologically tolerable salts and/or its prodrugs in the pharmaceutical preparations normally is from about 0.5 mg to about 1000 mg, preferably from about 1 mg to about 500 mg.

In addition to the active ingredients of the formulae I, Ia, Ib, Ic and Id and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formulae I, Ia, Ib, Ic and Id, and/or their physiologically tolerable salts and/or their prodrugs. In case a pharmaceutical preparation contains two or more compounds of the formulae I, Ia, Ib, Ic and Id, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formulae I, Ia, Ib, Ic and Id allows a great deal of control over the biological and physico-chemical properties of the compounds and thus allows the selection of such desired compounds. Furthermore, in addition to at least one compound of the formulae I, Ia, Ib, Ic and Id and/or a physiologically tolerable salt and/or its prodrug, the pharmaceutical preparations can also contain one or more other therapeutically or prophylactically active ingredients.

When using the compounds of the formulae I, Ia, Ib, Ic and Id the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 10 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formulae I, Ia, Ib, Ic and Id can also advantageously be used as an anticoagulant outside an individual. For example, an effective amount of a compound of the invention can be contacted with a freshly drawn blood sample to prevent coagulation of the blood sample. Further, a compound of the formulae I, Ia, Ib, Ic and Id or its salts can be used for diagnostic purposes, for example in in vitro diagnoses, and as an auxiliary in biochemical investigations. For example, a compound of the formulae I, Ia, Ib, Ic and Id can be used in an assay to identify the presence of factor Xa and/or factor VIIa or to isolate factor Xa and/or factor VIIa in a substantially purified form. A compound of the invention can be labeled with, for example, a radioisotope, and the labeled compound bound to factor Xa and/or factor VIIa is then detected using a routine method useful for detecting the particular label. Thus, a compound of the formulae I, Ia, Ib, Ic and Id or a salt thereof can be used as a probe to detect the location or amount of factor Xa and/or factor VIIa activity in vivo, in vitro or ex vivo.

Furthermore, the compounds of the formulae I, Ia, Ib, Ic and Id can be used as synthesis intermediates for the preparation of other compounds, in particular of other pharmaceutical active ingredients, which are obtainable from the compounds of the formulae I, Ia, Ib, Ic and Id, for example by introduction of substituents or modification of functional groups.

The general synthetic sequences for preparing the compounds useful in the present invention our outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid or acetic acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

Abbreviations Used:
As used throughout the description of the invention, the following terms, unless otherwise indicated, shall be understood to have the following meanings.
tert-Butyl tBu
2,2'-bis(diphenylphoshino-1,1'-binaphthyl Binap
Bis-(oxo-3-oxazolidinyl)-phosphoryl chloride BOP—Cl
dibenzylidenacetone dba
Dichloromethane DCM
Diethylphosphoryl cyanide DEPC
4-Dimethyaminopyridine DMAP
N,N-Dimethylformamide DMF
Dimethylsulfoxide DMSO
1,1'-Bis(diphenylphosphino)ferrocene DPPF
O-(7-Azabenzotriazol-1-yl)-N,N,N',N'-tetramethyluronium-hexafluorophosphate HATU
N-Bromosuccinimide NBS
N-Chlorosuccinimide NCS
N-Iodosuccinimide NIS
N-Ethylmorpholine NEM
Methanol MeOH
Room temperature 20° C. to 25° C. RT
Saturated sat.
Tetrahydrofuran THF
Trifluoroacetic acid TFA
O-((Ethoxycarbonyl)cyanomethyleneamino)-N,N,N',N'-tetramethyluronium tetrafluoroborate TOTU Example 1

3-[5-(5-Chloro-thiophen-2-yl)-isoxazol-3-ylmethyl]-3H-imidazole-4-carboxylic acid (1-isopropyl-piperidin-4-yl)-amide (i) (1-Isopropyl-piperidin-4-yl)-carbamic acid tert-butyl ester To a solution of 5.0 g Piperidin-4-yl-carbamic acid tert-butyl ester in 15 ml methanol 7.34 ml acetone, 3.14 g Na(CN)BH$_3$ and 0.3 ml acetic acid were added. After stirring for 16 h at RT the solvent was removed under reduced and the residue was partitioned between 30 ml of water and 30 ml ethylacetate. The organic layer was washed with saturated Na$_2$CO$_3$ solution, water and then dried over Na$_2$SO$_4$. The solvent was removed under reduced pressure and yields a white solid.
Yield: 4.8 g MS (ES$^+$): m/e=243.

(ii) 1-Isopropyl-piperidin-4-ylamine

To 4.8 g (1-Isopropyl-piperidin-4-yl)-carbamic acid tert-butyl ester in 15 ml methanol, 20 ml methanolic hydrochloric acid (8M) was added and the mixture was stirred for 16 h. Removal of the solvent under reduced pressure yields a white solid, which was coevaporated twicely with 20 ml toluene. The product was obtained as its hydrochloride.
Yield: 5.42 g MS (ES$^+$): m/e=143.

(iv) 3-[5-(5-Chloro-thiophen-2-yl)-isoxazol-3-ylmethyl]-3H-imidazole-4-carboxylic acid methyl ester To a solution of 250 mg 3H-Imidazole-4-carboxylic acid methyl ester in 2 ml DMF 273 mg potassium carbonate and 607 mg 3-Bromomethyl-5-(5-chloro-thiophen-2-yl)-isoxazole [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (2001), 460 pp. WO 0107436 A2] were added and the mixture was stirred for 2 h at RT. After addition of 5 ml water the mixture was filtered through a chem elut® cartridge by elution with ethyl acetate and then concentrated under reduced pressure. The residue was directly subjected to the subsequent saponification reaction without further purification. Yield: 288 mg (v) 3-[5-(5-Chloro-thiophen-2-yl)-isoxazol-3-ylmethyl]-3H-imidazole-4-carboxylic acid To a solution of 720 mg 3-[5-(5-Chloro-thiophen-2-yl)-isoxazol-3-ylmethyl]-3H-imidazole-4-carboxylic acid methyl ester in 10 ml THF and 3 ml water, 57.0 mg lithium hydroxide monohydrate were added. After stirring for 2 h at 60° C. the reaction was cooled to RT. The mixture was acidified with half concentrated hydrochloric acid and the precipitate collected by filtration and washed with 3 ml water. The product was obtained as a white solid which was dried under reduced pressure. Yield: 650 mg (vi) 3-[5-(5-Chloro-thiophen-2-yl)-isoxazol-3-ylmethyl]-3H-imidazole-4-carboxylic acid (1-isopropyl-piperidin-4-yl)-amide To a solution of 650 mg 3-[5-(5-Chloro-thiophen-2-yl)-isoxazol-3-ylmethyl]-3H-imidazole-4-carboxylic acid, 1.1 ml N-NEM in 2 ml DCM, 0.7 g TOTU were added and the mixture was stirred for 30 min at RT. Then 0.7 g 1-Isopropyl-piperidin-4-ylamine hydrochloride were added and the reaction was further stirred for 2 h. After addition of 2 ml sat. $NaHCO_3$ the mixture was filtered through a chem elut® cartridge by elution with ethyl acetate and then concentrated under reduced pressure. After removal of the solvent under reduced pressure the residue was purified by preparative HPLC (C18 reverse phase column, elution with a $H_2O$/MeCN gradient with 0.1% TFA). The fractions containing the product were evaporated and lyophilized to yield a white solid. The product was obtained as its trifluoroacetate salt. Yield: 74 mg; MS (ES$^+$): m/e=434, chloro pattern Example 2

1-[5-(5-Chloro-thiophen-2-yl)-isoxazol-3-ylmethyl]-1H-imidazole-4-carboxylic acid (1-isopropyl-piperidin-4-yl)-amide This compound was isolated as a by-product in example 2. MS (ES$^+$): m/e=434, chloro pattern.

Example 3

5-Chloro-3-[5-(5-chloro-thiophen-2-yl)-isoxazol-3-ylmethyl]-2-phenyl-3H-imidazole-4-carboxylic acid (1-isopropyl-piperidin-4-yl)-amide The title compound was prepared analogously to example 1 with the difference that 5-Chloro-2-phenyl-3H-imidazole-4-carboxylic acid methyl ester was used instead of 3H-Imidazole-4-carboxylic acid methyl ester. MS (ES$^+$): m/e=544, chloro pattern.

Example 4

3-[5-(5-Chloro-thiophen-2-yl)-isoxazol-3-ylmethyl]-5-methyl-3H-imidazole-4-carboxylic acid (1-isopropyl-piperidin-4-yl)-amide The title compound was prepared analogously to example 1 with the difference that 5-Methyl-3H-imidazole-4-carboxylic acid methyl ester was used instead of 3H-Imidazole-4-carboxylic acid methyl ester. MS (ESI+): m/e=448, chloro pattern.

Example 5

3-[5-(5-Chloro-thiophen-2-yl)-isoxazol-3-ylmethyl]-2-ethyl-5-methyl-3H-imidazole-4-carboxylic acid (1-isopropyl-piperidin-4-yl)-amide The title compound was prepared analogously to example 1 with the difference that 2-Ethyl-5-methyl-3H-imidazole-4-carboxylic acid methyl ester was used instead of 3H-Imidazole-4-carboxylic acid methyl ester. MS (ES$^+$): m/e=476, chloro pattern.

Example 6

1-[5-(5-Chloro-thiophen-2-yl)-isoxazol-3-ylmethyl]-2-ethyl-5-methyl-1H-imidazole-4-carboxylic acid (1-isopropyl-piperidin-4-yl)-amide This compound was isolated as a by-product in example 5. MS (ES$^+$): m/e=476, chloro pattern Example 7

3-[5-(5-Chloro-thiophen-2-yl)-isoxazol-3-ylmethyl]-2-iodo-5-methyl-3H-imidazole-4-carboxylic acid (1-isopropyl-piperidin-4-yl)-amide (i) 2-Iodo-5-methyl-3H-imidazole-4-carboxylic acid ethyl ester A solution of 5 g 5-Methyl-3H-imidazole-4-carboxylic acid ethyl ester and 7.2 g NIS in 50 ml THF were refluxed for 10 h. After cooling, the solvent was removed under reduced pressure and the residue taken-up in ethyl acetate, washed with sat. $NaS_2O_3$ solution and dried over $MgSO_4$. After removal of the solvent under reduced pressure the product was purified by recrystallisation from ethyl acetate. Yield: 7 g (ii) 3-[5-(5-Chloro-thiophen-2-yl)-isoxazol-3-ylmethyl]-2-iodo-5-methyl-3H-imidazole-4-carboxylic acid ethyl ester To a solution of 500 mg 2-Iodo-5-methyl-3H-imidazole-4-carboxylic acid ethyl ester in 2 ml DMF 1.1 g caesium carbonate and 547 mg 3-Bromomethyl-5-(5-chloro-thiophen-2-yl)-isoxazole [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (2001), 460 pp. WO 0107436 A2] were added and the mixture was stirred for 2 h at RT. After addition of 5 ml water the mixture was filtered through a chem elut® cartridge by elution with ethyl acetate and then concentrated under reduced pressure. The residue was directly subjected to the subsequent saponification reaction without further purification. Yield: 630 mg.

(iii) 3-[5-(5-Chloro-thiophen-2-yl)-isoxazol-3-ylmethyl]-2-iodo-5-methyl-3H-imidazole-4-carboxylic acid To a solution of 700 mg3-[5-(5-Chloro-thiophen-2-yl)-isoxazol-3-ylmethyl]-2-iodo-5-methyl-3H-imidazole-4-carboxylic acid ethyl ester in 10 ml THF and 3 ml water 57.0 mg lithium hydroxide monohydrate were added. After stirring for 2 h at 60° C. the reaction was cooled to RT and concentrated under reduced pressure. The residue was acidified with half concentrated hydrochloric acid and the precipitate collected by filtration. The product was obtained as a white solid, which was dried under reduced pressure. Yield: 650 mg.

(iv) 3-[5-(5-Chloro-thiophen-2-yl)-isoxazol-3-ylmethyl]-2-iodo-5-methyl-3H-imidazol-4-carboxylic acid (1-isopropyl-piperidin-4-yl)-amide To a solution of 1.5 g 3-[5-(5-Chloro-thiophen-2-yl)-isoxazol-3-ylmethyl]-2-iodo-5-methyl-3H-imidazole-4-carboxylic acid, 1.7 ml N-NEM in 10 ml DCM 1.1 g TOTU were added and the mixture was stirred for 30 min at RT. Then 0.7 g 1-Isopropyl-piperidin-4-ylamine hydrochloride were added and the reaction was further stirred for 2 h. After addition of 2 ml sat. $NaHCO_3$ the mixture was filtered through a chem elut® cartridge by elution with ethyl acetate and then concentrated under reduced pressure. After removal of the solvent under reduced pressure the residue was purified by preparative HPLC (C18 reverse phase column, elution with a $H_2O$/MeCN gradient with 0.1% TFA). The fractions containing the product were evaporated and lyophilized to yield a white solid. The product was obtained as its trifluoroacetate salt. Yield: 350 mg MS (ES$^+$): m/e=574, chloro pattern.

Example 8

1-[5-(5-Chloro-thiophen-2-yl)-isoxazol-3-ylmethyl]-2-iodo-5-methyl-1H-imidazole-4-carboxylic acid (1-isopropyl-piperidin-4-yl)-amide This compound was isolated as a by-product in example 7. MS (ES$^+$): m/e=574, chloro pattern.

Example 9

3-[5-(5-Chloro-thiophen-2-yl)-isoxazol-3-ylmethyl]-2-methoxymethyl-3H-imidazole-4-carboxylic acid (1-isopropyl-piperidin-4-yl)-amide (i) N-Hydroxy-2-methoxy-acetamidine To a solution of 10 g methoxy-acetonitrile, 9.8 g hydroxylamine hydrochloride in 50 ml MeOH 15.8 g KOtBu were added in small portions at RT. After stirring for 5 h the precipitated salts were filtered off and the filtrate was concentrated to yield a white solid, which was used in the next reaction without further purification. Yield: 12 g (ii) 3-[(2-Methoxy-acetimidoyl)-aminooxy]-acrylic acid methyl ester To a solution of 1 g N-Hydroxy-2-methoxy-acetamidine in 10 ml MeOH 1.3 ml Propynoic acid methyl ester were added and the mixture heated to 60° C. for 3 h. After cooling, the reaction mixture was concentrated under reduced pressure to yield a brown solid, which was used in the next reaction without further purification. Yield: 450 mg (iii) 2-Methoxymethyl-3H-imidazole-4-carboxylic acid methyl ester A solution of 450 mg 3-[(2-Methoxy-acetimidoyl)-aminooxy]-acrylic acid methyl ester in 2 ml Dowtherm™ was heated at 180° C. for 18 h. After cooling, the dark brown reaction mixture was diluted with 10 ml heptane and the precipitating solid was purified by preparative HPLC (C18 reverse phase column, elution with a $H_2O$/MeCN gradient with 0.1% TFA). The fractions containing the product were evaporated and lyophilized to yield a yellow solid. The product was obtained as its trifluoroacetate salt. Yield: 250 mg.

(iv) 3-[5-(5-Chloro-thiophen-2-yl)-isoxazol-3-ylmethyl]-2-methoxymethyl-3H-imidazole-4-carboxylic acid methyl ester To a solution of 50 mg 2-Methoxymethyl-3H-imidazole-4-carboxylic acid methyl ester in 1 ml DMF, 95 mg caesium carbonate and 82 mg 3-Bromomethyl-5-(5-chloro-thiophen-2-yl)-isoxazole [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (2001), 460 pp. WO 0107436 A2] were added and the mixture was stirred for 2 h at RT. After addition of 5 ml water the mixture was filtered through a chem elut® cartridge by elution with ethyl acetate and then concentrated under reduced pressure. The residue was directly subjected to the subsequent saponification reaction without further purification. Yield: 72 mg.

(v) 3-[5-(5-Chloro-thiophen-2-yl)-isoxazol-3-ylmethyl]-2-methoxymethyl-3H-imidazole-4-carboxylic acid To a solution of 400 mg 3-[5-(5-Chloro-thiophen-2-yl)-isoxazol-3-ylmethyl]-2-methoxymethyl-3H-imidazole-4-carboxylic acid methyl ester in 5 ml THF and 1 ml water, 10.0 mg lithium hydroxide monohydrate were added. After stirring for 2 h at 60° C. the reaction was cooled to RT and concentrated under reduced pressure. The residue was acidified with half concentrated hydrochloric acid and filtered through a RP-18 cartridge eluting with $H_2O$/MeCN gradient. The fractions containing the product were evaporated and lyophilized to yield a white solid.
Yield: 320 mg (vi) 3-[5-(5-Chloro-thiophen-2-yl)-isoxazol-3-ylmethyl]-2-methoxymethyl-3H-imidazole-4-carboxylic acid (1-isopropyl-piperidin-4-yl)-amide To a solution of 60 mg 3-[5-(5-Chloro-thiophen-2-yl)-isoxazol-3-ylmethyl]-2-methoxymethyl-3H-imidazole-4-carboxylic acid, 85 µl N-NEM in 1 ml DCM 55 mg TOTU were added and the mixture was stirred for 30 min at RT. Then 34 mg of 1-Isopropyl-piperidin-4-ylamine hydrochloride were added and the reaction was stirred for 2 h. After addition of 2 ml sat. NaHCO$_3$ the mixture was filtered through a chem elut® cartridge by elution with ethyl acetate and then concentrated under reduced pressure. After removal of the solvent under reduced pressure the residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 10 mg; MS (ES$^+$): m/e=478, chloro pattern.

Example 10

1-[5-(5-Chloro-thiophen-2-y)-isoxazol-3-ylmethyl]-2-methoxymethyl-1H-imidazole-4-carboxylic acid (1-isopropyl-piperidin-4-yl)-amide This compound was isolated as a by-product in example 9. MS (ES$^+$): m/e=478, chloro pattern.

Example 11

3-[5-(5-Chloro-thiophen-2-yl)-isoxazol-3-ylmethyl]-2-cyclopropyl-3H-imidazole-4-carboxylic acid (1-isopropyl-piperidin-4-yl)-amide The title compound was prepared analogously to example 9 with the difference that cyclopropanecarbonitrile was used instead of methoxy-acetonitrile. MS (ESI+): m/e=474, chloro pattern.

Example 12

3-[5-(5-Chloro-thiophen-2-yl)-isoxazol-3-ylmethyl]-2-(2,6-difluoro-phenyl)-3H-imidazole-4-carboxylic acid (1-isopropyl-piperidin-4-yl)-amide The title compound was prepared analogously to example 9 with the difference that 2,6-Difluoro-benzonitrile was used instead of methoxy-acetonitrile. MS (ESI+): m/e=546, chloro pattern.

Example 13

3-[5-(5-Chloro-thiophen-2-yl)-isoxazol-3-ylmethyl]-2-cyclopentyl-3H-imidazole-4-carboxylic acid (1-isopropyl-piperidin-4-yl)-amide The title compound was prepared analogously to example 9 with the difference that cyclopentanecarbonitrile was used instead of methoxy-acetonitrile. MS (ESI+): m/e=502, chloro pattern.

Example 14

3-[5-(5-Chloro-thiophen-2-yl)-isoxazol-3-ylmethyl]-2-(2-methoxy-ethyl)-3H-imidazole-4-carboxylic acid (1-isopropyl-piperidin-4-yl)-amide The title compound was prepared analogously to example 9 with the difference that 3-Methoxy-propionitrile was used instead of methoxy-acetonitrile. MS (ESI+): m/e=492, chloro pattern.

Example 15

3-[5-(5-Chloro-thiophen-2-yl)-isoxazol-3-ylmethyl]-2-(2,6-dichloro-phenyl)-3H-imidazole-4-carboxylic acid (1-isopropyl-piperidin-4-yl)-amide The title compound was prepared analogously to example 9 with the difference that 2,6-Dichloro-benzonitrile was used instead of methoxy-acetonitrile. MS (ESI+): m/e=578, chloro pattern.

Example 16

3-[5-(5-Chloro-thiophen-2-yl)-isoxazol-3-ylmethyl]-2-isopropyl-3H-imidazole-4-carboxylic acid (1-isopropyl-piperidin-4-yl)-amide The title compound was prepared analogously to example 9 with the difference that Isobutyronitrile was used instead of methoxy-acetonitrile. MS (ESI+): m/e=476, chloro pattern.

Example 17

3-[5-(5-Chloro-thiophen-2-yl)-isoxazol-3-ylmethyl]-2-pyridin-2-yl-3H-imidazole-4-carboxylic acid (1-isopropyl-piperidin-4-yl)-amide The title compound was prepared analogously to example 9 with the difference that Pyridine-2-carbonitrile was used instead of methoxy-acetonitrile. MS (ESI+): m/e=511, chloro pattern.

Example 18

3-[5-(5-Chloro-thiophen-2-yl)-isoxazol-3-ylmethyl]-5-methyl-2-phenyl-3H-imidazole-4-carboxylic acid (1-isopropyl-piperidin-4-yl)-amide (i) 5-Methyl-2-phenyl-3H-imidazole-4-carboxylic acid methyl ester A solution of 150 mg 2-Iodo-5-methyl-3H-imidazole-4-carboxylic acid ethyl ester, 78 mg Phenyl boronic acid and 600 µl 2M aqueous Na$_2$CO$_3$ solution in 3 ml DME was purged with argon for 15 min. Then 20 mg Pd(Ph$_3$)$_4$ were introduced and the reaction mixture heated for 15 min to 150° C. under microwave irradiation (150 W, CEM Discover™ apparatus). After addition of 2 ml of water the mixture was filtered through a chem elut® cartridge by elution with ethyl acetate and then concentrated under reduced pressure. The residue was purified by preparative HPLC (C18 reverse phase column, elution with a H$_2$O/MeCN gradient with 0.1% TFA). The fractions containing the product were evaporated and lyophilized to yield a white solid. Yield: 103 mg (ii) 3-[5-(5-Chloro-thiophen-2-yl)-isoxazol-3-ylmethyl]-5-methyl-2-phenyl-3H-imidazole-4-carboxylic acid methyl ester To a solution of 60 mg 5-Methyl-2-phenyl-3H-imidazole-4-carboxylic acid methyl ester in 1 ml DMF 95 mg caesium carbonate and 82 mg 3-Bromomethyl-5-(5-chloro-thiophen-2-yl)-isoxazole were added and the mixture was stirred for 2 h at 60° C. After addition of 5 ml water the mixture was filtered through a chem elut® cartridge by elution with ethyl acetate and then concentrated under reduced pressure. The residue was directly subjected to the subsequent saponification reaction without further purification. Yield: 78 mg.

(iii) 3-[5-(5-Chloro-thiophen-2-yl)-isoxazol-3-ylmethyl]-5-methyl-2-phenyl-3H-imidazole-4-carboxlic acid To a solution of 78 mg 3-[5-(5-Chloro-thiophen-2-yl)-isoxazol-3-ylmethyl]-2-methoxymethyl-3H-imidazole-4-carboxylic acid methyl ester in 2 ml THF and 1 ml water, 10 mg lithium hydroxide monohydrate were added. After stirring for 2 h at 60° C. the reaction was cooled to RT and concentrated under reduced pressure. The residue was acidified with half concentrated hydrochloric acid and the precipitating white product was collected by filtration and used without further purification. Yield: 50 mg.

(iv) 3-[5-(5-Chloro-thiophen-2-yl)-isoxazol-3-ylmethyl]-5-methyl-2-phenyl-3H-imidazole-4-carboxylic acid (1-isopropyl-piperidin-4-yl)-amide To a solution of 50 mg 3-[5-(5-Chloro-thiophen-2-yl)-isoxazol-3-ylmethyl]-5-methyl-2-phenyl-3H-imidazole-4-carboxylic acid, 65 μl N-NEM in 1 ml DCM 42 mg TOTU were added and the mixture was stirred for 30 min at RT. Then 25 mg of 1-Isopropyl-piperidin-4-ylamine hydrochloride were added and the reaction was stirred for 1 h. After addition of 2 ml sat. NaHCO$_3$ the mixture was filtered through a chem elut® cartridge by elution with ethyl acetate and then concentrated under reduced pressure. After removal of the solvent under reduced pressure the residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 8 mg; MS (ESI+): m/e=524, chloro pattern.

Example 19

1-[5-(5-Chloro-thiophen-2-yl)-isoxazol-3-ylmethyl]-5-methyl-2-phenyl-1H-imidazole-4-carboxylic acid (1-isopropyl-piperidin-4-yl)-amide The title compound was prepared analogously to example 18 with the difference that 1-[5-(5-Chloro-thiophen-2-yl)-isoxazol-3-ylmethyl]-2-iodo-5-methyl-1H-imidazole-4-carboxylic acid (1-isopropyl-piperidin-4-yl)-amide was used instead of 3-[5-(5-Chloro-thiophen-2-yl)-isoxazol-3-ylmethyl]-5-methyl-2-phenyl-3H-imidazole-4-carboxylic acid (1-isopropyl-piperidin-4-yl)-amide. MS (ESI+): m/e=524, chloro pattern.

Example 20

3-[5-(5-Chloro-thiophen-2-yl)-isoxazol-3-ylmethyl]-2-pyridin-3-yl-3H-imidazole-4-carboxylic acid (1-isopropyl-piperidin-4-yl)-amide The title compound was prepared analogously to example 9 with the difference that Pyridine-3-carbonitrile was used instead of methoxy-acetonitrile. MS (ESI+): m/e=511, chloro pattern.

Example 21

3-[5-(5-Chloro-thiophen-2-yl)-isoxazol-3-ylmethyl]-2-(2-methyl-thiazol-4-yl)-3H-imidazole-4-carboxylic acid (1-isopropyl-piperidin-4-yl)-amide The title compound was prepared analogously to example 9 with the difference that 2-Methyl-thiazole-4-carbonitrile was used instead of methoxy-acetonitrile. MS (ESI+): m/e=531, chloro pattern.

Example 22

1-[5-(5-Chloro-thiophen-2-yl)-isoxazol-3-ylmethyl]-2-(2-methyl-thiazol-4-yl)-1H-imidazol-4-carboxylic acid (1-isopropyl-piperidin-4-yl)-amide This compound was isolated as a by-product in example 21. MS (ESI+): m/e=531, chloro pattern.

Example 23

3-[5-(5-Chloro-thiophen-2-yl)-isoxazol-3-ylmethyl]-2-ethanesulfonyl-3H-imidazole-4-carboxylic acid (1-isopropyl-piperidin-4-yl)-amide The title compound was prepared analogously to example 1 with the difference 2-Ethanesulfonyl-3H-imidazole-4-carboxylic acid ethyl ester was used instead of 3H-Imidazole-4-carboxylic acid methyl ester. MS (ESI+): m/e=526, chloro pattern.

Example 24

3-[5-(5-Chloro-thiophen-2-yl)-isoxazol-3-ylmethyl]-5-methyl-3H-imidazole-2,4-dicarboxylic acid 2-amide 4-[(1-isopropyl-piperidin-4-yl)-amide]

(i) 2-Cyano-5-methyl-3H-imidazole-4-carboxylic acid ethyl ester

To a solution of 1 g 2-Iodo-5-methyl-3H-imidazole-4-carboxylic acid ethyl ester in 3 ml pyridine 640 mg CuCN were added and the mixture stirred for 3 h at 110° C. Then the pyridine was removed under reduced pressure and the residue was directly purified by chromatography on silica eluting with DCM/MeOH 97:3. Yield: 494 mg.

(ii) 2-Carbamoyl-3-[5-(5-chloro-thiophen-2-yl)-isoxazol-3-ylmethyl]-5-methyl-3H-imidazole-4-carboxylic acid A suspension of 194 mg 2-Cyano-5-methyl-3H-imidazole-4-carboxylic acid ethyl ester, 301 mg 3-Bromomethyl-5-(5-chloro-thiophen-2-yl)-isoxazole and 150 mg K$_2$CO$_3$ in 2 ml DMF was stirred for 5 h at RT. After addition of 2 ml brine the mixture was filtered through a chem elut® cartridge by elution with ethyl acetate and then concentrated under reduced pressure. The residue was then dissolved in 5 ml THF/MeOH/water 3:1:1 and treated with 30 mg LiOH monohydrate at RT. Then the solvent was removed under reduced pressure and the residue was taken-up in 5 ml 5 M HCl. The acid precipitated as a brown solid and was dried under reduced pressure. Yield: 280 mg

(iii) 3-[5-(5-Chloro-thiophen-2-yl)-isoxazol-3-ylm-ethyl]-5-methyl-3H-imidazole-2,4-dicarboxyalic acid 2-amide 4-[(1-isopropyl-piperidin-4-yl)-amide]

To a solution of 2-Carbamoyl-3-[5-(5-chloro-thiophen-2-yl)-isoxazol-3-ylmethyl]-5-methyl-3H-imidazole-4-carboxylic acid, 0.15 ml $NEt_3$ in 2 ml DMF 70 mg BOP—Cl and 0.7 g 1-Isopropyl-piperidin-4-ylamine hydrochloride were added and the reaction was stirred for 5 h at RT. After addition of 2 ml sat. $NaHCO_3$ the mixture was filtered through a chem elut® cartridge by elution with ethyl acetate and then concentrated under reduced pressure. After removal of the solvent under reduced pressure the residue was purified by preparative HPLC (C18 reverse phase column, elution with a $H_2O$/MeCN gradient with 0.1% TFA). The fractions containing the product were evaporated and lyophilized to yield a white solid. The product was obtained as its trifluoroacetate salt. Yield: 20 mg; MS (ES$^+$): m/e=491, chloro pattern.

Example 25

1-[5-(5-Chloro-thiophen-2-yl)-isoxazol-3-ylmethyl]-5-methyl-1H-imidazole-2,4-dicarboxylic acid 2-amide 4-[(1-isopropyl-piperidin-4-yl)-amide]

This compound was isolated as a by-product in example 24. MS (ESI+): m/e=491, chloro pattern.

Example 26

2-Bromo-3-[5-(5-chloro-thiophen-2-yl)-isoxazol-3-ylmethyl]-5-methyl-3H-imidazole-4-carboxylic acid (1-isopropyl-piperidin-4-yl)-amide The title compound was prepared analogously to example 7 with the difference that NBS was used instead of NIS in the initial halogenation step. MS (ESI+): m/e=527, chloro pattern.

Example 27

2-Bromo-1-[5-(5-chloro-thiophen-2-yl)-isoxazol-3-ylmethyl]-5-methyl-1H-imidazole-4-carboxylic acid (1-isopropyl-piperidin-4-yl)-amide This compound was isolated as a by-product in example 26. MS (ESI+): m/e=527, chloro pattern.

Example 28

2-(4-Chlorophenyl)-1-[5-(5-chlorothiophen-2-yl)-isoxazol-3-ylmethyl]-1H-imidazole-4-carboxylic acid (1-isopropyl-piperidin-4-yl)-amide

(i) 2-(4-Chloro-phenyl)-3H-imidazole-4-carboxylic acid ethyl ester 1.0 g (5.9 mmol) of 4-chloro-N-hydroxy-benzamidine and 776 mg (7.96 mmol) of propynoic acid ethyl ester were dissolved in methanol and the resulting solution was boiled under reflux for 15 h. The solvent was removed under reduced pressure, and the residue was dissolved in Dowtherm A. This solution was heated to 190° C. for 2.5 h, allowed to cool, then poured into n-heptane. The precipitated product was filtered off and washed with n-heptane.
Yield: 759 mg; MS (LCMS-ES$^+$): m/e=251, chloro pattern.

(ii) 2-(4-Chloro-phenyl)-1-[5-(5-chloro-thiophen-2-yl)-isoxazol-3-ylmethyl]-1H-imidazole-4-carboxylic acid ethyl ester 500 mg (2.0 mmol) of 2-(4-Chlorophenyl)-3H-imidazole-4-carboxylic acid ethyl ester was dissolved in 5 ml of DMF and 2.6 g (8 mmol) of cesium carbonate were added at RT. After stirring for 15 min, 445 mg (1.6 mmol) of 3-bromomethyl-5-(5-chloro-thiophen-2-yl)-isoxazole were added. The reaction was stirred at room temperature for 16 h. The reaction solution was filtered and the product was purified by preparative RP-HPLC eluting with a gradient of 0-100% acetonitrile in water (+0.01% trifluoroacetic acid). After lyophilization the product was obtained as a white solid.
Yield: 480 mg; MS (LCMS-ES$^+$): m/e=448.

(iii) 2-(4-Chlorophenyl)-1-[5-(5-chloro-thiophen-2-yl)-isoxazol-3-ylmethyl]-1H-imidazole-4-carboxylic acid 480 mg (1.1 mg) of 2-(4-Chloro-phenyl)-1-[5-(5-chloro-thiophen-2-yl)-isoxazol-3-ylmethyl]-1H-imidazole-4-carboxylic acid ethyl ester was dissolved in 10 ml of dioxan and 10 ml of 2 N aqueous NaOH was added. The solution was stirred at 60° C. for 3 h. The solution was poured into water and the pH was adjusted to 3 by the addition of 2 N aqueous HCl. The precipitated product was filtered off and dried.
Yield: 258 mg; MS (LCMS-ES$^+$): m/e=420.

(iv) 2-(4-Chlorophenyl)-1-[5-(5-chlorothiophen-2-yl)-isoxazol-3-ylmethyl]-1H-imidazole-carboxylic acid (1-isopropyl-piperidin-4-yl)-amide 50 mg (0.12 mmol) of 2-(4-Chlorophenyl)-1-[5-(5-chloro-thiophen-2-yl)-isoxazol-3-ylmethyl]-1H-imidazole-4-carboxylic acid was dissolved in 3 ml of DMF and 39 mg (0.12 mmol) of TOTU and 0.15 ml (1.2 mmol) of NEM was added. This solution was stirred at room temperature for 30 min. 25.6 mg (0.12 mmol) of 1-isopropyl-piperidin-4-ylamine dihydrochloride was added and the resulting solution was stirred at room temperature for 16 h. The product was purified by preparative RP-HPLC eluting with a gradient of 0% to 100% acetonitrile in water (added 0.01% trifluoroacetic acid). After lyophilization the product was obtained as its trifluoroacetate salt. Yield 39.8 mg; MS (LCMS-ES$^+$): m/e=544 (M+H+).

Example 29

3-[(5-Chloro-pyridin-2-ylcarbamoyl)-methyl]-3H-imidazole-4-carboxylic acid (1-isopropyl-piperidin-4-yl)-amide

(i) 2-Bromo-N-(5-chloro-pyridin-2-yl)-acetamide

To a solution of 5 g 5-Chloro-pyridin-2-ylamine and 1.5 ml pyridine in 30 ml toluene 8 g bromo-acetyl bromide dissolved in 10 ml toluene was added dropwise under ice cooling. After 2 h the precipitate was isolated by filtration and recristallized from toluene to yield a white solid.
Yield: 12 g.

(ii) 3-[(5-Chloro-pyridin-2-ylcarbamoyl)-methyl]-3H-imidazole-4-carboxylic acid A suspension of 200 mg 3H-Imidazole-4-carboxylic acid methyl ester, 396 mg), 2-Bromo-N-(5-chloro-pyridin-2-yl)- acetamide and 220 mg K$_2$CO$_3$ in 2 ml DMF was stirred for 16 h at RT. The solvent was removed under reduced pressure and the precipitate dissolved in 5 ml THF/water 2:1. Then, 1.5 ml KOH 10% was added at RT and the reaction mixture was stirred for 16 h. Finally, 3 ml of halfconcentrated hydrochloric acid was added to precipitate the acid as a white solid. Yield: 260 mg.

(iii) 3-[(5-Chloro-pyridin-2-ylcarbamoyl)-methyl]-3H-imidazole-4-carboxylic acid (1-isopropyl-piperidin-4-yl)-amide To a solution of 3-[(5-Chloro-pyridin-2-ylcarbamoyl)-methyl]-3H-imidazole-4-carboxylic acid, 0.1 ml NEt$_3$ in 1 ml DMF 45 mg BOP—Cl and 39 mg 1-Isopropyl-piperidin-4-ylamine hydrochloride were added and the reaction was stirred for 16 h. After addition of 2 ml sat. NaHCO$_3$ the mixture was filtered through a chem elut® cartridge by elution with ethyl acetate and then concentrated under reduced pressure. After removal of the solvent under reduced pressure the residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 80 mg; MS (ES$^+$): m/e=405, chloro pattern.

Example 30

3-[(4-Chloro-phenylcarbamoyl)-methyl]-2-methoxymethyl-3H-imidazole-4-carboxylic acid (1-isopropyl-piperidin-4-yl)-amide The title compound was prepared analogously to example 29 with the difference that 2-Bromo-N-(4-chloro-phenyl)-acetamide and 2-Methoxymethyl-3H-imidazole-4-carboxylic acid methyl ester were used instead of 2-Bromo-N-(5-chloro-pyridin-2-yl)-acetamide and 3H-Imidazole-4-carboxylic acid methyl ester in the alkylation step. MS (ESI+): m/e=448, chloro pattern.

Example 31

1-[(4-Chloro-phenylcarbamoyl)-methyl]-2-methoxymethyl-1H-imidazole-4-carboxylic acid (1-isopropyl-piperidin-4-yl)-amide This compound was isolated as a by-product in example 30. MS (ESI+): m/e=448, chloro pattern.

Example 32

1-[(5-Chloro-pyridin-2-ylcarbamoyl)-methyl]-2-ethanesulfonyl-1H-imidazole-4-carboxylic acid (1-isopropyl-piperidin-4-yl)-amide The title compound was prepared analogously to example 29 with the difference that 2-ethanesulfonyl-3H-imidazole-4-carboxylic acid ethyl ester was used instead of 3H-imidazole-4-carboxylic acid methyl ester. MS (ESI+): m/e=497, chloro pattern.

Example 33

5-Chloro-3-[(5-chloro-pyridin-2-ylcarbamoyl)-methyl]-2-phenyl-3H-imidazole-4-carboxylic acid (1-isopropyl-piperidin-4-yl)-amide The title compound was prepared analogously to example 29 with the difference that 5-Chloro-2-phenyl-3H-imidazole-4-carboxylic acid methyl ester was used instead of 3H-Imidazole-4-carboxylic acid methyl ester. MS (ESI+): m/e=515, chloro pattern.

Example 34

1-[5-(5-Chloro-thiophen-2-yl)-isoxazol-3-ylmethyl]-2-cyclopropyl-1H-imidazole-4-carboxylic acid (1-isopropyl-piperidin-4-yl)-amide This compound was isolated as a by-product in example 11. MS (ESI+): m/e=474, chloro pattern.

Example 35

3-[5-(5-Chloro-thiophen-2-yl)-isoxazol-3-ylmethyl]-2-(2-methoxy-phenyl)-5-methyl-3H-imidazole-4-carboxylic acid (1-isopropyl-piperidin-4-yl)-amide The title compound was prepared analogously to example 18 with the difference that 2-methoxyphenyl boronic acid was used instead of phenyl boronic acid. MS (ESI+): m/e=555, chloro pattern.

Example 36

3-[5-(5-Chloro-thiophen-2-yl)-isoxazol-3-ylmethyl]-2-(3-trifluoromethyl-phenyl)-3H-imidazole-4-carboxylic acid (1-isopropyl-piperidin-4-yl)-amide The title compound was prepared analogously to example 9 with the difference that 3-trifluoromethyl-benzonitrile was used instead of methoxy-acetonitrile. MS (ESI+): m/e=579, chloro pattern.

Example 37

1-[5-(5-Chloro-thiophen-2-yl)-isoxazol-3-ylmethyl]-5-(1-isopropyl-piperidin-4-ylcarbamoyl)-1H-imidazole-2-carboxylic acid ethyl ester (i) 3-[5-(5-Chloro-thiophen-2-yl)-isoxazol-3-ylmethyl]-3H-imidazole-2,4-dicarboxylic acid 4-tert-butyl ester 2-ethyl ester and 1-[5-(5-Chloro-thiophen-2-yl)-isoxazol-3-ylmethyl]-1H-imidazole-2,4-dicarboxylic acid 4-tert-butyl ester 2-ethyl ester To a solution of 260 mg of 3H-Imidazole-2,4-dicarboxylic acid 4-tert-butyl ester 2-ethyl ester [prepared by adopting a procedure described by J.-C. Aloup, F. Audiau, M. Barreau, D. Damour, A. Genevois-Borella, P. Jimonet, S. Mignani, Y. Ribeill PCT Int. Appl. (1996) WO96/02544 A1] in DMF (10 ml) was added potassium carbonate (178 mg) and 3-Bromomethyl-5-(5-chloro-thiophen-2-yl)-isoxazole (301 mg). The mixture was stirred for 2 h at RT. The solvent was removed in vacuo and the residue was purified by flash column chromatography on silica (n-heptane/ethyl acetate 2:1 to ethyl acetate) to provide 1-[5-(5-Chloro-thiophen-2-yl)-isoxazol-3-ylmethyl]-1H-imidazole-2,5-dicarboxylic acid 4-tert-butyl ester 2-ethyl ester (73 mg, 15%; MS (ESI+): m/e=437, chloro pattern) and 3-[5-(5-Chloro-thiophen-2-yl)-isoxazol-3-ylmethyl]-3H-imidazole-2,4-dicarboxylic acid 4-tert-butyl ester 2-ethyl ester (342 mg, 72%; MS (ESI+): m/e=437, chloro pattern) as white solids.

(ii) 3-[5-(5-Chloro-thiophen-2-yl)-isoxazol-3-ylmethyl]-3H-imidazole-2,4-dicarboxylic acid 2-ethyl ester To 24 mg of 3-[5-(5-Chloro-thiophen-2-yl)-isoxazol-3-ylmethyl]-3H-imidazole-2,4-dicarboxylic acid 4-tert-butyl ester 2-ethyl ester was added a 5 M solution of HCl in 2-propanol (2 mL). The mixture was stirred for 24 h at RT, concentrated in vacuo and the residue was purified by preparative HPLC (C18 reverse phase column, elution with a $H_2O$/MeCN gradient with 0.1% TFA). The fractions containing the product were evaporated to provide 14 mg of the title compound as a pale yellow solid. Yield: 14 mg; MS (ESI+): m/e=381, chloro pattern.

(iii) 1-[5-(5-Chloro-thiophen-2-yl)-isoxazol-3-ylmethyl]-5-(1-isopropyl-piperidin-4-ylcarbamoyl)-1H-imidazole-2-carboxylic acid ethyl ester To a solution of 12 mg of 3-[5-(5-Chloro-thiophen-2-yl)-isoxazol-3-ylmethyl]-3H-imidazole-2,4-dicarboxylic acid 2-ethyl ester (ii) in DMF (0.5 mL) and DCM (0.5 mL) was added successively 1-Hydroxy-7-azabenzotriazole (5 mg), N-Ethyl-N'-(3-dimethylaminopropyl)carbodiimide hydrochloride (7 mg) and diisopropyl ethylamine (26 µL). The mixture was stirred for 15 min at RT. 7 mg of 1-Isopropyl-piperidin-4-ylamine (dihydrochloride) were added and stirring was continued at RT. After 2 h the mixture was concentrated in vacuo and the residue was purified by preparative HPLC (C18 reverse phase column, elution with a $H_2O$/MeCN gradient with 0.1% TFA). The fractions containing the product were evaporated to provide 8.5 mg of the title compound as its trifluoroacetate salt. Yield: 8.5 mg; MS (ESI+): m/e=505, chloro pattern.

Example 38 and Example 39

1-[5-(5-Chloro-thiophen-2-yl)-isoxazol-3-ylmethyl]-2-(1-isopropyl-piperidin-4-ylcarbamoyl)-1H-imidazole-4-carboxylic acid tert-butyl ester and 1-[5-(5-Chloro-thiophen-2-yl)-isoxazol-3-ylmethyl]-2-(1-isopropyl-piperidin-4-ylcarbamoyl)-1H-imidazole-4-carboxylic acid To a solution of 1-isopropyl-piperidin-4-ylamine (142 mg) in DCM (4 mL) was added trimethyl aluminium (0.5 mL, 2M solution in hexanes) dropwise under an Ar atmosphere. The mixture was stirred for 15 min at RT. A solution of 1-[5-(5-Chloro-thiophen-2-yl)-isoxazol-3-ylmethyl]-1H-imidazole-2,4-dicarboxylic acid 4-tert-butyl ester 2-ethyl ester [example 1, (i)] (438 mg) in DCM (4 mL) was added dropwise and stirring was continued for 17 h at RT and 3 h at 35° C. After cooling the reaction was quenched by dropwise addition of 1M aqueous $KHSO_4$ solution, concentrated, taken up in 6N HCL and extracted with ethyl acetate. The combined organic extracts were washed with water and brine, dried over $MgSO_4$ and concentrated under reduced pressure. The residue was purified by preparative HPLC. The fractions containing the product were evaporated to provide 154 mg of 1-[5-(5-Chloro-thiophen-2-yl)-isoxazol-3-ylmethyl]-2-(1-isopropyl-piperidin-4-ylcarbamoyl)-1H-imidazole-4-carboxylic acid tert-butyl ester (example 2) as its trifluoroacetate salt. MS (ESI+): m/e=534, chloro pattern.

The aqueous phase was concentrated in vacuo and the residue was triturated with EtOH. The mixture was filtered from insoluble inorganic matter and the filtrate was concentrated to give 161 mg of 1-[5-(5-Chloro-thiophen-2-yl)-isoxazol-3-ylmethyl]-2-(1-isopropyl-piperidin-4-ylcarbamoyl)-1H-imidazole-4-carboxylic acid (example 3) as its hydrochloride salt. MS (ESI+): m/e=478, chloro pattern.

Example 40

1-[5-(5-Chloro-thiophen-2-yl)-isoxazol-3-ylmethyl]-2-(1-isopropyl-piperidin-4-ylcarbamoyl)-1H-imidazole-4-carboxylic acid methyl ester To a solution of 72 mg of 1-[5-(5-Chloro-thiophen-2-yl)-isoxazol-3-ylmethyl]-2-(1-isopropyl-piperidin-4-ylcarbamoyl)-1H-imidazole-4-carboxylic acid (example 3, hydrochloride salt) in DCM (3 mL) was added $NEt_3$ (58 µL), DMAP (1 mg) and DCC (32 mg). The mixture was stirred for 15 min at RT. MeOH (57 µL) was added and stirring was continued for 3.5 h at RT and 2 h at 50° C. After cooling to RT, the reaction mixture was washed with water, dried over $MgSO_4$ and concentrated under reduced pressure. The residue was purified by preparative HPLC. The fractions containing the product were evaporated to provide 1.3 mg of the title compound as its trifluoroacetate salt.

MS (ESI+): m/e=492, chloro pattern.

Example 41

1-[5-(5-Chloro-thiophen-2-yl)-isoxazol-3-ylmethyl]-1H-imidazole-2,4-dicarboxylic acid 4-amide 2-[(1-isopropyl-piperidin-4-yl)-amide]

To a solution of 109 mg of 1-[5-(5-Chloro-thiophen-2-yl)-isoxazol-3-ylmethyl]-2-(1-isopropyl-piperidin-4-ylcarbamoyl)-1H-imidazole-4-carboxylic acid (example 3, hydrochloride salt) in 1,4-dioxane (2 mL) was added pyridine (30 µL), $Boc_2O$ (53 mg) and $NH_4HCO_3$ (19 mg). The mixture was stirred for 2.5 h at RT, quenched by addition of water (50 mL), concentrated and extracted with DCM (2×). The combined organic phases were washed with water, dried over $MgSO_4$ and concentrated under reduced pressure to yield 59 mg of the title compound. MS (ESI+): m/e=477, chloro pattern.

Example 42

1-[5-(5-Chloro-thiophen-2-yl)-isoxazol-3-ylmethyl]-1H-imidazole-2,4-dicarboxylic acid 4-[(2-hydroxy-ethyl)-methyl-amide] 2-[(1-isopropyl-piperidin-4-yl)-amide]

To a solution of 216 mg of 1-[5-(5-Chloro-thiophen-2-yl)-isoxazol-3-ylmethyl]-2-(1-isopropyl-piperidine-4-ylcarbamoyl)-1H-imidazole-4-carboxylic acid (example 39, hydrochloride salt) in DCM (5 mL) was added oxalyl chloride (52 µL) and 1 drop of DMF. The mixture was stirred at 40° C. for 1 h, concentrated under reduced pressure and the residue was taken up in DCM (5 mL). $NEt_3$ (277 µL) was added, followed by N-methylamino-ethanol (48 µL). The mixture was stirred for 1 h at 40° C., concentrated and the residue was purified by preparative HPLC. The fractions containing the product were evaporated to provide 48 mg of the title compound as its trifluoroacetate salt. MS (ESI+): m/e=535, chloro pattern.

Example 43 and Example 44

1-[5-(5-Chloro-thiophen-2-yl)-isoxazol-3-ylmethyl]-4-(3-hydroxy-azetidine-1-carbonyl)-1H-imidazole-2-carboxylic acid (1-isopropyl-piperidin-4-yl)-amide and 1-[5-(5-Chloro-thiophen-2-yl)-isoxazol-3-ylmethyl]-1H-imidazole-2,4-dicarboxylic acid 4-dimethylamide 2-[(1-isopropyl-piperidin-4-yl)-amide]

Following the procedure from example 42 replacing N-methylamino-ethanol by azetidin-3-ol (66 mg) two products were isolated after HPLC purification:
1-[5-(5-Chloro-thiophen-2-yl)-isoxazol-3-ylmethyl]-4-(3-hydroxy-azetidine-1-carbonyl)-1H-imidazole-2-carboxylic acid (1-isopropyl-piperidin-4-yl)-amide (example 43) as its trifluoroacetate salt. Yield: 13 mg; MS (ESI+): m/e=533, chloro pattern.
1-[5-(5-Chloro-thiophen-2-yl)-isoxazol-3-ylmethyl]-1H-imidazole-2,4-dicarboxylic acid 4-dimethylamide 2-[(1-isopropyl-piperidin-4-yl)-amide] (example 44), as its trifluoroacetate salt. Yield: 24 mg; MS (ESI+): m/e=505, chloro pattern.

Example 45

1-[5-(5-Chloro-thiophen-2-yl)-isoxazol-3-ylmethyl]-2-(1-isopropyl-piperidin-4-ylcarbamoyl)-1H-imidazole-4-carboxylic acid cyclopropylmethyl ester Following the procedure from example 42 replacing N-methylamino-ethanol by cyclopropyl-methanol (47 µL) 1-[5-(5-Chloro-thiophen-2-yl)-isoxazol-3-ylmethyl]-2-(1-isopropyl-piperidin-4-ylcarbamoyl)-1H-imidazole-4-carboxylic acid cyclopropylmethyl ester was isolated after HPLC purification of the crude reaction mixture as its trifluoroacetate salt. Yield: 16 mg; MS (ESI+): m/e=532, chloro pattern.

Example 46

1-[5-(5-Chloro-thiophen-2-yl)-isoxazol-3-ylmethyl]-2-(1-isopropyl-piperidin-4-ylcarbamoyl)-1H-imidazole-4-carboxylic acid tert-butoxycarbonylmethyl ester Following the procedure from example 42 replacing N-methylamino-ethanol by hydroxy-acetic acid tert-butyl ester (76 µL) 1-[5-(5-Chloro-thiophen-2-yl)-isoxazol-3-ylmethyl]-2-(1-isopropyl-piperidin-4-ylcarbamoyl)-1H-imidazole-4-carboxylic acid tert-butoxycarbonylmethyl ester was isolated after HPLC purification of the crude reaction mixture as its trifluoroacetate salt. Yield: 5 mg; MS (ESI+): m/e=592, chloro pattern.

Example 47

1-[5-(5-Chloro-thiophen-2-yl)-isoxazol-3-ylmethyl]-1H-imidazole-2,4-dicarboxylic acid 4-[(2-hydroxy-ethyl)-amide] 2-[(1-isopropyl-piperidin-4-yl)-amide Following the procedure from example 42 replacing N-methylamino-ethanol by 2-amino-ethanol (35 µL) 1-[5-(5-Chloro-thiophen-2-yl)-isoxazol-3-ylmethyl]-1H-imidazole-2,4-dicarboxylic acid 4-[(2-hydroxy-ethyl)-amide] 2-[(1-isopropyl-piperidin-4-yl)-amide was isolated after HPLC purification of the crude reaction mixture as its trifluoroacetate salt. Yield: 13 mg; MS (ESI+): m/e=521, chloro pattern.

Example 48

1-[5-(5-Chloro-thiophen-2-yl)-isoxazol-3-ylmethyl]-4-(3-methoxy-azetidine-1-carbonyl)-1H-imidazole-2-carboxylic acid (1-isopropyl-piperidin-4-yl)-amide Following the procedure from example 42 replacing N-methylamino-ethanol by 3-methoxy-azetidine hydrochloride [prepared by adopting a procedure described by Y. Kobayashi, T. Shinozuka and O. Kanno, PCT Int. Appl. (2002) WO02/40483 A1] (71 mg) 1-[5-(5-Chloro-thiophen-2-yl)-isoxazol-3-ylmethyl]-4-(3-methoxy-azetidine-1-carbonyl)-1H-imidazole-2-carboxylic acid (1-isopropyl-piperidin-4-yl)-amide was isolated after HPLC purification of the crude reaction mixture as its trifluoroacetate salt. Yield: 19 mg; MS (ESI+): mi/e=547, chloro pattern.

Example 49

3-[1-[5-(5-Chloro-thiophen-2-yl)-isoxazol-3-ylmethyl]-2-(1-isopropyl-piperidin-4-ylcarbamoyl)-1H-imidazol-4-yl]-propionic acid methyl ester (i) 3-(1H-Imidazol-4-yl)-propionic acid methyl ester To a suspension of 3-(1H-Imidazol-4-yl)-propionic acid (700 mg) in MeOH (20 mL) was added trimethyl chlorosilane (2 mL) dropwise. The mixture was stirred for 6 h at RT and concentrated under reduced pressure. The residue was evaporated from MeOH (1×) and from toluene (1×) to give crude 3-(1H-imidazol-4-yl)-propionic acid methyl ester as its hydrochloride salt (950 mg, colorless solid), which was used without further purification in the next step.

(ii) 3-{1-[5-(5-Chloro-thiophen-2-yl)-isoxazol-3-ylmethyl]-1H-imidazol-4-yl}-propionic acid methyl ester To a solution of 190 mg of 3-(1H-Imidazol-4-yl)-propionic acid methyl ester (hydrochloride salt) in DMF (5 mL) was added $K_2CO_3$ (414 mg) and 3-Bromomethyl-5-(5-chloro-thiophen-2-yl)-isoxazole (278 mg). The mixture was stirred for 2 h at 70° C. After removal of the solvent in vacuo the residue was taken up in ethyl acetate. The mixture was washed with water and brine. The organic phase was dried over anhydrous $MgSO_4$ and concentrated under reduced pressure to give crude 3-{1-[5-(5-chloro-thiophen-2-yl)-isoxazol-3-ylmethyl]-1H-imidazol-4-yl}-propionic acid methyl ester (174 mg) as a brown solid which was used in the next step without further purification.

(iii) 3-[1-[5-(5-Chloro-thiophen-2-yl)-isoxazol-3-ylmethyl]-2-(1-isopropyl-piperidin-4-ylcarbamoyl)-1H-imidazol-4-yl]-propionic acid methyl ester To a solution of 3-{1-[5-(5-chloro-thiophen-2-yl)-isoxazol-3-ylmethyl]-1H-imidazol-4-yl}-propionic acid methyl ester (140 mg) and $NEt_3$ (70 µL) in DCM (5 mL) was added a solution of trichloroacetyl chloride (50 µL) in DCM (1 mL) dropwise at 0° C. The mixture was stirred for 5 min at 0° C.

and for 30 min at RT. More NEt₃ (280 μL) and 1-isopropyl-piperidin-4-ylamine dihydrochloride (88 mg) were added and stirring was continued for 2 h at RT. The mixture was concentrated and the residue was purified by preparative HPLC. The fractions containing the product were evaporated to provide 47 mg of the title compound as its trifluoroacetate salt. MS (ESI+): m/e=520, chloro pattern.

Example 50

1-(3-Methoxy-benzyl)-1H-imidazole-2-carboxylic acid (1-isopropyl-piperidin-4-yl)-amide (i) 1-(3-Methoxy-benzyl)-1H-imidazole To a solution of imidazole (1.00 g, 14.69 mmol, 1 equivalent) and Cs₂CO₃ (5.93 g, 1.2 equivalents) was added 3-methoxybenzyl bromide (3.24 g, 1.1 equiv.) dropwise at 5° C. The mixture was stirred for 1.5 h at 5° C., filtered and concentrated under reduced pressure to give 1-(3-methoxy-benzyl)-1H-imidazole (2.30 g) as a pale yellow oil was directly used in the next step without further purification.

(ii) 1-(3-Methoxy-benzyl)-1H-imidazole-2-carboxylic acid (1-isopropyl-piperidin-4-yl)-amide To a solution of 1-(3-methoxy-benzyl)-1H-imidazole (100 mg) and NEt₃ (147 μL) in DCM (5 mL) was added trichloroacetyl chloride (106 μL) dropwise. The mixture was stirred for 2 h at RT. More NEt₃ (147 μL) and 1-isopropyl-piperidin-4-ylamine (76 mg) were added and stirring was continued for 1 h at RT. The mixture was quenched by the addition of MeOH, concentrated and the residue was purified by preparative HPLC. The fractions containing the product were evaporated to provide 30 mg of the title compound as its trifluoroacetate salt. MS (ESI+): m/e=357.

Example 51

1-(3-Methoxy-benzyl)-1H-imidazole-2-carboxylic acid (1-isopropyl-piperidin-4-ylmethyl)-amide Following the procedure from example 50 replacing 1-isopropyl-piperidin-4-ylamine by C-(1-Isopropyl-piperidin-4-yl)-methylamine [prepared by adopting a procedure described in M. Nazare, M. Essrich, D. W. Will, H. Matter, K. Ritter, V. Wehner, Eur. Pat. Appl. (2003) EP 1314733 A1] in step (ii), 1-(3-Methoxy-benzyl)-1H-imidazole-2-carboxylic acid (1-isopropyl-piperidin-4-ylmethyl)-amide was isolated after HPLC purification of the crude reaction mixture as its trifluoroacetate salt. MS (ESI+): m/e=371.

Example 52

1-(3-chloro-benzyl)-1H-imidazole-2-carboxylic acid (1-isopropyl-piperidin-4-ylmethyl)-amide Following the procedure from example 50 replacing 3-methoxybenzyl bromide by 3-chlorobenzyl bromide in step (i), 1-(3-chloro-benzyl)-1H-imidazole-2-carboxylic acid (1-isopropyl-piperidin-4-ylmethyl)-amide was isolated after HPLC purification of the crude reaction mixture as its trifluoroacetate salt. MS (ESI+): m/e=361, chloro pattern.

Example 53

1-(3,4-Difluoro-benzyl)-1H-imidazole-2-carboxylic acid (1-isopropyl-piperidin-4-yl)-amide Following the procedure from example 50 replacing 3-methoxybenzyl bromide by 3,4-difluorobenzyl bromide in step (i), 1-(3,4-difluoro-benzyl)-1H-imidazole-2-carboxylic acid (1-isopropyl-piperidin-4-ylmethyl)-amide was isolated after HPLC purification of the crude reaction mixture as its trifluoroacetate salt. MS (ESI+): m/e=363.

Example 54

1-(3-Fluoro-benzyl)-1H-imidazole-2-carboxylic acid (1-isopropyl-piperidin-4-yl)-amide Following the procedure from example 50 replacing 3-methoxybenzyl bromide by 3-fluorobenzyl bromide in step (i), 1-(3-fluoro-benzyl)-1H-imidazole-2-carboxylic acid (1-isopropyl-piperidin-4-ylmethyl)-amide was isolated after HPLC purification of the crude reaction mixture as its trifluoroacetate salt. MS (ESI+): m/e=344.

Example 55

[1-(3-Methoxy-benzyl)-1H-imidazol-2-yl]-[4-(1-methyl-piperidin-4-yl)-piperazin-1-yl]-methanone Following the procedure from example 50 replacing 1-isopropyl-piperidin-4-ylamine by 1-(1-Methyl-piperidin-4-yl)-piperazine in step (ii), [1-(3-Methoxy-benzyl)-1H-imidazol-2-yl]-[4-(1-methyl-piperidin-4-yl)-piperazin-1-yl]-methanone was isolated after HPLC purification of the crude reaction mixture as its trifluoroacetate salt. MS (ESI+): m/e=398.

Example 56

1-(3-Methoxy-benzyl)-1H-imidazole-2-carboxylic acid (3,4,5,6-tetrahydro-2H-[1,4]'bipyridinyl-4-ylmethyl)-amide Following the procedure from example 50 replacing 1-isopropyl-piperidin-4-ylamine by C-(3,4,5,6-tetrahydro-2H-[1,4]bipyridinyl-4-yl)-methylamine [prepared by adopting a procedure described in M. Nazare, M. Essrich, D. W. Will, H. Matter, K. Ritter, V. Wehner, Eur. Pat. Appl. (2003) EP 1314733 A1] in step (ii), 1-(3-Methoxy-benzyl)-1H-imidazole-2-carboxylic acid (3,4,5,6-tetrahydro-2H-[1,4]bipyridinyl-4-ylmethyl)-amide was isolated after HPLC purification of the crude reaction mixture as its trifluoroacetate salt. MS (ESI+): m/e=406.

Example 57

1-(3-Methoxy-benzyl)-1H-imidazole-2-carboxylic acid (1-pyridin-4-yl-azetidin-3-ylmethyl)-amide Following the procedure from example 50 replacing 1-isopropyl-piperidin-4-ylamine by C-(1-pyridin-4-yl-azetidin-3-yl)-methylamine [prepared by adopting a procedure described in M. Nazare, M. Essrich, D. W. Will, H. Matter, K. Ritter, V. Wehner, Eur. Pat. Appl. (2003) EP 1314733 A1] in step (ii), 1-(3-Methoxy-benzyl)-1H-imidazole-2-carboxylic acid (1-pyridin-4-yl-azetidin-3-ylmethyl)-amide was isolated after HPLC purification of the crude reaction mixture as its trifluoroacetate salt. MS (ESI+): m/e=378.

Example 58

1-(3-methoxy-benzyl)-1H-imidazole-2-carboxylic acid (3,4,5,6-tetrahydro-2H-[1,4]bipyridinyl-4-yl)-amide Following the procedure from example 50 replacing 1-isopropyl-piperidin-4-ylamine by 3,4,5,6-tetrahydro-2H-[1,4']bipyridinyl-4-ylamine [prepared by adopting a procedure described in M. Nazare, M. Essrich, D. W. Will, H. Matter, K. Ritter, V. Wehner, Eur. Pat. Appl. (2003) EP 1314733 A1] in step (ii), 1-(3-methoxy-benzyl)-1H-imidazole-2-carboxylic acid (3,4,5,6-tetrahydro-2H-[1,4']bipyridinyl-4-yl)-amide was isolated after HPLC purification of the crude reaction mixture as its trifluoroacetate salt. MS (ESI+): m/e=392.

Example 59

1-(3-methoxy-benzyl)-1H-imidazole-2-carboxylic acid (1-pyridin-4-yl-azetidin-3-yl)-amide Following the procedure from example 50 replacing 1-isopropyl-piperidin-4-ylamine by 1-pyridin-4-yl-azetidin-3-ylamine [prepared by adopting a procedure described in M. Nazare, M. Essrich, D. W. Will, H. Matter, K. Ritter, V. Wehner, Eur. Pat. Appl. (2003) EP 1314733 A1] in step (ii), 1-(3-methoxy-benzyl)-1H-imidazole-2-carboxylic acid (1-pyridin-4-yl-azetidin-3-yl)-amide was isolated after HPLC purification of the crude reaction mixture as its trifluoroacetate salt.
MS (ESI+): m/e=364.

Example 60

1-[5-(5-Chloro-thiophen-2-yl)-isoxazol-3-ylmethyl]-1H-imidazole-2-carboxylic acid (1-isopropyl-piperidin-4-yl)-amide (i) 5-(5-Chloro-thiophen-2-yl)-3-imidazol-1-ylmethyl-isoxazole To a solution of imidazole (34 mg) in MeCN (3 mL) was added K$_2$CO$_3$ (138 mg), n-hexadecyltrimethylphosphonium bromide (1 mg) and 3-bromomethyl-5-(5-chloro-thiophen-2-yl)-isoxazole (139 mg). The mixture was stirred for 3 h at 70° C. After cooling to RT the reaction mixture was diluted with DCM (5 mL) and filtered. The filtrate was concentrated in vacuo to give crude 5-(5-Chloro-thiophen-2-yl)-3-imidazol-1-ylmethyl-isoxazole (153 mg) which was used in the next step without further purification.

(ii) 1-[5-(5-Chloro-thiophen-2-yl)-isoxazol-3-ylmethyl]-1H-imidazole-2-carboxylic acid (1-isopropyl-piperidin-4-yl)-amide To a solution of 5-(5-Chloro-thiophen-2-yl)-3-imidazol-1-ylmethyl-isoxazole (85 mg) and NEt$_3$ (89 µL) in DCM (3 mL) was added trichloroacetyl chloride (43 µL) dropwise at 0° C. The mixture was stirred for 5 min at 0° C. and for 30 min at RT. More NEt$_3$ (133 µL) and 1-isopropyl-piperidin-4-ylamine dihydrochloride (88 mg) were added and stirring was continued for 2 h at RT. The mixture was concentrated and the residue was purified by preparative HPLC. The fractions containing the product were evaporated to provide 67 mg of the title compound as its trifluoroacetate salt. MS (ESI+): mi/e=434, chloro pattern.

Example 61

1-[2-(4-Chloro-phenyl)-ethyl]-1H-imidazole-2-carboxylic acid (1-isopropyl-piperidin-4-yl)-amide Following the procedure from example 60 replacing 3-bromomethyl-5-(5-chloro-thiophen-2-yl)-isoxazole by 1-chloro-4-(2-chloro-ethyl)-benzene in step (i), 1-[2-(4-Chloro-phenyl)-ethyl]-1H-imidazole-2-carboxylic acid (1-isopropyl-piperidin-4-yl)-amide was isolated after HPLC purification of the crude reaction mixture as its trifluoroacetate salt.
MS (ESI+): m/e=375, chloro pattern.

Example 62

1-[5-(5-Chloro-thiophen-2-yl)-isoxazol-3-ylmethyl]-1H-imidazole-2-carboxylic acid (1-isopropyl-azetidin-3-ylmethyl)-amide Following the procedure from example 60 replacing 1-isopropyl-piperidin-4-ylamine by C-(1-isopropyl-azetidin-3-yl)-methylamine [prepared by adopting a procedure described in M. Nazare, M. Essrich, D. W. Will, H. Matter, K. Ritter, V. Wehner, Eur. Pat. Appl. (2003) EP 1314733 A1] in step (ii), 1-[5-(5-Chloro-thiophen-2-yl)-isoxazol-3-ylmethyl]-1H-imidazole-2-carboxylic acid (1-isopropyl-azetidin-3-ylmethyl)-amide was isolated after HPLC purification of the crude reaction mixture as its trifluoroacetate salt. MS (ESI+): m/e=420, chloro pattern.

Example 63

1-[5-(5-Chloro-thiophen-2-yl)-isoxazol-3-ylmethyl]-1H-imidazole-2-carboxylic acid (3,4,5,6-tetrahydro-2H-[1,4']bipyridinyl-4-ylmethyl)-amide Following the procedure from example 60 replacing 1-isopropyl-piperidin-4-ylamine by C-(3,4,5,6-tetrahydro-2H-[1,4']bipyridinyl-4-yl)-methylamine [prepared by adopting a procedure described in M. Nazare, M. Essrich, D. W. Will, H. Matter, K. Ritter, V. Wehner, Eur. Pat. Appl. (2003) EP 1314733 A1] in step (ii), 1-[5-(5-Chloro-thiophen-2-yl)-isoxazol-3-ylmethyl]-1H-imidazole-2-carboxylic acid (3,4,5,6-tetrahydro-2H-[1,4']bipyridinyl-4-ylmethyl)-amide was isolated after HPLC purification of the crude reaction mixture as its trifluoroacetate salt. MS (ESI+): m/e=483, chloro pattern.

Example 64

1-[5-(5-Chloro-thiophen-2-yl)-isoxazol-3-ylmethyl]-1H-imidazole-2-carboxylic acid (1-isopropyl-piperidin-4-ylmethyl)-amide Following the procedure from example 60 replacing 1-isopropyl-piperidin-4-ylamine by C-(1-Isopropyl-piperidin-4-yl)-methylamine [prepared by adopting a procedure described in M. Nazare, M. Essrich, D. W. Will, H. Matter, K. Ritter, V. Wehner, Eur. Pat. Appl. (2003) EP 1314733 A1] in step (ii),1-[5-(5-Chloro-thiophen-2-yl)-isoxazol-3-ylmethyl]-1H-imidazole-2-carboxylic acid (1-isopropyl-piperidin-4-ylmethyl)-amide was isolated after HPLC purification of the crude reaction mixture as its trifluoroacetate salt. MS (ESI+): m/e=448, chloro pattern.

Example 65

1-[5-(5-Chloro-thiophen-2-yl)-isoxazol-3-ylmethyl]-1H-imidazole-2-carboxylic acid (3,4,5,6-tetrahydro-2H-[1,4']bipyridinyl-4-yl)-amide Following the procedure from example 60 replacing 1-isopropyl-piperidin-4-ylamine by 3,4,5,6-tetrahydro-2H-[1,4']bipyridinyl-4-ylamine [prepared by adopting a procedure described in M. Nazare, M. Essrich, D. W. Will, H. Matter, K. Ritter, V. Wehner, Eur. Pat. Appl. (2003) EP 1314733 A1] in step (ii), 1-[5-(5-Chloro-thiophen-2-yl)-isoxazol-3-ylmethyl]-1H-imidazole-2-carboxylic ac (3,4,5,6-tetrahydro-2H-[1,4']bipyridinyl-4-yl)-amide was isolated after HPLC purification of the crude reaction mixture as its trifluoroacetate salt. MS (ESI+): m/e=469, chloro pattern.

Example 66

3-[5-(5-Chloro-thiophen-2-yl)-isoxazol-3-ylmethyl]-2-[2-(2-methoxy-ethoxy)-ethoxymethyl]-3H-imidazole-4-carboxylic acid (1-isopropyl-piperidin-4-yl)-amide (i) [2-(2-Methoxy-ethoxy)-ethoxy]-acetonitrile To a solution of 2-(2-methoxy-ethoxy)-ethanol (2.35 mL) in dry THF (25 mL) was added 870 mg of NaH (60% in mineral oil) portion wise at 0° C. The mixture was stirred for 30 min at RT and cooled again to 0° C. Tetra-n-butylammonium iodide (10 mg) was added followed by dropwise addition of a solution of bromoacetonitrile (1.33 mL) in dry THF (10 mL). The mixture was stirred for 3 h at RT, concentrated, taken up in saturated aqueous NH$_4$Cl solution and extracted with DCM. The organic phases were dried over anhydrous MgSO$_4$ and concentrated in vacuo to give crude [2-(2-methoxy-ethoxy)-ethoxy]-acetonitrile (2.60 g) as a brown oil. The product, still containing some mineral oil, was used directly in the next step.

(ii) N-Hydroxy-2-[2-(2-methoxy-ethoxy)-ethoxy]-acetamidine

To a solution of crude [2-(2-methoxy-ethoxy)-ethoxy]-acetonitrile (2.60 g) in MeOH (25 mL) was added hydroxylamine hydrochloride (1.11 g). The mixture was vigorously stirred while potassium tert-butoxide (1.79 g) was added portion wise. The mixture was stirred for 2 h at RT and then refluxed (1 h). After cooling to RT it was filtered. The filtrate was concentrated under reduced pressure, leaving crude N-hydroxy-2-[2-(2-methoxy-ethoxy)-ethoxy]-acetamidine. Yield: 3.02 g.

(iii) 3-({2-[2-(2-Methoxy-ethoxy)-ethoxy]-acetimidoyl}-aminooxy)-acrylic acid methyl ester To a vigorously stirred mixture of crude N-hydroxy-2-[2-(2-methoxy-ethoxy)-ethoxy]-acetamidine (3.02 g) and NEt$_3$ (2.30 mL) in DCM (40 mL) was added propynoic acid methyl ester (1.43 mL) dropwise. The mixture was stirred for 30 min at RT, washed with water, dried over anhydrous MgSO$_4$ and concentrated in vacuo. The residue, crude 3-({2-[2-(2-Methoxy-ethoxy)-ethoxy]-acetimidoyl}-aminooxy)-acrylic acid methyl ester (4.50 g) was directly used in the next step.

(iv) 2-[2-(2-Methoxy-ethoxy)-ethoxymethyl]-3H-imidazole-4-carboxylic acid methyl ester Crude 3-({2-[2-(2-Methoxy-ethoxy)-ethoxy]-acetimidoyl}-aminooxy)-acrylic acid methyl ester (4.50 g) was refluxed in 1,2-dichlorobenzene (20 mL) for 3 h. The solvent was removed under reduced pressure and the residue was purified by flash column chromatography on silica (DCM/MeOH 50:1->20:1) to give 2-[2-(2-Methoxy-ethoxy)-ethoxymethyl]-3H-imidazole-4-carboxylic acid methyl ester (907 mg) as a viscous brown oil. MS (ESI+): m/e=259.

(v) 2-[2-(2-Methoxy-ethoxy)-ethoxymethyl]-3H-imidazole-4-carboxylic acid

2-[2-(2-Methoxy-ethoxy)-ethoxymethyl]-3H-imidazole-4-carboxylic acid methyl ester (460 mg) and lithium hydroxide monohydrate (450 mg) in THF (3 mL) and water (1 mL) were stirred at 58° C. for 10 h. After cooling the mixture was carefully neutralized by the addition of 2 N HCl and concentrated to give crude 2-[2-(2-Methoxy-ethoxy)-ethoxymethyl]-3H-imidazole-4-carboxylic acid. Yield: 905 mg.

(vi) 2-[2-(2-Methoxy-ethoxy)-ethoxymethyl]-3H-imidazole-4-carboxylic acid (1-isopropyl-piperidin-4-yl)-amide To a solution of the foregoing crude carboxylic acid (905 mg) in DMF (10 mL) was added HATU (684 mg), followed by 1-isopropyl-piperidin-4-ylamine dihydrochloride (387 mg) and DIEA (620 µL). The mixture was stirred for 16 h at RT, diluted with water and extracted with DCM. The organic phases were dried over anhydrous MgSO$_4$ and concentrated in vacuo to give 2-[2-(2-Methoxy-ethoxy)-ethoxymethyl]-3H-imidazole-4-carboxylic acid (1-isopropyl-piperidin-4-yl)-amide. Yield: 629 mg.

(vii) 3-[5-(5-Chloro-thiophen-2-yl)-isoxazol-3-ylmethyl]-2-[2-(2-methoxy-ethoxy)-ethoxymethyl]-3H-imidazole-4-carboxylic acid (1-isopropyl-piperidin-4-yl)-amide A mixture of 2-[2-(2-Methoxy-ethoxy)-ethoxymethyl]-3H-imidazole-4-carboxylic acid (1-isopropyl-piperidin-4-yl)-amide (55 mg), 3-bromomethyl-5-(5-chloro-thiophen-2-yl)-isoxazole (46 mg), Cs$_2$CO$_3$ (98 mg), tetrabutylammonium iodide (8 mg) and DMF (3 mL) was stirred at 80° C. for 3 h. The solvent was removed in vacuo and the residue was taken up in DCM, washed with water, and the organic layer was dried over anhydrous MgSO$_4$ and concentrated. The title compound (6 mg) was isolated after HPLC purification of the residue as its trifluoroacetate salt. MS (ESI+): m/e=566 [M+H]$^+$, chloro pattern.

Example 67

1-[5-(5-Chloro-thiophen-2-yl)-isoxazol-3-ylmethyl]-2-methoxymethyl-1H-imidazole-4-carboxylic acid (2'-methanesulfonyl-biphenyl-4-yl)-amide The title compound was prepared analogously to example 10 with the difference that 1-2'-Methanesulfonyl-biphenyl-4-ylamine [prepared by adopting a procedure from Juraszyk, Horst; Dorsch, Dieter; Mederski, Werner; Tsaklakidis, Christos; Barnes, Christopher; Gleitz, Johannes; PCT Int. Appl. (2001), WO 0170678 A2] was used instead of 1-Isopropyl-piperidin-4-ylamine hydrochloride. MS (ES$^+$): m/e=583, chloro pattern.

Example 68

3-[2-(4-Chloro-phenyl)-ethyl]-2-[2-(2-methoxy-ethoxy)-ethoxymethyl]-3H-imidazole-4-carboxylic acid (1-isopropyl-piperidin-4-yl)-amide Following the procedure from example 66 replacing 3-bromomethyl-5-(5-chloro-thiophen-2-yl)-isoxazole by 1-chloro-4-(2-chloro-ethyl)-benzene in step (vii), 3-[2-(4-Chloro-phenyl)-ethyl]-2-[2-(2-methoxy-ethoxy)-ethoxymethyl]-3H-imidazole-4-carboxylic acid (1-isopropyl-piperidin-4-yl)-amide was isolated after HPLC purification of the crude reaction mixture as its trifluoroacetate salt. MS (ESI+): m/e=507 [M+H]$^+$, chloro pattern.

Example 69

3-[5-(5-Chloro-thiophen-2-yl)-isoxazol-3-ylmethyl]-2-(2-methoxy-ethoxymethyl)-3H-imidazole-4-carboxylic acid (1-isopropyl-piperidin-4-yl)-amide Following the procedure from example 66 replacing 2-(2-methoxy-ethoxy)-ethanol by 2-methoxy-ethanol in step (i), 3-[5-(5-Chloro-thiophen-2-yl)-isoxazol-3-ylmethyl]-2-(2-methoxy-ethoxymethyl)-3H-imidazole-4-carboxylic acid (1-isopropyl-piperidin-4-yl)-amide was isolated after HPLC purification of the crude reaction mixture as its trifluoroacetate salt. MS (ESI+): m/e=522 [M+H]$^+$, chloro pattern.

Example 70

3-[(5-Chloro-pyridin-2-ylcarbamoyl)-methyl]-2-(2-methoxy-ethoxymethyl)-3H-imidazole-4-carboxylic acid (1-isopropyl-piperidin-4-yl)-amide To a solution of 49 mg of 2-(2-Methoxy-ethoxymethyl)-3H-imidazole-4-carboxylic acid (1-isopropyl-piperidin-4-yl)-amide [prepared by following the procedure from example 66 replacing 2-(2-methoxy-ethoxy)-ethanol by 2-methoxy-ethanol in step (i)] in DMF (3 mL) was added 17 mg of sodium hydride (60% in mineral oil). The mixture was stirred at 50° C. for 1 h and cooled to 30° C. 2-Bromo-N-(5-chloro-pyridin-2-yl)-acetamide (41 mg) was added and stirring was continued for 1.5 h. Another portion of 2-bromo-N-(5-chloro-pyridin-2-yl)-acetamide (10 mg) was added. The mixture was stirred for 30 min at 30° C., carefully quenched by dropwise addition of water and extracted with ethyl acetate. The combined organic phases were washed with water and brine, dried over anhydrous MgSO$_4$ and concentrated in vacuo. The title compound (16 mg) was isolated after HPLC purification of the residue as its trifluoroacetate salt. MS (ESI+): m/e=493 [M+H]$^+$, chloro pattern.

Example 71

3-[5-(5-Chloro-thiophen-2-yl)-isoxazol-3-ylmethyl]-2-(perhydro-1,4-oxazepine-4-carbonyl)-3H-imidazole-4-carboxylic acid (1-isopropyl-piperidin-4-yl)-amide (i) 3-[5-(5-Chloro-thiophen-2-yl)-isoxazol-3-ylmethyl]-2-hydrazinocarbonyl-3H-imidazole-4-carboxylic acid tert-butyl ester To a solution of 438 mg of 1-[5-(5-Chloro-thiophen-2-yl)-isoxazol-3-ylmethyl]-1H-imidazole-2,5-diacarboxylic acid 4-tert-butyl ester 2-ethyl ester (see example1) in MeOH (8 mL) was added 228 µL of hydrazine (80% solution in water). The mixture was stirred for 1.5 h at 50° C. A solid precipitated which was collected, triturated with a mixture of 2-propanol and water (2:1, 5 mL) and dried for 2 h at 30° C. and 20 mbar to provide) 3-[5-(5-Chloro-thiophen-2-yl)-isoxazol-3-ylmethyl]-2-hydrazinocarbonyl-3H-imidazole-4-carboxylic acid tert-butyl ester (397 mg) which was used in the next step without further purification.

(ii) 3-[5-(5-Chloro-thiophen-2-yl)-isoxazol-3-ylmethyl]-2-([1,4]oxazepane-4-carbonyl)-3H-imidazole-4-carboxylic acid To a solution of 3-[5-(5-Chloro-thiophen-2-yl)-isoxazol-3-ylmethyl]-2-hydrazinocarbonyl-3H-imidazole-4-carboxylic acid tert-butyl ester (119 mg) in dry DCM (4 mL) was added nitrosyl tetrafluoroborate (36 mg). The mixture was stirred for 5 min at −40° C., then warmed to 0° C. and stirring was continued for 1.5 h at 0° C. The reaction was quenched by the addition of aqueous 0.1 N NaHCO$_3$ solution. The phases were separated and the aqueous phase was extracted two times with DCM. The combined organic layers were dried over MgSO4 and concentrated to a volume of 3 mL. To this solution containing 2-azidocarbonyl-3-[5-(5-chloro-thiophen-2-yl)-isoxazol-3-ylmethyl]-3H-imidazole-4-carboxylic acid tert-butyl ester was added a solution of 31 mg of [1,4]oxazepane (homomorpholine) in DCM (4 mL) dropwise. The mixture was stirred for 1.5 h, concentrated under reduced pressure and taken up again in DCM (4 mL).

To the resulting solution containing 3-[5-(5-Chloro-thiophen-2-yl)-isoxazol-3-ylmethyl]-2-([1,4]oxazepane-4-carbonyl)-3H-imidazole-4-carboxylic acid tert-butyl ester was added TFA (216 µL). The mixture was stirred for 3 h at RT and for 3 h at 40° C. More TFA (1 mL) was added and stirring was continued at 50° C. for 2 h. The mixture was concentrated under reduced pressure. The residue was evaporated three times from toluene to provide crude 3-[5-(5-Chloro-thiophen-2-yl)-isoxazol-3-ylmethyl]-2-([1,4]oxazepane-4-carbonyl)-3H-imidazole-4-carboxylic acid (311 mg) which was directly used in the next step.

(iii) 3-[5-(5-Chloro-thiophen-2-yl)-isoxazol-3-ylmethyl]-2-(perhydro-1,4-oxazepine-4-carbonyl)-3H-imidazole-4-carboxylic acid (1-isopropyl-piperidin-4-yl)-amide To a solution of the foregoing carboxylic acid (311 mg) in DMF (4 mL) was added HATU (128 mg), followed by 1-isopropyl-piperidin-4-ylamine dihydrochloride (67 mg) and DIEA (245 µL). The mixture was stirred for 2.5 h at RT and for 1.5 h at 45° C., concentrated under reduced pressure and the residue was purified by HPLC to provide 3-[5-(5-Chloro-thiophen-2-yl)-isoxazol-3-ylmethyl]-2-(perhydro-1,4-oxazepine-4-carbonyl)-3H-imidazole-4-carboxylic acid (1-isopropyl-piperidin-4-yl)-amide as its trifluoroacetate salt. Yield: 18 mg; MS (ESI+): m/e=561 [M+H]$^+$, chloro pattern.

EXPERIMENTALS

Pharmacological Testing

The ability of the compounds of the formula I to inhibit factor Xa or factor VIIa or other enzymes like thrombin, plasmin, or trypsin can be assessed by determining the concentration of the compound of the formula I that inhibits enzyme activity by 50%, i. e. the IC50 value, which was related to the inhibition constant Ki. Purified enzymes were used in chromogenic assays. The concentration of inhibitor that causes a 50% decrease in the rate of substrate hydrolysis was determined by linear regression after plotting the relative rates of hydrolysis (compared to the uninhibited control) versus the log of the concentration of the compound of formula I. For calculating the inhibition constant Ki, the IC50 value was corrected for competition with substrate using the formula $Ki=IC50/\{1+(\text{substrate concentration}/Km)\}$ wherein Km is the Michaelis-Menten constant (Chen and Prusoff, Biochem. Pharmacol. 22 (1973), 3099-3108; I. H. Segal, Enzyme Kinetics, 1975, John Wiley & Sons, New York, 100-125; which were incorporated herein by reference).

a) Factor Xa Assay

In the assay for determining the inhibition of factor Xa activity TBS-PEG buffer (50 mM Tris-HCl, pH 7.8, 200 mM NaCl, 0.05% (w/v) PEG-8000, 0.02% (w/v) NaN3) was used. The IC50 was determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-PEG (uninhibited control) or various concentrations of the compound to be tested diluted in 10% (v/v) DMSO in TBS-PEG; and substrate S-2765 (N(α)-benzyloxycarbonyl-D-Arg-Gly-L-Arg-p-nitroanilide; Kabi Pharmacia, Inc.; Franklin, Ohio) in TBS-PEG.

The assay was performed by pre-incubating the compound of formula I plus enzyme for 10 min. Then the assay was initiated by adding substrate to obtain a final volume of 100 µl. The initial velocity of chromogenic substrate hydrolysis was measured by the change in absorbance at 405 nm using a Bio-tek Instruments kinetic plate reader (Ceres UV900HDi) at 25° C. during the linear portion of the time course (usually 1.5 min after addition of substrate). The enzyme concentration was 0.5 nM and substrate concentration was 140 µM.

b) Factor VIIa Assay

The inhibitory activity towards factor VIIa/tissue factor activity was determined using a chromogenic assay essentially as described previously (J. A. Ostrem et al., Biochemistry 37 (1998) 1053-1059 which was incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 µl human factor VIIa and TF (5 nM and 10 nM, respectively final concentration) combined with 40 µl of inhibitor dilutions in 10% DMSO/TBS-PEG buffer (50 mM Tris, 15 mM NaCl, 5 mM CaCl$_2$, 0.05% PEG 8000, pH 8.15). Following a 15-minutes pre-incubation period, the assay was initiated by the addition of 35 µl of the chromogenic substrate S-2288 (D-Ile-Pro-Arg-p-nitroanilide, Pharmacia Hepar Inc., 500 µM final concentration). The results (inhibition constants Ki (FXa) for inhibition of factor Xa) are shown in Table 1.

TABLE 1

| Example | Ki(FXa) [µM] |
|---|---|
| 1 | 0.065 |
| 3 | 0.007 |
| 5 | 0.027 |
| 6 | 0.530 |
| 7 | 0.001 |

TABLE 1-continued

| Example | Ki(FXa) [µM] |
|---|---|
| 9 | 0.086 |
| 11 | 0.004 |
| 12 | 0.018 |
| 14 | 0.401 |
| 15 | 0.056 |
| 16 | 0.254 |
| 17 | 0.112 |
| 18 | 0.007 |
| 20 | 0.358 |
| 21 | 0.243 |
| 23 | 0.006 |
| 24 | 0.022 |
| 26 | 0.003 |
| 29 | 0.140 |
| 30 | 0.035 |
| 33 | 0.103 |
| 37 | 0.008 |
| 38 | 0.174 |
| 39 | 0.117 |
| 40 | 0.020 |
| 41 | 0.046 |
| 42 | 0.126 |
| 43 | 0.062 |
| 44 | 0.136 |
| 45 | 0.057 |
| 46 | 0.128 |
| 47 | 0.077 |
| 48 | 0.091 |
| 49 | 0.037 |
| 60 | 0.049 |
| 63 | 0.640 |
| 65 | 0.118 |
| 71 | 0.051 |

We claim:

1. A compound of the formula Ib,

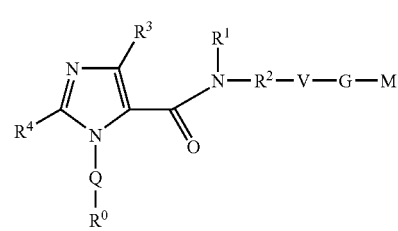

wherein,

R⁰ is
isoxazol-3-yl, which is unsubstituted or mono-, di- or trisubstituted independently of one another by R8, and which is additionally substituted by a monocyclic or bicyclic 4- to 15-membered heterocyclyl, containing one, two, three or four heteroatoms chosen from the group consisting of nitrogen, sulfur or oxygen, wherein, said heterocyclyl is unsubstituted or mono-, di- or trisubstituted independently of one another by R8;

R8 is 1) halogen,
2) —NO$_2$,
3) —CN,
4) —C(O)—NH$_2$,
5) —OH,
6) —NH$_2$,
7) —O—CF$_3$ 8) a monocyclic or bicyclic 6- to 14-membered aryl, wherein aryl is mono-, di- or trisubstituted independently of one another by halogen or —O—$(C_1-C_8)$-alkyl,
9) —$(C_1-C_8)$-alkyl, wherein alkyl is unsubstituted or mono-, di- or trisubstituted independently of one another by halogen, $NH_2$, —OH or a methoxy residue,
10) —O—$(C_1-C_8)$-alkyl, wherein alkyl is unsubstituted or mono-, di- or trisubstituted independently of one another by halogen, $NH_2$, —OH or a methoxy residue,
11) —$SO_2$—$CH_3$ or
12) —$SO_2$—$CF_3$, Q is methylene;

$R^1$ is hydrogen, —$(C_1-C_4)$-alkyl, wherein alkyl is unsubstituted or substituted one to three times by R13; —$(C_1-C_3)$-alkylene-C(O)—NH—$R^0$, —$(C_1-C_3)$-alkylene-C(O)—O—R10, a monocyclic or bicyclic 6- to 14-membered aryl, wherein aryl is mono-, di- or trisubstituted independently of one another by R8, a monocyclic or bicyclic 4- to 15-membered heterocyclyl, containing one, two, three or four heteroatoms chosen from nitrogen, sulfur or oxygen; —$(C_1-C_3)$-perfluoroalkyl,
—$(C_1-C_3)$-alkylene-S(O)—$(C_1-C_4)$-alkyl, —$(C_1-C_3)$-alkylene-S(O)$_2$—$(C_1-C_3)$-alkyl, —$(C_1-C_3)$-alkylene-S(O)$_2$—N($R^{4'}$)—$R^{5'}$, —$(C_1-C_3)$-alkylene-O—$(C_1-C_4)$-alkyl, —$(C_0-C_3)$-alkylene-$(C_3-C_8)$-cycloalkyl, or —$(C_0-C_3)$-alkylene-het, wherein het is unsubstituted or mono-, di- or trisubstituted independently of one another by R14, wherein $R^{4'}$ and $R^{5'}$ are independent of one another are identical or different and are hydrogen or —$(C_1-C_4)$-alkyl;

$R^2$ is a direct bond or —$(C_1-C_4)$-alkylene, or $R^1$ and $R^3$ together with the atoms to which they are bonded can form a 6- to 8-membered cyclic group, containing 1, 2, 3 or 4 heteroatoms chosen from nitrogen, sulfur or oxygen, wherein, said cyclic group is unsubstituted or mono-, di- or trisubstituted independently of one another by R14; or $R^1$—N—$R^2$—V form a 4- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, R14 is halogen, —OH, =O, —$(C_1-C_8)$-alkyl, —$(C_1-C_4)$-alkoxy, —$NO_2$, —$(C_0-C_4)$-alkyl-C(O)—O—$R^{18}$, —CN, —$(C_0-C_4)$-alkyl-N($R^{18}$)—$R^{21}$, —$(C_0-C_4)$-alkyl-O—$R^{18}$, —$(C_0-C_4)$-alkyl-het, —$(C_0-C_8)$-alkyl-$SO_2$, —$SO_2$—$(C_1-C_4)$-alkyl, —$SO_2$—N($R^{18}$)—$R^{21}$, —C(O)—NH—$(C_1-C_8)$-alkyl, —C(O)—N—[$(C_1-C_8)$-alkyl]$_2$, —$NR^{18}$—C(O)—NH—$(C_1-C_8)$-alkyl, —C(O)—$NH_2$, —S—$R^{18}$, or —$NR^{18}$—C(O)—NH—[$(C_1-C_8)$-alkyl]$_2$,
wherein $R^{18}$ and $R^{21}$ are independently from each other hydrogen atom, —$(C_1-C_3)$-perfluoroalkyl or —$(C_1-C_6)$-alkyl;

V is 1) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14,
2) a 6- to 14-membered aryl, wherein aryl is unsubstituted or mono-, di- or trisubstituted independently of one another by R14, or
3) a monocyclic or bicyclic 4- to 15-membered heterocyclyl, wherein said heterocyclyl is unsubstituted or mono-, di- or trisubstituted independently of one another by R14;

G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_n$— or —$(CH_2)_m$—$NR^{10}$—C(O)—O—$(CH_2)_n$—;

n and m are independently of one another identical or different and are the integers zero, 1, 2, 3, 4, 5 or 6;

M is 1) a hydrogen,
2) —$(C_1-C_8)$-alkyl, wherein alkyl is unsubstituted or mono-, di- or trisubstituted independently of one another by R14,
3) —C(O)—N(R11)-R12,
4) —$(CH_2)_m$—$NR^{10}$,
5) a 6- to 14-membered aryl, wherein aryl is unsubstituted or mono-, di- or trisubstituted independently of one another by R14,
6) a monocyclic or bicyclic 4- to 15-membered heterocyclyl, wherein heterocyclyl is unsubstituted or mono-, di- or trisubstituted independently of one another by R14,
7) —$(C_3-C_8)$-cycloalkyl, wherein said cycloalkyl is unsubstituted or mono-, di- or trisubstituted independently of one another by R14, or
8) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14;

$R^3$ and $R^4$ are independent of one another are identical or different and are
1) hydrogen,
2) halogen,
3) —$(C_1-C_4)$-alkyl, wherein alkyl is unsubstituted or mono-, di- or trisubstituted independently of one another by R13,
4) —$(C_1-C_3)$-perfluoroalkyl,
5) phenyl, wherein phenyl is unsubstituted or mono-, di- or trisubstituted independently of one another by R13,
6) —$(C_0-C_4)$-alkylene-O—R19, wherein R19 is
  a) hydrogen,
  b) —$(C_1-C_4)$-alkyl, wherein alkyl is unsubstituted or mono-, di- or trisubstituted independently of one another by R13, or
  c) phenyl, wherein phenyl is unsubstituted or mono-, di- or trisubstituted independently of one another by R13,
  d) —$CF_3$, or
  e) —$CHF_2$,
7) —$NO_2$,
8) —CN,
9) —$SO_s$—$R^{11}$, wherein s is 1 or 2,
10) —$SO_t$—N($R^{11}$)—$R^{12}$, wherein t is 1 or 2,
11) —$(C_0-C_4)$-alkylene-C(O)—$R^{11}$,
12) —$(C_0-C_4)$-alkylene-C(O)—O—$R^{11}$,
13) —$(C_0-C_4)$-alkylene-C(O)—N($R^{11}$)—$R^{12}$,
14) —$(C_0-C_4)$-alkylene-N($R^{11}$)—$R^{12}$,
15) —$NR^{10}$—$SO_2$—$R^{10}$, 16) —S—R$^{10}$,
17) —(C$_0$-C$_2$)alkylene-C(O)—O—(C$_2$-C$_4$)-alkylene-O—C(O)—(C$_1$-C$_4$)-alkyl,
18) —C(O)—O—C(R15, R16)-O—C(O)—R17,
19) —(C$_0$-C$_2$)alkylene-C(O)—O—(C$_2$-C$_4$)-alkylene-O—C(O)—O—(C$_1$-C$_6$)-alkyl,
20) —C(O)—O—C(R15, R16)-O—C(O)—O—R17,
21) —(C$_0$-C$_4$)-alkylene-(C$_6$-C$_{14}$)-aryl, wherein aryl is mono-, di- or trisubstituted independently of one another by R13,
22) —(C$_0$-C$_4$)-alkylene-(C$_4$-C$_{15}$)-heterocyclyl, wherein heterocyclyl is unsubstituted or mono-, di- or trisubstituted independently of one another by R13
23) —(C$_0$-C$_4$)-alkylene-(C$_3$-C$_8$)-cycloalkyl, wherein cycloalkyl is unsubstituted or mono-, di- or trisubstituted independently of one another by R13,
24) —(C$_0$-C$_4$)-alkylene-het, wherein het is unsubstituted or mono-, di- or trisubstituted independently of one another by R13,
25) —(C$_0$-C$_4$)-alkylene-O—CH$_2$—(C$_1$-C$_3$)-perfluoroalkylene-CH$_2$—O—(C$_0$-C$_4$)-alkyl, or
26) a residue selected from the group consisting of

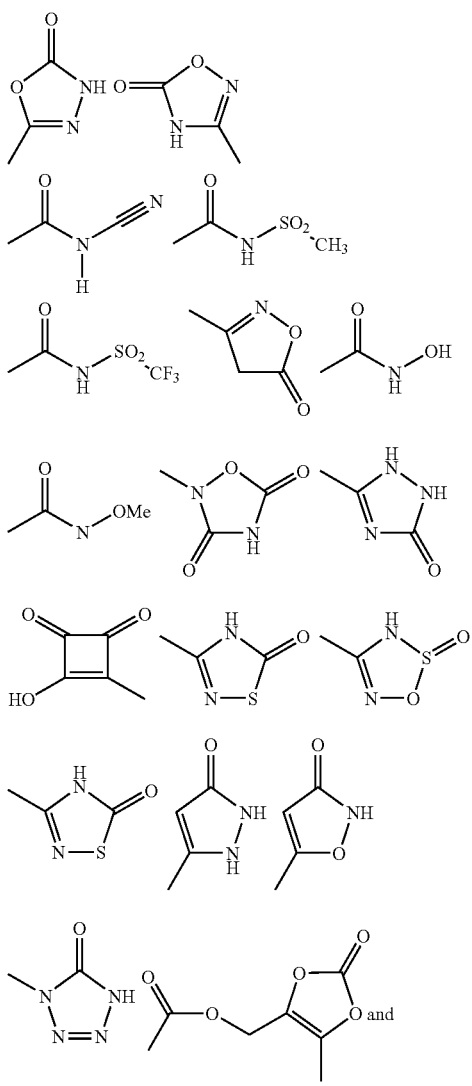

-continued

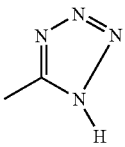

wherein Me is methyl, or two —OR19 residues and adjacent atoms through which they are attached form together a 5- or 6-membered ring, that is unsubstituted or substituted one, two, three or four times by R13;

R11 and R12 are independently of one another identical or different and are
1) hydrogen,
2) —(C$_1$-C$_6$)-alkyl, wherein alkyl is unsubstituted or mono-, di- or trisubstituted independently of one another by R13,
3) —(C$_0$-C$_6$)-alkyl-(C$_3$-C$_8$)-cycloalkyl,
4) —SO$_t$—R$^{10}$, wherein t is 1 or 2,
5) —(C$_0$-C$_6$)-alkyl-(C$_6$-C$_{14}$)-aryl, wherein alkyl and aryl independently from one another are unsubstituted or mono-, di- or trisubstituted by R13,
6) —(C$_1$-C$_3$)-perfluoroalkyl,
7) —O—R$^{17}$, or
8) —(C$_0$-C$_6$)-alkyl-(C$_4$-C$_{15}$)-heterocyclyl, wherein alkyl and heterocyclyl independently from one another are unsubstituted or mono-, di- or trisubstituted by R13, or R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13;

R13 is halogen, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_8$)-cycloalkyl, —(C$_0$-C$_3$)-alkylene-O—R$^{10}$, —Si—(CH$_3$)$_3$, —N(R$^{10}$)—S(O)$_u$—R$^{10}$, wherein u is 1 or 2, —S—R$^{10}$, —SO$_r$—R$^{10}$, wherein r is 1 or 2, —S(O)$_v$—N(R$^{10}$)—R$^{20}$, wherein v is 1 or 2, —C(O)—R$^{10}$, —(C$_1$-C$_8$)-alkyl, —(C$_1$-C$_8$)-alkoxy, phenyl, phenyloxy-, —O—CF$_3$, —(C$_0$-C$_4$)-alkyl-C(O)—O—C(R15, R16)-O—C(O)—R17, —(C$_1$-C$_4$)-alkoxy-phenyl, —(C$_0$-C$_4$)-alkyl-C(O)—O—C(R15, R16)-O—C(O)—O—R17, —(C$_1$-C$_3$)-perfluoroalkyl, —O—R15, —NH—C(O)—NH—R$^{10}$, —NH—C(O)—O—R$^{10}$, or a residue selected from the group consisting of

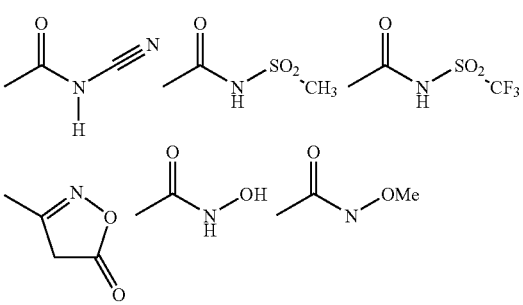

-continued

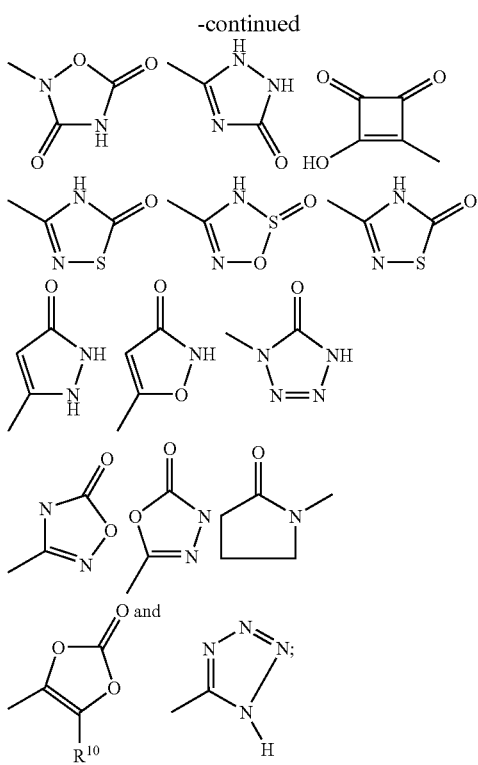

$R^{10}$ and $R^{20}$ are independently of one another hydrogen, —$(C_1$-$C_6)$-alkyl, —$(C_0$-$C_4)$-alkyl-OH, —$(C_0$-$C_4)$-alkyl-O—$(C_1$-$C_4)$-akyl or —$(C_1$-$C_3)$-perfluoroalkyl;

R15 and R16 are independently of one another hydrogen, —$(C_1$-$C_6)$-alkyl, or together with the carbon atom to which they are bonded they can form a 3- to 6 membered carbocyclic ring which is unsubstituted or substituted one to three times by $R^{10}$; and R17 is —$(C_1$-$C_6)$-alkyl, —$(C_1$-$C_6)$-alkyl-OH, —$(C_1$-$C_6)$-alkyl-O—$(C_1$-$C_6)$-alkyl, —$(C_3$-$C_8)$-cycloalkyl, —$(C_1$-$C_6)$-alkyl-O—$(C_1$-$C_8)$-alkyl-$(C_3$-$C_8)$-cycloalkyl, —$(C_1$-$C_6)$-alkyl-$(C_3$-$C_8)$-cycloalkyl, wherein said cycloalkyl ring is unsubstituted or substituted one, two or three times by —OH, —O—$(C_1$-$C_4)$-alkyl or $R^{10}$; or a stereoisomeric form or a mixture thereof in any ratio, or a physiologically tolerable salt thereof.

2. A compound according to claim 1, which is:
3-[5-(5-Chloro-thiophen-2-yl)-isoxazol-3-ylmethyl]-3H-imidazole-4-carboxylic acid (1-isopropyl-piperidin-4-yl)-amide;
5-Chloro-3-[5-(5-chloro-thiophen-2-yl)-isoxazol-3-ylmethyl]-2-phenyl-3H-imidazole-4-carboxylic acid (1-isopropyl-piperidin-4-yl)-amide;
3-[5-(5-Chloro-thiophen-2-yl)-isoxazol-3-ylmethyl]-5-methyl-3H-imidazole-4-carboxylic acid (1-isopropyl-piperidin-4-yl)-amide;
3-[5-(5-Chloro-thiophen-2-yl)-isoxazol-3-ylmethyl]-2-ethyl-5-methyl-3H-imidazole-4-carboxylic acid (1-isopropyl-piperidin-4-yl)-amide;
3-[5-(5-Chloro-thiophen-2-yl)-isoxazol-3-ylmethyl]-2-iodo-5-methyl-3H-imidazole-4-carboxylic acid (1-isopropyl-piperidin-4-yl)-amide;
3-[5-(5-Chloro-thiophen-2-yl)-isoxazol-3-ylmethyl]-2-methoxymethyl-3H-imidazole-4-carboxylic acid (1-isopropyl-piperidin-4-yl)-amide;
3-[5-(5-Chloro-thiophen-2-yl)-isoxazol-3-ylmethyl]-2-cyclopropyl-3H-imidazole-4-carboxylic acid (1-isopropyl-piperidin-4-yl)-amide;
3-[5-(5-Chloro-thiophen-2-yl)-isoxazol-3-ylmethyl]-2-(2,6-difluoro-phenyl)-3H-imidazole-4-carboxylic acid (1-isopropyl-piperidin-4-yl)-amide;
3-[5-(5-Chloro-thiophen-2-yl)-isoxazol-3-ylmethyl]-2-cyclopentyl-3H-imidazole-4-carboxylic acid (1-isopropyl-piperidin-4-yl)-amide;
3-[5-(5-Chloro-thiophen-2-yl)-isoxazol-3-ylmethyl]-2-(2-methoxy-ethyl)-3H-imidazole-4-carboxylic acid (1-isopropyl-piperidin-4-yl)-amide;
3-[5-(5-Chloro-thiophen-2-yl)-isoxazol-3-ylmethyl]-2-(2,6-dichloro-phenyl)-3H-imidazole-4-carboxylic acid (1-isopropyl-piperidin-4-yl)-amide;
3-[5-(5-Chloro-thiophen-2-yl)-isoxazol-3-ylmethyl]-2-isopropyl-3H-imidazole-4-carboxylic acid (1-isopropyl-piperidin-4-yl)-amide;
3-[5-(5-Chloro-thiophen-2-yl)-isoxazol-3-ylmethyl]-2-pyridin-2-yl-3H-imidazole-4-carboxylic acid (1-isopropyl-piperidin-4-yl)-amide;
3-[5-(5-Chloro-thiophen-2-yl)-isoxazol-3-ylmethyl]-5-methyl-2-phenyl-3H-imidazole-4-carboxylic acid (1-isopropyl-piperidin-4-yl)-amide;
3-[5-(5-Chloro-thiophen-2-yl)-isoxazol-3-ylmethyl]-2-pyridin-3-yl-3H-imidazole-4-carboxylic acid (1-isopropyl-piperidin-4-yl)-amide;
3-[5-(5-Chloro-thiophen-2-yl)-isoxazol-3-ylmethyl]-2-(2-methyl-thiazol-4-y)-3H-imidazole-4-carboxylic acid (1-isopropyl-piperidin-4-yl)-amide;
3-[5-(5-Chloro-thiophen-2-yl)-isoxazol-3-ylmethyl]-2-ethanesulfonyl-3H-imidazole-4-carboxylic acid (1-isopropyl-piperidin-4-yl)-amide;
3-[5-(5-Chloro-thiophen-2-yl)-isoxazol-3-ylmethyl]-5-methyl-3H-imidazole-2,4-dicarboxylic acid 2-amide 4-[(1-isopropyl-piperidin-4-yl)-amide];
2-Bromo-3-[5-(5-chloro-thiophen-2-yl)-isoxazol-3-ylmethyl]-5-methyl-3H-imidazole-4-carboxylic acid (1-isopropyl-piperidin-4-yl)-amide;
3-[5-(5-Chloro-thiophen-2-yl)-isoxazol-3-ylmethyl]-2-(2-methoxy-phenyl)-5-methyl-3H-imidazole-4-carboxylic acid (1-isopropyl-piperidin-4-yl)-amide;
3-[5-(5-Chloro-thiophen-2-yl)-isoxazol-3-ylmethyl]-2-(3-trifluoromethyl-phenyl)-3H-imidazole-4-carboxylic acid (1-isopropyl-piperidin-4-yl)-amide;
1-[5-(5-Chloro-thiophen-2-yl)-isoxazol-3-ylmethyl]-5-(1-isopropyl-piperidin-4-ylcarbamoyl)-1H-imidazole-2-carboxylic acid ethyl ester;
3-[5-(5-Chloro-thiophen-2-yl)-isoxazol-3-ylmethyl]-2-[2-(2-methoxy-ethoxy)-ethoxymethyl]-3H-imidazole-4-carboxylic acid (1-isopropyl-piperidin-4-yl)-amide;
3-[5-(5-Chloro-thiophen-2-yl)-isoxazol-3-ylmethyl]-2-(2-methoxy-ethoxymethyl)-3H-imidazole-4-carboxylic acid (1-isopropyl-piperidin-4-yl)-amide; or
3-[5-(5-Chloro-thiophen-2-yl)-isoxazol-3-ylmethyl]-2-(perhydro-1,4-oxazepine-4-carbonyl)-3H-imidazole-4-carboxylic acid (1-isopropyl-piperidin-4-yl)-amide.

3. The compound according to claim 1, wherein,
$R^0$ is isoxazol-3-yl, which is substituted by a residue selected from the group consisting of thienyl, 2-thienyl and 3-thienyl, wherein said residue is unsubstituted or mono- or disubstituted independently of one another by R8;
R8 is fluorine, chlorine or bromine;
Q is methylene;
$R^1$ is hydrogen;
$R^2$ is a direct bond or methylene;

V is 1) a residue selected from the group consisting of azaindolyl, 1H-pyrrolopyridyl, azetidine, 1,4-diazepane, isoxazole, isoquinoline, piperazine, piperidine, pyrazine, pyridazine, pyrimidine, pyrrolidine, quinazoline, quinoline or tetrahydropyrane,
wherein said residue is unsubstituted or mono- or disubstituted independently of one another by R14, or
2) phenyl, that is unsubstituted or mono- or disubstituted independently or one another by R14; or
$R^1$—N—$R^2$—V forms azetidine, pyrrolidine, piperidine or piperazine;
R14 is fluorine, chlorine, methyl, ethyl, —$NH_2$ or —$SO_2$—$CH_3$;
G is a direct bond;
M is a residue selected from the group consisting of hydrogen, ($C_2$-$C_4$)-alkyl, azepanyl, cyclopropyl, cyclobutyl, cyclopentyl, cyclohexyl, imidazolyl, ketomorpholinyl, morpholinyl, [1,4]oxazepanyl, phenyl, piperidinyl, piperidonyl, pyrazinyl, pyrazolyl, pyridazinyl, pyridinyl, pyrimidyl, pyrrolidinyl, 1,4,5,6-tetrahydro-pyridazinyl, and tetrahydropyranyl, wherein said residue is unsubstituted or mono- or disubstituted independently of one another by R14;
$R^3$ and $R^4$ are independent of one another, are identical or different, and are
1) hydrogen,
2) fluorine or chlorine,
3) —($C_1$-$C_4$)-alkyl, wherein said alkyl is unsubstituted or mono-, di- or trisubstituted independently of one another by R13,
4) —($C_1$-$C_3$)-perfluoroalkyl,
5) phenyl wherein said phenyl is unsubstituted or mono-, di- or trisubstituted, independently of one another, by R13,
6) —($C_0$-$C_2$)-alkylene-O—R19, wherein R19 is
 a) hydrogen,
 b) —($C_1$-$C_4$-alkyl, wherein said alkyl is unsubstituted or mono-, di- or trisubstituted independently of one another, by R13, or
 c) phenyl, wherein phenyl is unsubstituted or mono-, di- or trisubstituted, independently of one another, by R13,
 d) —$CF_3$, or
 e) —$CHF_2$,
8) —CN,
9) —$SO_s$—$R^{11}$, wherein s is 1 or 2,
10) —$SO_t$—N($R^{11}$)—$R^{12}$, wherein t is 1 or 2,
11) —($C_0$-$C_4$)-alkylene-C(O)—$R^{11}$,
12) —($C_0$-$C_4$)-alkylene-C(O)—O—$R^{11}$,
13) —($C_0$-$C_4$)-alkylene-C(O)—N($R^{11}$)—$R^{12}$,
14) —($C_0$-$C_4$)-alkylene-N($R^{11}$)—$R^{12}$,
15) —$NR^{10}$—$SO_2$—$R^{10}$,
17) —($C_0$-$C_2$)-alkylene-C(O)—O—($C_2$-$C_4$)-alkylene-O—C(O)—($C_1$-$C_4$)-alkyl,
18) —C(O)—O—C(R15, R16)-O—C(O)—R17,
19) —($C_0$-$C_2$)alkylene-C(O)—O—($C_2$-$C_4$)-alkylene-O—C(O)—O—($C_1$-$C_6$)-alkyl,
20) —C(O)—O—C(R15, R16)-O—C(O)—O-R17,
23) —($C_0$-$C_3$)-alkylene-($C_3$-$C_6$)-cycloalkyl, or —($C_0$-$C_4$)-alkylene-($C_3$-$C_6$)-cycloalkyl, that is unsubstituted or mono-, di- or trisubstituted, independently of one another, by R13,
24) het, wherein said het is pyridyl or thiazolyl, that is unsubstituted or mono-, di- or trisubstituted, independently of one another, by R13, or
25) —($C_0$-$C_3$)-alkylene-O—$CH_2$—$CF_2$—$CH_2$—O—($C_0$-$C_3$)-alkyl, —($C_0$-$C_3$)-alkylene-O—$CH_2$—$CF_2$—$CF_2$—$CH_2$—O—($C_0$-$C_3$)-alkyl, or —($C_0$-$C_3$)-alkylene-O—$CH_2$—($C_1$-$C_3$)-perfluoroalkylene-$CH_2$—OH, or
26) a residue selected from the group consisting of

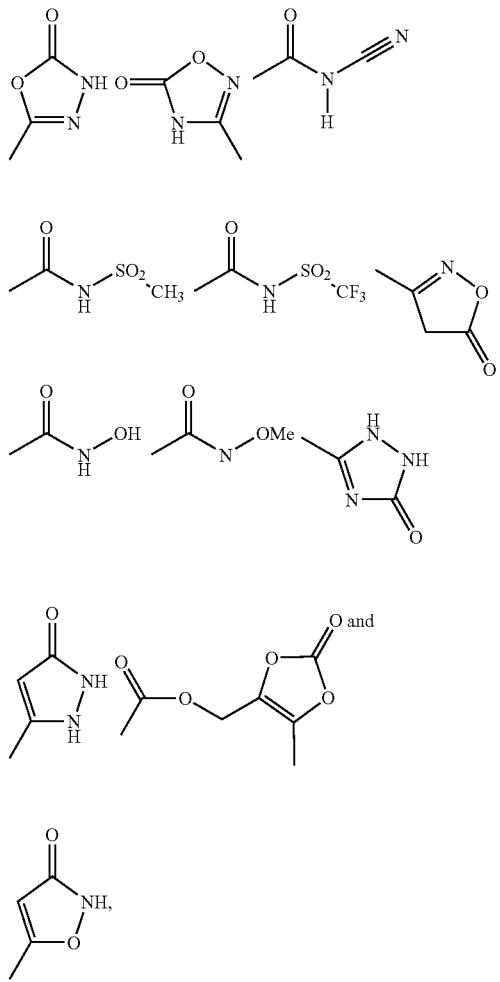

wherein Me is methyl;
R11 and R12 are, independently of one another, identical or different and are
1) hydrogen,
2) —($C_1$-$C_4$)-alkyl wherein alkyl is unsubstituted or mono-, di- or trisubstituted, independently of one another, by R13,
3) —($C_0$-$C_6$-alkyl-($C_3$-$C_6$)-cycloalkyl,
7) —O—$R^{17}$, or
8) —($C_0$-$C_6$)-alkyl-heterocyclyl, wherein alkyl and heterocyclyl, independently from one another, are unsubstituted or mono-, di- or trisubstituted by R13 and wherein heterocyclyl is azetidine, imidazolidine, morpholine, (1,4)-oxazepane or pyrrolidine, or
R11 and R12, together with the nitrogen atom to which they are bonded, form azetidine, imidazolidine, morpholine, (1,4)-oxazepane, 1,4-oxazepine, piperazine, piperidine, pyrrolidine or thiomorpholine;
R13 is fluorine, chlorine, —CN, =O, —OH, —$CF_3$, —C(O)—O—$R^{10}$, —C(O)—N($R^{10}$)—$R^{20}$, —N($R^{10}$)—$R^{20}$, —($C_3$-$C_6$)-cycloalkyl, —($C_0$-$C_3$)-alkylene-O—$R^{10}$, —Si—$(CH_3)_3$, —S—$R^{10}$, —$SO_2$—

$R^{10}$, —($C_1$-$C_4$)-alkyl, —($C_1$-$C_3$)perfluoroalkyl, or a residue selected from the group consisting of

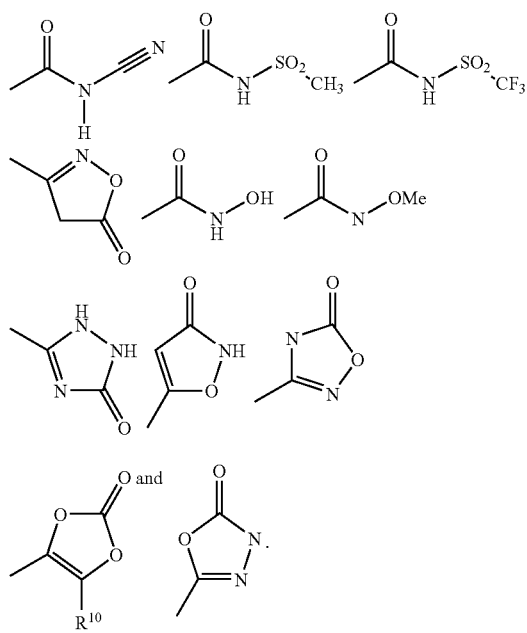

wherein Me is methyl;

$R^{10}$ and $R^{20}$ are, independently of one another, hydrogen, —($C_1$-$C_4$)-alkyl, or —($C_1$-$C_3$)-perfluoroalkyl; and $R^{15}$ and $R^{16}$ are, independently of one another, hydrogen, —($C_1$-$C_4$)-alkyl, or together form cyclopropyl, cyclobutyl, cyclopentyl or cyclohexyl, wherein each ring is unsubstituted or substituted one to three times by $R^{10}$, or a steremsomeric form or a mixture thereof in any ratio, or a physiologically tolerable salt thereof.

4. A pharmaceutical preparation, comprising at least one compound of the formula I according to claim 1 or a stereoisomeric form or a mixtures thereof in any ratio, or a physiologically tolerable salt thereof, and a pharmaceutically acceptable carrier.

5. A process for the preparation of a compound according to claim 1 comprising condensing a compound of the formula 29 with a compound of formula $HR^{8'}$ to give a compound of formula 30 and converting the compound of formula 30 into the compound of formula Ib,

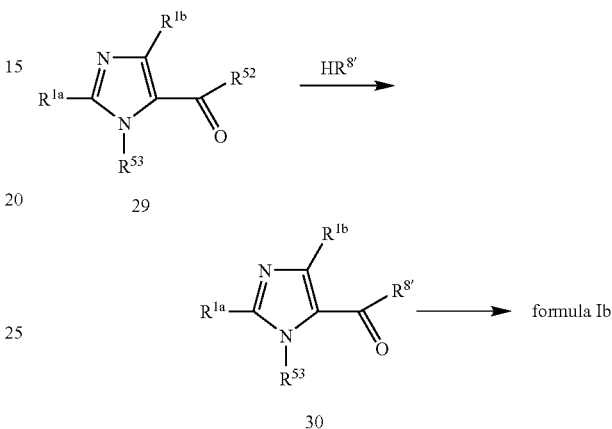

wherein the residue $R^{8'}$ represents —N($R^1$)—$R^2$—V-G-M as defined in claim 1, and where the residue $R^{53}$ denotes the group -Q-$R^0_{52}$ as defined in claim 1, and where the group —(C(O)—$R^{52}$ is a carboxylic acid group, and where the groups $R^{1a}$ and $R^{1b}$ in the formulae 29 and 30 have the corresponding definitions of $R^3$ and $R^4$ in formula Ib as defined in claim 1.

* * * * *